(12) United States Patent
Leblanc et al.

(10) Patent No.: US 8,314,112 B2
(45) Date of Patent: Nov. 20, 2012

(54) PYRROLOPYRIMIDINES AND PYRROLOPYRIDINES

(75) Inventors: Catherine Leblanc, West Sussex (GB); Robert Alexander Pulz, Basel (CH); Nikolaus Johannes Stiefl, Lorrach (DE)

(73) Assignee: Novartis AG, Basel (CH)

( * ) Notice: Subject to any disclaimer, the term of this patent is extended or adjusted under 35 U.S.C. 154(b) by 790 days.

(21) Appl. No.: 12/351,438

(22) Filed: Jan. 9, 2009

(65) Prior Publication Data
US 2009/0181941 A1 Jul. 16, 2009

(30) Foreign Application Priority Data

Jan. 11, 2008 (EP) .................................. 08150182

(51) Int. Cl.
*C07D 487/04* (2006.01)
*A61K 31/519* (2006.01)
*C07D 471/04* (2006.01)
*A61K 31/437* (2006.01)

(52) U.S. Cl. ................ 514/265.1; 544/280; 546/113; 514/300

(58) Field of Classification Search ............ 544/280; 514/265.1
See application file for complete search history.

(56) References Cited

U.S. PATENT DOCUMENTS

| 6,686,366 | B1 | 2/2004 | Castelhano et al. |
| 2002/0058667 | A1 | 5/2002 | Castelhano et al. |
| 2002/0094974 | A1 | 7/2002 | Castelhano et al. |
| 2003/0045536 | A1 | 3/2003 | Castelhano et al. |
| 2003/0073708 | A1 | 4/2003 | Castelhano et al. |
| 2003/0139427 | A1 | 7/2003 | Castelhano et al. |
| 2006/0205625 | A1 | 9/2006 | Straub et al. |
| 2007/0149561 | A1 | 6/2007 | Dhanak et al. |

FOREIGN PATENT DOCUMENTS

| WO | 9320078 | A1 | 10/1993 |
| WO | 0139777 | A1 | 6/2001 |
| WO | 02055084 | A1 | 7/2002 |
| WO | 02057267 | A1 | 7/2002 |
| WO | 03048120 | A2 | 6/2003 |
| WO | 2006087371 | A1 | 8/2006 |

OTHER PUBLICATIONS

Vippagunta, S.R., (Adv. Drug. Delivery Rev., 2001, 48, pp. 3-26).*

* cited by examiner

*Primary Examiner* — Susanna Moore
(74) *Attorney, Agent, or Firm* — John B. Alexander

(57) ABSTRACT

Compounds of formula I

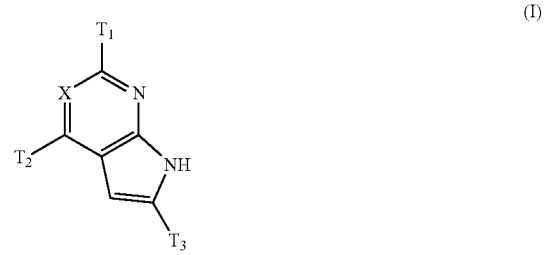

(I)

in free or salt or solvate form, wherein X, $T_1$, $T_3$ and $T_4$ have the meanings as indicated in the specification, are useful for treating diseases mediated by the ALK-5 and/or ALK-4 receptor. Pharmaceutical compositions that contain the compounds and processes for preparing the compounds are also described.

9 Claims, No Drawings

PYRROLOPYRIMIDINES AND PYRROLOPYRIDINES

This application is a US filing which claims the benefit of EP 08150182.7 filed Jan. 11, 2008.

This invention relates to organic compounds and their use as pharmaceuticals, in particular for the treatment of inflammatory or obstructive airways diseases such as pulmonary hypertension, pulmonary fibrosis, liver fibrosis; cancer; muscle diseases such as muscle atrophies and muscle dystrophies, and systemic skeletal disorders such as osteoporosis.

In one aspect, the present invention provides a compound of formula I

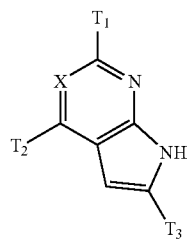

(I)

in free or salt or solvate form, wherein $T_1$ is a 4- to 14-membered heterocyclic group bound to the rest of the molecule via a ring carbon atom or $C_4$-$C_{15}$-cycloalkenyl each of which is unsubstituted or independently substituted at one, two or three positions by $R_1$, $C_1$-$C_8$-alkoxy, $C_3$-$C_{10}$-cycloalkyl, $C_1$-$C_8$-alkylthio, halo, halo-$C_1$-$C_8$-alkyl, amino, $C_1$-$C_8$-alkylamino, di($C_1$-$C_8$-alkyl)amino, cyano, oxo, hydroxy, carboxy or nitro;

$T_2$ is a 4- to 14-membered heterocyclic group bound to the rest of the molecule via a ring carbon atom and unsubstituted or independently substituted at one, two or three positions by $R_1$, $R_2$, $R_3$, $C_1$-$C_8$-alkoxy, $C_1$-$C_8$-alkoxycarbonyl, $C_1$-$C_8$-alkylthio, halo, halo-$C_1$-$C_8$-alkyl-$C_1$-$C_8$-alkylamino, di($C_1$-$C_8$-alkyl)amino, —C(=O)NR$_4$R$_5$, —NH(C=O)R$_1$, —NH(C=O)—$C_1$-$C_8$-alkyl-NR$_4$R$_5$, cyano, oxo, hydroxy, carboxy or nitro;

$R_1$ is $C_1$-$C_8$-alkyl, $C_2$-$C_8$-alkenyl or $C_2$-$C_8$-alkynyl unsubstituted or independently substituted at one, two or three positions by carboxy-$C_1$-$C_8$-alkyl, $C_1$-$C_8$-alkoxy-carbonyl-$C_1$-$C_8$-alkyl, hydroxy, oxo, cyano, amino, $C_1$-$C_8$-alkylamino, di($C_1$-$C_8$-alkyl)amino, $C_1$-$C_8$-alkanoylamino, carboxyl-$C_1$-$C_8$-alkylamino, $C_1$-$C_8$-alkoxy-carbonyl-$C_1$-$C_8$-alkylamino, N-(carboxyl-$C_1$-$C_8$-alkyl-N—($C_1$-$C_8$-alkyl)-amino, N—($C_1$-$C_8$-alkoxy-carbonyl-$C_1$-$C_8$-alkyl)-N—($C_1$-$C_8$-alkyl)-amino, amido-$C_1$-$C_8$-alkylamino, N-mono- or N,N-di-($C_1$-$C_8$-alkyl)-amido-$C_1$-$C_8$-alkylamino, tri-($C_1$-$C_8$-alkyl)-silanyl, halo, $C_1$-$C_8$-alkoxy, $R_3$, —C(=O)—$R_3$, —C(=O)NR$_4$R$_5$, —NH(C=O)—$C_1$-$C_8$-alkyl or —SO$_2$NR$_4$R$_5$;

$R_2$ is $C_6$-$C_{15}$-aryl, $C_4$-$C_{15}$-cycloalkyl or $C_4$-$C_{15}$-cycloalkenyl, each of which is unsubstituted or independently substituted at one, two or three positions by oxo, halo, hydroxy, $R_1$, $R_3$, $C_1$-$C_8$-alkylthio, amino, $C_1$-$C_8$-alkylamino, di($C_1$-$C_8$-alkyl)amino, cyano, carboxy, nitro, $C_6$-$C_{15}$-aryl-oxy, halo-$C_1$-$C_8$-alkyl, —NR$_4$R$_5$, R$_4$R$_5$N—$C_1$-$C_8$-alkyl, R$_4$R$_5$N—$C_1$-$C_8$-alkoxy, $R_3$—$C_1$-$C_8$-alkyl, —O—$R_1$, —O—$R_3$, —C(=O)—$R_3$, —C(=O)—NH$_2$, —C(=O)NR$_4$R$_5$, —C(=O)—O—$R_1$, —O—C(=O)—$R_1$, —SO$_2$—NH$_2$, —SO$_2$—$R_1$, $C_1$-$C_8$-alkyl-SO$_2$—NH—, —C(=O)—NH—$R_3$, aryl-$C_6$-$C_{15}$—SO$_2$—, —SO$_2$—$R_3$ or —SO$_2$NR$_4$R$_5$;

$R_3$ is a 4- to 14-membered heterocyclic group bound via a carbon atom or, if it comprises a ring nitrogen not bound to a double bond, via a ring nitrogen or a ring carbon atom, and is unsubstituted or independently substituted at one, two or three positions by oxo, amino, halo, $C_1$-$C_8$-alkylamino, di($C_1$-$C_8$-alkyl)amino, cyano, hydroxy, carboxy, nitro, $R_1$, $C_1$-$C_8$-alkoxy, $C_1$-$C_8$-alkylthio, halo-$C_1$-$C_8$-alkyl, —C(=O)—$R_1$, —C(=O)—NH$_2$ or —SO$_2$—NH$_2$;

$R_4$ and $R_5$ are independently hydrogen, $R_1$, $C_1$-$C_8$-alkylamino, di($C_1$-$C_8$-alkyl)amino, $C_6$-$C_{15}$-aryl, $C_6$-$C_{15}$-aryl-$C_1$-$C_8$-alkyl, $C_1$-$C_8$-alkylamino-$C_1$-$C_8$-alkyl, di($C_1$-$C_8$-alkyl)amino-$C_1$-$C_8$-alkyl, —C(=O)—$R_1$, $R_3$ or —$C_1$-$C_8$-alkyl-$R_3$;

$T_3$ is H, $R_1$, OH or NH$_2$; and

X is either N or CH;

with the proviso that if X is CH, then $T_2$ is a 4- or 6- to 14-membered heterocyclic group bound to the rest of the molecule via a ring carbon atom, and is unsubstituted or independently substituted at one, two or three positions by $R_1$, $R_2$, $R_3$, $C_1$-$C_8$-alkoxy, $C_1$-$C_8$-alkoxycarbonyl, $C_1$-$C_8$-alkylthio, halo, halo-$C_1$-$C_8$-alkyl, amino, $C_1$-$C_8$-alkylamino, di($C_1$-$C_8$-alkyl)amino, —C(=O)NR$_4$R$_5$, —NH(C=O)R$_1$, —NH(C=O)—$C_1$-$C_8$-alkyl-NR$_4$R$_5$, cyano, oxo, hydroxy, carboxy or nitro.

The terms used in the specification preferably have the following meanings, where one, several or all more general expressions may independently be replaced by more precise definitions in embodiments or preferred embodiments of the invention in order to define more preferred inventions:

"Unsubstituted or substituted" as used herein means the group referred to can be unsubstituted, or substituted at one or where mentioned in one, two or three positions by any one or any combination of the radicals listed thereafter, "independently" meaning that where more than one substituent is possible, the substituents can be chosen independently from those mentioned, so that they can be different or partially or all the same.

"Halo" or "halogen" as used herein denotes the bound form of an element belonging to group 17 (formerly group VII) of the Periodic Table of Elements, which may be, for example, fluorine, chlorine, bromine or iodine.

"$C_1$-$C_8$-alkyl" as used herein denotes straight chain, branched ("branched wherever used meaning branched once or more often, e.g. branched once or twice) or cyclic alkyl that contains one to eight, e.g. one to seven, preferably one to four carbon atoms and which may be substituted by one or more, e.g. up to three independently selected substituents, e.g. $R_1$, carboxy-$C_1$-$C_8$-alkyl, $C_1$-$C_8$-alkoxy-carbonyl-$C_1$-$C_8$-alkyl, $C_1$-$C_8$-alkoxy, $C_3$-$C_5$-cycloalkyl, $C_1$-$C_8$-alkylthio, halo, halo-$C_1$-$C_8$-alkyl, amino, $C_1$-$C_8$-alkylamino, di($C_1$-$C_8$-alkyl)amino, carboxyl-$C_1$-$C_8$-alkylamino, $C_1$-$C_8$-alkoxycarbonyl-$C_1$-$C_8$-alkylamino, N-(carboxyl-$C_1$-$C_8$-alkyl)-N—($C_1$-$C_8$-alkyl)-amino, N—($C_1$-$C_8$-alkoxy-carbonyl-$C_1$-$C_8$-alkyl)-N—($C_1$-$C_8$-alkyl)-amino, cyano, oxo, hydroxy, carboxy or nitro, or preferably unsubstituted.

"$C_2$-$C_8$-alkenyl" as used herein denotes a straight chain or branched hydrocarbon chain that contains two to 8 carbon atoms and one or more unconjugated or conjugated double bonds.

"$C_2$-$C_8$-alkynyl" as used herein denotes a straight chain or branched hydrocarbon chain that contains two to 8 carbon atoms and one or more triple bonds.

Hydroxy or amino substituents on $C_2$-$C_8$-alkenyl or $C_2$-$C_8$-alkynyl are preferably not bound at a carbon that participates at a double or triple bond.

"$C_6$-$C_{15}$-aryl", as used herein, represents carbocyclic aryl or biaryl having 6- to 15-ring carbon atoms. It can be monocyclic, bicyclic or tricyclic, and may be substituted by one or more radicals. Examples of $C_6$-$C_{15}$-aryl groups include but are not limited to phenyl, phenylene, benzenetriyl, indanyl, naphthyl, naphthylene, naphthalenetriyl, anthrylene or fluorenyl, especially phenyl, napthyl or fluorenyl.

"4- to 14-membered heterocyclic group", if not indicated otherwise by different numbers, refers to a 4- to 14-membered heterocyclic ring containing at least one, e.g. up to four, for example up to three, ring heteroatoms independently selected from the group consisting of nitrogen, oxygen and sulphur, which may be saturated, partially saturated or unsaturated, that is, "heterocyclic" includes e.g. heteroaryl, heterocycloalkenyl and heterocycloalkyl groups. Examples of 4- to 14-membered heterocyclic groups include but are not limited to furanyl, azetidinyl, pyrrolyl, pyrrolidinyl, pyrazolyl, imidazolyl, imidazolidinyl, triazolyl, isotriazolyl, tetrazolyl, thiadiazolyl, isothiazolyl, oxadiazolyl, pyridinyl, piperidinyl, oxazolyl, isoxazolyl, pyrazinyl, pyridazinyl, pyrimidinyl, piperazinyl, pyrrolidinone-yl, pyridinone-yl, morpholinyl, thiomorpholinyl, S-oxo-thiomorpholinyl, S,S-dioxo-thiomorpholinyl, triazinyl, oxazinyl, tetrahydrofuranyl, tetrahydrothiophenyl, tetrahydrothiopyranyl, tetrahydropyranyl, 1,4-dioxanyl, 1,4-oxathianyl, indazolyl, indolyl, isoindolyl, thiazolyl, thiophenyl, quinolinyl, isoquinolinyl, tetrahydroquinolyl, tetrahydroisoquinolyl, benzothiophenyl, benzoxazolyl, benzisoxazolyl, benzothiazolyl, benzisothiazolyl, benzofuranyl, dihydrobenzofuranyl, benzodioxolyl, benzimidazolyl, 3,4-dihydro-2H-pyranopyridinyl or tetrahydronaphthyridinyl, or azetidinyl, tetrahydropyridinyl, oxadiazolyl, such as [1,3,4]oxadiazol-2-yl, or tetrazolyl. The 4- to 14-membered heterocyclic group can be unsubstituted or substituted as indicated above and below. "4- or 6- to 14-membered" means that five-membered rings are not encompassed, e.g. those in the preceding list of examples of heterocyclic rings.

$C_4$-$C_{15}$-Cycloalkenyl is a partially unsaturated carbocylic, mono-, bi- or tricyclic ring with at least one double bond, such as cyclobutenyl, cyclopentenyl, e.g. cyclopenten-2- or -3-yl or cyclopent-1-enyl, cyclohexenyl, e.g. cyclohexen-2- or -3-yl, cycloheptenyl, e.g. cyclohepten-2-, -3- or -4-yl, cyclooctenyl, cyclononenyl or cyclodecenyl, or a bicyclic group such as bicycloheptenyl or bicyclooctenyl, and can be unsubstituted or substituted as indicated above and below.

"-membered", e.g. 4- to 14-membered, refers to the number of ring atoms in a cyclic moiety.

Heteroaryl is preferably an aromatic monocyclic or bicyclic hydrocarbon containing from (if not indicated otherwise) 4 to 15 ring atoms one or more of which are heteroatoms selected from O, N or S. Preferably there are one or two heteroatoms. Heterocyclic aryl represents, for example: pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl. Heterocyclic aryl also includes such substituted radicals.

Heterocycloalkyl represents a mono-, di- or tricyclic hydrocarbon which may be saturated or unsaturated and which contains one or more, preferably one to three heteroatoms selected from O, N or S and has (if not indicated otherwise) 4 to 15 ring atoms. The term heterocyclo-alkyl is intended also to include bridged heterocycloalkyl groups such as 3-hydroxy-8-aza-bi-cyclo[3.2.1]oct-8-yl and fused ring systems.

Cycloalkyl denotes a fully saturated carbocyclic ring. Thus, "$C_3$-$C_{10}$-cycloalkyl" denotes a fully saturated carbocyclic ring having 3 to 10 ring carbon atoms, "$C_4$-$C_{15}$-cycloalkyl" denotes a fully saturated carbocyclic ring having 4 to 15 ring carbon atoms. For example, cycloalkyl is a monocyclic group such as a cyclopropyl, cyclobutyl, cyclopentyl or cyclohexyl, cycloheptyl, cyclooctyl, cyclononyl or cyclodecyl, or a bicyclic group such as bicycloheptyl or bicyclooctyl.

"Halo-$C_1$-$C_8$-alkyl" as used herein denotes $C_1$-$C_8$-alkyl as hereinbefore defined substituted by one or more halogen atoms, preferably one, two or three halogen atoms. An example is trifluoromethyl.

"$C_1$-$C_8$-alkylamino" or "di($C_1$-$C_8$-alkyl)amino" as used herein denote amino substituted by one or two $C_1$-$C_8$-alkyl groups as hereinbefore defined, which may be the same or different.

"$C_1$-$C_8$-alkylthio" as used herein denotes straight chain or branched alkylthio that has 1 to 8 carbon atoms.

"$C_1$-$C_8$-alkoxy" as used herein denotes straight chain or branched alkoxy that has 1 to 8 carbon atoms.

"$C_1$-$C_8$-alkoxycarbonyl" "$C_1$-$C_6$-alkyl-O—C(=O)—") as used herein denotes straight chain or branched $C_1$-$C_7$-alkoxy as hereinbefore described attached through the oxygen atom to a carbonyl (—C(=O)—) group.

$C_1$-$C_8$-Alkylsulfanyl means the same as $C_1$-$C_8$-alkylthio ($C_1$-$C_8$-alkyl-S—).

Tri-($C_1$-$C_8$-alkyl)-silanyl can e.g. be trimethylsilanyl.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

The mentioning of any reference documents (which preferably, at least as far as the matter mentioned is concerned, are incorporated by reference here) in the present disclosure does not constitute any admission that these documents are prior art affecting the patentability of the present invention(s).

According to the invention, with respect to formula (I), the following significances are preferred independently, collectively or in any combination or sub-combination:

(i) $T_1$ is a 6-membered heteroaryl group which is unsubstituted or substituted as defined above or preferably as below;

(ii) $T_1$ is pyridinyl which is unsubstituted or substituted as defined above or preferably below;

(iii) $T_2$ is a 6-membered heteroaryl group that is unsubstituted or substituted as defined above or preferably below;

(iv) $T_2$ is unsubstituted or substituted pyridinyl, where the substituents are as defined above or preferably below;

(v) $T_2$ is unsubstituted or substituted heteroaryl-pyridinyl, where the substituents are as defined above or preferably below;

(vi) $T_2$ is unsubstituted or substituted phenyl-pyridinyl, where the substituents are as defined above or preferably below;

(vii) $T_3$ is H;

(viii) $T_3$ is $C_1$-$C_8$-alkyl;

(ix) $T_3$ is OH (x) $T_3$ is $NH_2$;

(xi) X is CH;

(xii) X is N; or (xiii) $T_2$ is unsubstituted or substituted bipyridyl or tetrahydrobipyridyl, wherein the substituents are as defined above or preferably below for a<4- to 14-membered heterocyclic group.

Compounds of the formula I may be present in the free form, in the salt form, or in solvate form, this also including mixtures of two or more such forms.

Compounds of formula I that contain a basic centre, such as amino or imino or =N—, are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid, hydroiodic acid, nitric acid, sulfuric acid, phosphoric acid; and organic acids, for example aliphatic monocarboxylic acids such as formic acid, acetic acid, trifluoroacetic acid, propionic acid and butyric acid, caprylic acid, dichloroacetic acid, hippuric acid, aliphatic hydroxy acids such as lactic acid, citric acid, tartaric acid or malic acid, gluconic acid, mandelic acid, dicarboxylic acids such as maleic acid or succinic acid, adipic acid, aspartic acid, fumaric acid, glutamic acid, malonic acid, sebacic acid, aromatic carboxylic acids such as benzoic acid, p-chloro-benzoic acid, nicotinic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid, ethanesulfonic acid, ethane-1,2-disulfonic acid, 2-hydroxy-ethanesulfonic acid, (+) camphor-10-sulfonic acid, naphthalene-2-sulfonic acid, naphthalene-1,5-disulfonic acid or p-toluenesulfonic acid. These salts may be prepared from compounds of formula I by known salt-forming procedures. Pharmaceutically acceptable solvates are generally hydrates.

Compounds of formula I which contain acidic, e.g. carboxyl, groups, are also capable of forming salts with bases, in particular pharmaceutically acceptable salt, e.g. with bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine, arginine, benethamine, benzathine, diethanol-amine, 4-(2-hydroxy-ethyl)morpholine, 1-(2-hydroxyethyl)pyrrolidine, N-methyl glutamine, piperazine, triethanol-amine or tromethamine. These salts may be prepared from compounds of formula I by known salt-forming procedures.

Compounds of formula I that contain both acidic, e.g. carboxyl, and basic, e.g. amino, imino or =N— groups, may also exist as zwitterions.

Mixed salts with more than one counter-ion are included by the term salt.

Pharmaceutically acceptable salts are preferred.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Some compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

The invention includes all such forms, in particular the pure isomeric forms. The different isomeric forms may be separated or resolved one from the other by conventional methods, or any given isomer may be obtained by conventional synthetic methods or; by stereospecific or asymmetric syntheses.

Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

The invention includes all pharmaceutically acceptable isotopically-labelled compounds of formula I wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^2H$ and $^3H$, carbon e.g. $^{11}C$, $^{13}C$ and $^{14}C$, chlorine e.g. $^{36}Cl$, fluorine e.g. $^{18}F$, iodine e.g. $^{123}I$ and $^{125}I$, nitrogen e.g. $^{13}N$ and $^{15}N$, oxygen e.g. $^{15}O$, $^{17}O$ and $^{18}O$, and sulfur e.g. $^{35}S$.

Certain isotopically-labelled compounds of formula I, for example those incorporating a radioactive isotope, are useful in drug and/or substrate tissue distribution studies. The radioactive isotopes tritium ($^3H$) and carbon-14 ($^{14}C$) are particularly useful for this purpose in view of their ease of incorporation and ready means of detection. Substitution with heavier isotopes such as deuterium ($^2H$) may afford certain therapeutic advantages that result from greater metabolic stability, for example increased in vivo half-life or reduced dosage requirements, and hence may be preferred in some circumstances. Substitution with positron emitting isotopes, such as $^{11}C$, $^{18}F$, $^{15}O$, and $^{13}N$ can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying examples using an appropriate isotopically-labelled reagent in place of the non-labelled reagent previously used.

Pharmaceutically acceptable solvates in accordance with the invention include those wherein the solvent of crystallisation may be isotopically substituted e.g. $D_2O$, $d_6$-acetone or $d_6$-DMSO. Hydrates or solvates with isotopically un-enriched water or solvents are preferred.

Specific especially preferred compounds of the invention are those described hereinafter in the Examples.

The present invention also provides a process for the preparation of compounds of formula I in free or salt or solvate form.

According to a further aspect of the invention there is provided a process of preparing a compound of formula I comprising:

a) reacting a compound of formula II,

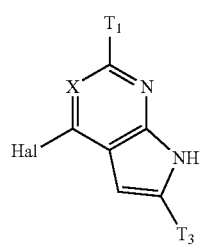

(II)

wherein X, $T_1$ and $T_3$ is as defined for a compound of the formula I and Hal is halo, under coupling conditions with a coupling reagent of formula III:

$T_2\text{-B(OR)}_2$ (III)

wherein $T_2$ is as defined for a compound of the formula I and R is hydrogen or alkyl, e.g. $C_1$-$C_8$-alkyl, or the two moieties R together form a methylene or ethylene bridge that may be unsubstituted or substituted up to four times by $C_1$-$C_8$-alkyl, or b) for the manufacture of a compound of the formula I wherein $T_2$ is a group of the formula IVA,

$R_5R_4N\text{—}CH_2\text{-}T_2^*\text{-}$ (IVA)

wherein $R_4$ is hydrogen and $R_5$ is $C_1$-$C_8$-alkyl and $T_2^*$ is unsubstituted $T_2$ as defined for a compound of the formula I, reductively aminating an aldehyde compound of the formula IV,

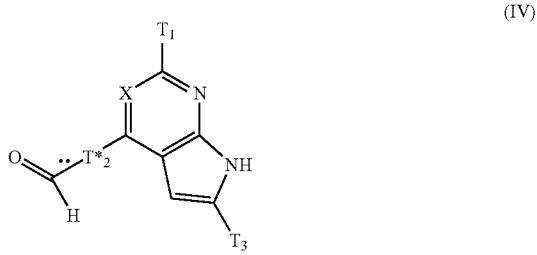

(IV)

wherein $T^*_2$ is unsubstituted $T_2$ as defined for a compound of the formula I, and wherein X, $T_1$ and $T_3$ are as defined for a compound of the formula I, with an amino compound of the formula V,

$HNR_4R_5$ (V)

wherein $R_4$ is hydrogen and $R_5$ is $C_1$-$C_8$-alkyl, and, if desired, converting an obtainable compound of the formula I into a different compound of the formula I, an obtainable free form of a compound of the formula I into a salt, an obtainable salt of a compound of the formula I into a different salt, an obtainable solvent-free form of a compound of the formula I into a solvate and/or an obtainable solvate form of a compound of the formula I into a solvent free form;

where in each of the reactions and/or conversions, protecting groups may be employed and later removed following standard methods.

The reactions preferably take place as follows:

For reaction a, preferably the conditions of a Suzuki-Miyaura or analogue coupling reaction are employed.

The reaction given under process variant a) is preferably carried out under the conditions of a Suzuki-reaction, preferably in a mixture of a polar aprotic solvent, such as dimethylformamide (DMF), an alcohol, such as ethanol, and/or acetonitrile, and optionally water, in the presence of a catalyst for the cross-coupling, especially a noble metal catalyst, preferably a palladium catalyst, such as palladium(II) complex, for example (preferably if Hal is chloro) bis(triphenylphosphine)palladium (II) dichloride, in the presence of a base, such as potassium carbonate, sodium hydroxide or sodium carbonate, at a preferred temperature in the range from 80° C. to 160° C.; or according to a another preferred method in a cyclic ether solvent, e.g. tetrahydrofuran, and or one or more of the solvents just mentioned above, in the presence of a catalyst for the cross coupling, especially a noble metal catalyst, preferably a palladium(0) complex, for example tris(dibenzylideneacetone)-dipalladium(0) or (especially if Hal is iodo) tetrakis(triphenylphosphine)palladium(0), or of palladium dibenzylideneacetone as precursor, in the presence an appropriate ligand, such as 2-dicyclohexylphosphino-2',6'-dimethoxybiphenyl (SPhos) or 2-dicyclohexylphosphino-2'-(N,N-dimethylamino)-biphenyl (P1), and in the presence of a base, e.g. as mentioned above or potassium phosphate, and at a preferred temperatures in the range from 80 to 150° C.; if required conducting the reaction in a sealed vessel (e.g. a seal reactor) if the boiling point of the reaction mixture is exceeded and especially if (as is a preferred embodiment) the heating is effected by microwave excitation. Where required, other or additional catalyst can be added, e.g. ($PdCl_2(PPh_2)\cdot Fe\cdot C\cdot H_2Cl_2$).

The reaction under b) preferably takes place in the presence of a complex hydrogenation agent, especially $NaBH(OAc)_3$, in an appropriate solvent or solvent mixture, e.g. acetic acid and methylene chloride, at temperatures in a preferred range from 0 to 50° C.

Protecting Groups

If one or more other functional groups, for example carboxy, hydroxy, amino, are or need to be protected in a starting material, e.g. in any one or more starting materials, intermediates and educts, because they should not take part in the reaction or disturb the reaction, these are such groups as are usually used in the synthesis of peptide compounds, and also of cephalosporins and penicillins, as well as nucleic acid derivatives and sugars. Protecting groups are such groups that are no longer present in the final compounds once they are removed, while groups that remain as substitutents are not protecting groups in the sense used here which is groups that are added at a certain intermediate stage and removed to obtain a final compound. For example, tert-butoxy if remaining in a compound of the formula I is a substituent, while if it is removed to obtain the final compound of the formula I it is a protecting group. Carboxy (—COOH, also called carboxyl herein) can be set free from esterified carboxy, such as $C_1$-$C_8$-alkoxycarbonyl, e.g. methoxycarbonyl, by hydrolysis, e.g. in the presence of acid or preferably a base, e.g. an alkali metal hydroxide, such as lithium hydroxide, sodium hydroxide or potassium hydroxide, in an appropriate solvent, e.g. a $C_1$-$C_8$.alkanol, such as methanol, preferably in the presence water, e.g. at temperatures in the range from –10 to 50° C.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/1, Georg Thieme Verlag, Stuttgart 1974, in H.-D. Jakubke and H. Jescheit, "Aminosaüren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

For example, an amino protecting tert-butoxycarbonyl group can be removed by acidolysis, e.g. with trifluoroacetic acid in the presence of an appropriate solvent, such as dichloromethane, at preferred temperatures in the range from −10 to 50° C.

Optional Reactions and Conversions

A compound of the formula I may be converted into a different compounds of the formula I according to standard reaction procedures.

For example, in a compound of the formula I wherein $T_2$ is a 4- to 14-membered heterocyclic group bound to the rest of the molecule via a ring carbon atom, carrying a bromo substituent, the bromo can be converted into unsubstituted or substituted $C_6$-$C_{15}$-aryl $R_2$ or into unsubstituted or substituted 4- to 14-membered heterocyclic group bound via a carbon atom $R_3$, each as defined for a compound of the formula I, by coupling under coupling conditions analogous to those described above for process variant a) with a compound of the formula VI

$$R_{23}\text{---}B(OR)_2 \qquad (VI)$$

wherein $R_{23}$ is $R_2$ or $R_3$ as just defined and R is as defined above for a compound of the formula III; or alternatively the bromo can be converted into $R_3$ in the form of a 4- to 14-membered heterocyclic group that is unsubstituted or substituted as defined for a compound of the formula I and bound via a ring nitrogen by coupling reaction with a compound of the formula VII,

$$R_3^*\text{---}H \qquad (VII)$$

wherein $R_3^*$ is $R_3$ in the form of a 4- to 14-membered heterocyclic group that is unsubstituted or substituted as defined for a compound of the formula I and bound via a ring nitrogen, preferably in the presence of a catalyst, e.g. tris (dibenzylideneacetone)di-palladium(0), in the presence of 2-dicyclohexylphosphino-2'-(N,N-dimethylamino)-biphenyl or 2-dicyclohexylphosphino-biphenyl in an appropriate solvent, e.g. toluene or tetrahydrofuran, at elevated temperatures, e.g. under reflux conditions.

In a compound of the formula I which carries a substituent $R_3$ in the form of carboxyl, e.g. on $T_2$, the carboxyl can be converted into a group —C(=O)—$NR_4R_5$ wherein $R_4$ and $R_5$ are as defined for a compound of the formula I by reacting the carboxyl group of the compound of the formula I in the presence of a coupling agent for amide synthesis with an amine compound of the formula VIII,

$$HNR_4R_5 \qquad (VIII)$$

wherein $R_4$ and $R_5$ are as defined for a compound of the formula I, to the corresponding amide.

The reaction preferably takes place in an appropriate solvent, e.g. acetonitrile, in the presence of a tertiary nitrogen base, e.g. triethylamine, at preferred temperatures between 30° C. and the reflux temperature of the reaction mixture, e.g. at about 130 to 150° C. As coupling agent for amide synthesis, any reagent or reagent mixture that activates the carboxyl group in situ is possible, for example dicyclohexylcarbodiimide/1-hydroxybenzotriazole (DCC/HOBt); bis(2-oxo-3-oxazolidinyl)phosphinic chloride (BOPCl); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluorophosphate (PyBOP), O-(1H-6-chlorobenzotriazole-1-yl)-1,1,3,3-tetramethyl-uronium hexafluorophosphate, 1-(3-dimethylaminopropyl)-3-ethylcarbodiimide hydrochloride/ hydroxybenzotriazole or 1-hydroxy-7-azabenzotriazole (EDC/HOBt or EDC/HOAt) or HOAt alone, or with (1-chloro-2-methyl-propenyl)-dimethylamine. For review of some other possible coupling agents, see e.g. Klauser; Bodansky, *Synthesis* (1972), 453-463.

In a compound of the formula I wherein one or more of $T_1$ and especially $T_2$ carries a cyano group, this may be converted into tetrazol-5-yl, e.g. in the presence of an inorganic azide, such as an alkali metal azide, e.g. sodium azide, in the presence of a salt of a nitrogen base, e.g. an ammonium halogenide, such as ammonium chloride, in an appropriate solvent, such as an acid amide, e.g. N,N-dimethyl-formamide, preferably at elevated temperatures, e.g. from 50 to 130° C.

In a compound of the formula I wherein one or more of $T_1$, and especially $T_2$ carries a tri-($C_1$-$C_8$-alkyl)-silanyl)-ethynyl group, this may be converted into the free ethynyl e.g. by reaction with tert-butyl ammonium fluoride (TBAF) in an appropriate solvent, e.g. a cyclic ether, such as tetrahydrofurane, e.g. at temperatures in the range from −10 to 50° C.

In a compound of the formula I wherein one or more of $T_1$, and especially $T_2$ carries a bromo substituent, this may be converted into prop-1-ynyl substituted in 3-position by a moiety Rx selected from carboxy-$C_1$-$C_8$-alkyl, $C_1$-$C_8$-alkoxycarbonyl-$C_1$-$C_8$-alkyl, hydroxy, oxo, cyano, amino, $C_1$-$C_8$-alkylamino, di($C_1$-$C_8$-alkyl)amino, $C_1$-$C_8$-alkanoylamino, carboxyl-$C_1$-$C_8$-alkylamino, $C_1$-$C_8$-alkoxy-carbonyl-$C_1$-$C_8$-alkylamino, N-(carboxyl-$C_1$-$C_8$-alkyl)-N—($C_1$-$C_8$-alkyl)-amino, N—($C_1$-$C_8$-alkoxy-carbonyl-$C_1$-$C_8$-alkyl)-N—($C_1$-$C_8$-alkyl)-amino, amido-$C_1$-$C_8$-alkylamino, N-mono- or N,N-di-($C_1$-$C_8$-alkyl)-amido-$C_1$-$C_8$-alkylamino, tri-($C_1$-$C_8$-alkyl)-silanyl, halo, $C_1$-$C_8$-alkoxy, $R_3$, —C(=O)—$R_3$, —C(=O)$NR_4R_5$, —NH(C=O)—$C_1$-$C_8$-alkyl and —$SO_2NR_4R_5$ (where reactive groups are protected if necessary and deprotected after the reaction) by reaction with a compound of the formula

$$Rx\text{-}CH_2\text{---}C\equiv CH \qquad (XVII)$$

wherein Rx is as just defined. The reaction preferably takes place in the presence of an appropriate solvent, such as dimethoxyethane, and in the presence of an appropriate base, e.g. a tertiary nitrogen base, such as triethylamine, and in the presence of an appropriate catalyst or catalyst mixture, such as copper (I) iodide and Pd($PPh_3$), preferably at elevated temperatures, e.g. in the range from 50 to 130° C.

In a compound of the formula I wherein one or more of $T_1$ and especially $T_2$ carries a $C_1$-$C_8$-alkoxycarbonyl-$C_1$-$C_7$-alkyl moiety, this may be converted into the corresponding hydroxyl-$C_2$-$C_8$-alkyl moiety e.g. by reduction with an appropriate complex hydride, such as lithium aluminiumhydride, in an appropriate solvent, such as a cyclic ether, e.g. tetrahydrofurane, e.g. at temperatures in the range from −10 to 50° C.

Other conversion reaction may be analogous to deprotection reactions.

Also in the optional process steps, carried out "if desired", functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. Salts with bases may be obtained with a base or with a suitable cation exchange reagent.

Salts can usually be converted to free compounds, e.g. by treating with suitable basic compounds, for example with alkali metal carbonates, alkali metal hydrogencarbonates, or alkali metal hydroxides, typically potassium carbonate or sodium hydroxide or by treating with suitable acidic compounds, e.g. hydrohalic acids, such as HCl or HBr.

Mixtures of constitutional isomers or of products and by-products can be separated according to standard procedures, e.g. by distribution, chromatography, selective crystallization or the like.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

The invention thus also includes a compound of the formula I in isomerically pure form, or a salt and/or a solvate thereof, and its uses etc.

It should be emphasized that reactions analogous to the conversions mentioned in this chapter may also take place at the level of appropriate intermediates (and are thus useful in the preparation of corresponding starting materials).

Especially preferred (also in the case of preparation of starting materials described below) are reaction conditions and reactants as described in the examples, or analogous conditions and reactions.

Starting Materials:

The starting materials of the formulae II to VIII as well as other starting materials, intermediates or educts mentioned herein, e.g. below, can be prepared according to or in analogy to methods that are known in the art, the materials are known in the art and/or are commercially available, or as or in analogy to methods mentioned in the Examples. Novel starting materials, as well as processes for the preparation thereof, are likewise an embodiment of the present invention. In the preferred embodiments, such starting materials are used and the reaction chosen are selected so as to enable the preferred compounds to be obtained.

The invention also relates to the novel starting materials and intermediates disclosed herein, as well as salts and/or solvates thereof.

For example, a starting material of the formula II wherein X is N and the other symbols are as defined for a compound of the formula II can be prepared from a precursor compound of the formula II where instead of the iodo a chloro is present as Hal by reacting is in the presence of an acid, especially hydrohalic acid, in an appropriate solvent, e.g. dioxane and/or acetonitrile, at elevated temperatures, e.g. between 100 and 180° C., with an alkalimetal iodide, such as sodium iodide.

A compound of the formula II wherein Hal is chloro, X is N and the other moieties are as defined for a compound of the formula II can be obtained by reacting a hydroxy compound of the formula IX,

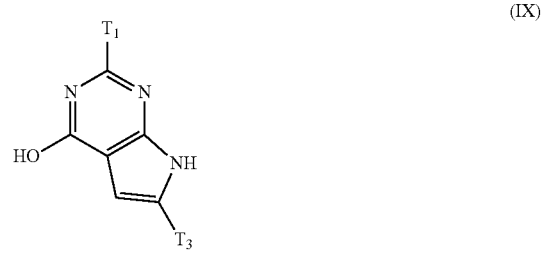

(IX)

wherein $T_1$ and $T_3$ are as defined for a compound of the formula I, by reacting it with an inorganic acid chloride, preferably $POCl_3$, preferably without solvent and preferably at temperatures in the range from 50 to 120° C.

Analogously, using other inorganic acid halides, other compound of the formula II wherein Hal is Halo other than chloride may be obtained.

A compound of the formula IX is preferably obtained by reacting a carboxyamidine compound of the formula X,

$T_1\text{-C}(=\!\text{NH})\!-\!\text{NH}_2$  (X)

wherein $T_1$ is as defined for a compound of the formula I, with 2-cyano-4,4-diethoxy-butyric acid ethyl ester, e.g. after dissolving the compound of the formula II in an appropriate solvent, such as an alcohol, e.g. ethanol, in the presence of a strong base, e.g. an alkalimetal methylate, such as sodium methylate ($NaOCH_3$), and first allowing a reaction at a temperature e.g. in the range from 10 to 50° C., and then adding the 2-cyano-4,4-diethoxy-butyric acid ethyl ester and reacting at a preferred temperature in the range from 40 to 90° C.

A carboxyamidine of the formula X may, for example, be obtained from a carboximidic acid compound of the formula XI,

$T_1\text{-C}(=\!\text{NH})\!-\!\text{O-Alk}$  (XI)

wherein $T_1$ is as defined for a compound of the formula I and Alk is alkyl, e.g. $C_1\text{-}C_8$-alkyl, by reacting it with an ammonium salt, such as ammonium chloride, in the presence of an appropriate solvent or solvent mixture, e.g. an alcohol, such as ethanol, and/or water, preferably at elevated temperatures, e.g. in the range from 50 to 90° C.

A carboximic acid ester of the formula XI can, for example, be obtained by reaction of a cyano compound of the formula XII,

$T_1\text{-CN}$  (XII)

wherein $T_1$ is as defined for a compound of the formula I, with the corresponding alcoholate of an alcohol Alk-OH wherein Alk is as defined for a compound of the formula XII, e.g. with an alkalimetal alcoholate, such as sodium methanolate, in the corresponding alcohol, e.g. methanol, preferably at temperatures between 0 and 50° C.

A starting material of the formula II wherein X is CH can preferably be obtained by reacting a compound of the formula XIII,

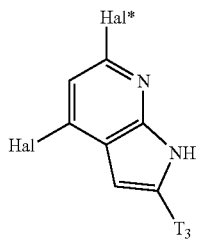

(XIII)

wherein T₃ is as defined for a compound of the formula I and Hal and Hal* are two different halo substituents, especially Hal being chloro and Hal* bromo, with a stannate compound of the formula XIV,

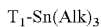

(XIV)

wherein T₁ is as defined for a compound of the formula I and Alk is alkyl, especially $C_1$-$C_8$-alkyl, such as n-butyl, in the presence of a catalyst, such as tetrakis(triphenylphosphine)-palladium(0), in an appropriate solvent, such as acetonitrile, preferably at elevated temperatures, e.g. from 150 to 170° C.

A compound of the formula XIII may, for example, be obtained by reacting a compound of the formula XV,

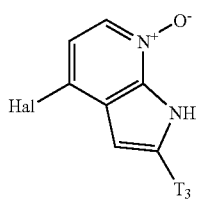

(XV)

wherein T₃ is as defined for a compound of the formula I and Hal is halo, especially chloro, with an acid halide, especially benzoyl halide, wherein the halide component corresponds to Hal*, e.g. is bromo, in an appropriate solvent, e.g. tetrahydrofuran, and hexamethyldisilazane at a temperature preferably in the range from 0 to 50° C.

A compound of the formula XV may, for example, be obtained by oxidising a pyrrolopyridine compound of the formula XVI,

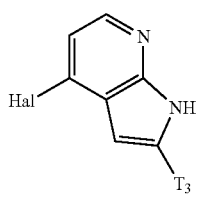

(XVI)

wherein Hal and T₃ are as defined for a compound of the formula XV, e.g. by reacting it with an organic peroxide, such a m-chloro-perbenzoic acid, in an appropriate solvent, e.g. chloroform, e.g. at temperatures in the range from −25 to 20° C.

The starting materials of the formula III, IV, V, XII, XIV and XVI, as well as other starting materials, can be obtained according to methods known in the art, are commercially available, or they preferably can be prepared by methods or in analogy to methods described in the Examples, using the appropriate starting materials and corresponding reaction conditions.

The agents of the invention (another word used herein for compounds of the formula I, their salts or their solvents) act as activin-like kinase ("ALK")-5 inhibitors. At least many of these compounds also act as ALK-4 inhibitors too.

TGF-β1 is the prototypic member of a family of cytokines including the TGF-βs, activins, inhibins, bone morphogenetic proteins and Mullerian-inhibiting substance, that signal through a family of single transmembrane serine/threonine kinase receptors. These receptors can be divided into two classes, the type I or activin like kinase (ALK) receptors and type II receptors. The ALK receptors are distinguished from the type II receptors in that the ALK receptors (a) lack the serine/threonine rich intracellular tail, (b) possess serine/threonine kinase domains that are very homologous between type I receptors, and (c) share a common sequence motif called the GS domain, consisting of a region rich in glycine and serine residues. The GS domain is at the amino terminal end of the intracellular kinase domain and is critical for activation by the type II receptor. Several studies have shown that TGF-β signalling requires both the ALK and type II receptors. Specifically, the type II receptor phosphorylates the GS domain of the type I receptor for TGF-β, ALK5, in the presence of TGF-β. The ALK5, in turn, phosphorylates the cytoplasmic proteins smad2 and smad3 at two carboxy terminal serines. The phosphorylated smad proteins translocate into the nucleus and activate genes that contribute to the production of extracellular matrix. Therefore, preferred compounds of this invention are selective in that they inhibit the type I receptor.

Activins transduce signals in a manner similar to TGF-β. Activins bind to serine/thereonine kinase, the activin type II receptor (ActRIIB), and the activated type II receptor hyperphosphorylates serine/threonine residues in the GS region of the ALK4. The activated ALK4 in turn phosphorylates Smad2 and Smad3. The consequent formation of a hetero-Smad complex with Smad4 results in the activin-induced regulation of gene transcription.

Activation of the TGF-β1 axis and expansion of extracellular matrix are early and persistent contributors to the development and progression of chronic renal disease and vascular disease. Border W. A., et al, *N. Engl. J. Med.,* 1994; 331(19), 1286-92. Further, TGF-β1 plays a role in the formation of fibronectin and plasminogen activator inhibitor-1, components of sclerotic deposits, through the action of smad3 phosphorylation by the TGF-β1 receptor ALK5. Zhang Y., et al, *Nature,* 1998; 394(6696), 909-13; Usui T., et al, *Invest. Ophthalmol. Vis. Sci.,* 1998; 39(11), 1981-9.

Progressive fibrosis in the kidney and cardiovascular system is a major cause of suffering and death and an important contributor to the cost of health care. TGF-β1 has been implicated in many renal fibrotic disorders. Border W. A., et al, *N. Engl. J. Med.,* 1994; 331(19), 1286-92. TGF-β1 is elevated in acute and chronic glomerulonephritis Yoshioka K., et al, *Lab. Invest.,* 1993; 68(2), 154-63, diabetic nephropathy Yamamoto, T., et al, 1993, *PNAS* 90, 1814-1818, allograft rejection, HIV nephropathy and angiotensin-induced nephropathy Border W. A., et al, *N. Engl. 5 J. Med.,* 1994; 331(19), 1286-92. In these diseases the levels of TGF-β1 expression coincide with the production of extracellular matrix. Three lines of evidence suggest a causal relationship between TGF-β1 and the production of matrix. First, normal glomeruli, mesangial cells and non-renal cells can be induced to produce extracellular-matrix protein and inhibit protease activity by exogenous TGF-β1 in vitro. Second, neutralizing antibodies against TGF-β1 can prevent the accumulation of extracellular matrix in nephritic rats. Third, TGF-β1 transgenic mice or in vivo transfection of the TGF-β1 gene into normal rat kidneys resulted in the rapid development of glomerulosclerosis. Kopp J. B., et al, *Lab. Invest.,* 1996; 74(6), 991 1003. Thus, inhibition of TGF-β1 activity is indicated as a therapeutic intervention in chronic renal disease.

TGF-β1 and its receptors are increased in injured blood vessels and are indicated in neointima formation following balloon angioplasty Saltis J., et al, *Clin. Exp. Pharmacol. Physiol.,* 1996; 23(3), 193-200. In addition TGF-β1 is a potent stimulator of smooth muscle cell ("SMC") migration in vitro and migration of SMC in the arterial wall is a contributing factor in the pathogenesis of atherosclerosis and restenosis. Moreover, in multivariate analysis of the endothelial cell products against total cholesterol, TGF-β receptor ALK5 correlated with total cholesterol (P<0.001) Blann A. D., et al, *Atherosclerosis,* 1996; 120(1-2), 221-6.

Furthermore, SMC derived from human atherosclerotic lesions have an increased ALK5/TGF-β type II receptor ratio. Because TGF-β1 is over-expressed in fibroproliferative vascular lesions, receptor-I variant cells would be allowed to grow in a slow, but uncontrolled fashion, while overproducing extracellular matrix components McCaffrey T. A., et al, Jr., *J. Clin.; Invest.,* 1995; 96(6), 2667-75. TGF-β1 was immunolocalized to non-foamy macrophages in atherosclerotic lesions where active matrix synthesis occurs, suggesting that non-foamy macrophages may participate in modulating matrix gene expression in atherosclerotic remodelling via a TGF-β-dependent mechanism. Therefore, inhibiting the action of TGF-β1 on ALK5 is also indicated in atherosclerosis and restenosis.

Liver fibrosis is the result of unbalanced wound healing response to chronic liver injury trigged by a number of agents, such as hepatitis B and hepatitis C virus, alcohol or drugs, and autoimmune diseases. Ultimately, liver fibrosis could lead to life-threatening cirrhosis and liver cancer (see review article by Gressner et al (2006) *J. Cell. Mol. Med.* 2006, 10(1): 76-99).

Several cellular signaling pathways are known to be altered upon chronic liver injury.

TGFβ signaling, its receptors and associated Smad-signaling proteins are well documented to be present in cell types involved in fibrogenesis. The circulating levels of TGFβ have been found to be elevated in a number of animal models of fibrotic diseases including liver fibrosis. Transgenic mice with overexpression of TGFβ1 develop fibrosis in multiple organs including liver, kidney, lungs and heart. It is apparent that an elevated TGFβ signaling is involved in all types of fibrotic diseases including liver fibrosis. This notion has been further validated in several studies using TGFβ inhibitors in fibrosis models. TGFβ mediates it signal by binding to two ser/thr kinase receptors, TGFβRII and ALK5. Expressing a dominant negative TGFβRII showed beneficial effects in a rat model of dimethylnitrosamine induced liver fibrosis (see Qi et al (1999) *Proc. Natl. Acad. Sci* 96: 2345-9 and Nakamura et al (2000) *Hepatology* 32: 247-55). Inhibiting TGFβ expression using an antisense approach also reduced liver fibrosis induced by bile duct ligation (see Arias et al (2003) *BMC Gastroenterol.* 3: 29). Recently, a small molecule inhibitor of ALK5, GW6604, when given therapeutically to rat, had significant effect in the treatment of dimethylnitrosamine induced liver fibrosis. It is quite remarkable that GW6604 prevented 40% of the death rate and inhibited extracellular matrix deposition by 60%, a key measurement for fibrosis. Importantly, no obvious side effects were noted during the 3 weeks treatment with GW6604 (see De Gouville et al (2005) *Br. J. Pharmacol.* 145: 166-77). Taken together these studies suggest that inhibiting TGFβ signaling could be an effective treatment for liver fibrotic diseases.

TGF-β1 is also indicated in wound repair. Neutralizing antibodies to TGF-β1 have been used in a number of models to illustrate that inhibition of TGF-β1 signalling is beneficial in restoring function after injury by limiting excessive scar formation during the healing process. For example, neutralizing antibodies to TGF-β1 and TGF-β2 reduced scar formation and improved the cytoarchitecture of the neodermis by reducing the number of monocytes and macrophages as well as decreasing dermal fibronectin and collagen deposition in rats Shah M., *J. Cell. Sci.,* 1995, 108, 985-1002. Moreover, TGF-β antibodies also improve healing of corneal wounds in rabbits Moller-Pedersen T., *Curr. Eye Res.,* 1998, 17, 736-747, and accelerate wound healing of gastric ulcers in the rat, Ernst H., *Gut,* 1996, 39, 172-175. These data strongly suggest that limiting the activity of TGF-β would be beneficial in many tissues and suggest that any disease with chronic elevation of TGF-β would benefit by inhibiting smad2 and smad3 signalling pathways.

TGF-β is also implicated in peritoneal adhesions Sand G. M., et al, *Wound Repair Regeneration,* November-December 1999, 7(6), 504-510. Therefore, inhibitors of ALK5 would be beneficial in preventing peritoneal and sub-dermal fibrotic adhesions following surgical procedures.

TGF-β is also implicated in photoaging of the skin (see Fisher G J. Kang S W. Varani J. Bata-Csorgo Z. Wan Y S. Data S. Voorhees J J., Mechanisms of photoaging and chronological skin ageing, *Archives of Dermatology,* 138(11):1462-1470, November 2002 and Schwartz E. Sapadin A N. Kligman L H. "Ultraviolet B radiation increases steady state mRNA levels for cytokines and integrins in hairless mouse skin-modulation by 25 topical tretinoin", *Archives of Dermatological Research,* 290(3):137-144, March 1998)

TGF-β signalling is also implicated in the development of pulmonary disorders, in particular pulmonary hypertension and pulmonary fibrosis (see Morrell N W, Yang X, Upton P D, Jourdan K B, Morgan N, Sheares K K, Trembath R C., Altered growth responses of pulmonary artery smooth muscle cells from patients with primary pulmonary hypertension to transforming growth factor-beta(1) and bone morphogenetic proteins. *Circulation.* August 2001 14; 104(7):790-5. Bhatt N, Baran C P, Allen J, Magro C, Marsh C B., Promising pharmacologic innovations in treating pulmonary fibrosis. *Curr Opin Pharmacol.* Apr. 28, 2006).

TGF-β1 levels are increased in animal models of pulmonary hypertension (Mata-Greenwood E, Meyrick B, Steinhorn R H, Fineman J R, Black S M. Alterations in TGF-beta1 expression in lambs with increased pulmonary blood flow and pulmonary hypertension. *Am. J. Physiol. Lung Cell Mol. Physiol.* July 2003; 285(1):L209-21). Other studies have suggested that pulmonary endothelial cell-derived TGF-β1 can stimulate the growth of pulmonary vascular smooth muscle cells which may underlie the enhanced muscularisation observed in the pulmonary vasculature of individuals with pulmonary hypertension (Sakao S, Taraseviciene-Stewart L, Wood K, Cool C D, Norbert V F. Apoptosis of pulmonary microvascular endothelial cells stimulates vascular smooth muscle cell growth. *Am. J. Physiol. Lung Cell Mol. Physiol. Apr.* 14, 2006). Therefore, inhibiting the action of TGF-β1 on ALK5 is indicated as a therapeutic intervention in pulmonary hypertension.

Additionally, dys-regulated TGF-β signalling has also been implicated in the development of idiopathic pulmonary fibrosis. Activation of ALK5 results in Smad3-activation and downstream modulation of the expression of genes involved in the fibrotic process such as plasminogen activator inhibitor-1, pro-collagen 3A1, and connective tissue growth factor. The levels of TGF-β1 and its downstream pro-fibrotic mediators have been demonstrated to be up-regulated in bronchoalveolar lavage taken from patients with idiopathic pulmonary fibrosis (Hiwatari N, Shimura S, Yamauchi K, Nara M, Hida W, Shirato K. Significance of elevated procollagen-III-peptide and transforming growth factor-beta levels of bronchoalveolar lavage fluids from idiopathic pulmonary fibrosis patients. *Tohoku J. Exp. Med.* February 1997; 181(2): 285-95) and in animal models of idiopathic pulmonary fibrosis (Westergren-Thorsson G, Hernnas J, Sarnstrand B, Oldberg A, Heinegard D, Malmstrom A. Altered expression of small proteoglycans, collagen, and transforming growth factor-beta 1 in developing bleomycin-induced pulmonary fibrosis in rats. *J. Clin. Invest.* August 1993; 92(2):632-7).

Transient over-expression of active TGF-β1 in murine lungs, using adenoviral vector-mediated gene transfer, resulted in progressive pulmonary fibrosis in wild-type mice, whereas no fibrosis was seen in the lungs of Smad3 knockout mice up to 28 days following TGF-β1 challenge (Khalil N, Parekh T V, O'Connor R N, Gold L I. Differential expression of transforming growth factor-beta type I and II receptors by pulmonary cells in bleomycin-induced lung injury: correlation with repair and fibrosis. *Exp. Lung. Res.* April-May 2002; 28(3):233-50. Thus, inhibition of TGF-β1 activation of ALK5 is also indicated for pulmonary fibrosis. TGF-beta 1 may also be implicated in tumors and hence the agents of the invention may be useful in the treatment of cancer, including prostate cancer, breast cancer, gastric cancer, angiogenesis, metastasis, tumors, e.g. in the treatment and/or prevention of tumor progression.

Activin signalling and overexpression of activin is linked to pathological disorders that involve extracellular matrix accumulation and fibrosis (e.g., Matsuse, T. et al., *Am. J. Respir Cell Mol. Biol.* 13:17-24 (1995); Inoue, S. et al., *Biochem. Biophys. Res. Comm.* 205:441-448 (1994); Matsuse, T. et al., *Am. J. Pathol.* 148:707-713 (1996); De Bleser et al., *Hepatology* 26:905-912 (1997); Pawlowski, J. E., et al., *J. Clin. Invest.* 100:639-648 (1997); Sugiyama, M. et al., *Gastroenterology* 114:550-558 (1998); Munz, B. et al., EMBO J. 18:5205-5215 (1999)), inflammatory responses (e.g., Rosendahl, A. et al., *Am. J. Respir Cell Mol. Biol.* 25:60-68 (2001), cachexia or wasting (Matzuk7 M. M. et al., *Proc. Natl. Acad. Sci. USA* 91:8817-8821 (1994); Coerver, K. A. et al., *Mol. Endocrinol.* 10:531 543 (1996); Cipriano, S. C. et al., *Endocrinology* 141:2319-2327 (2000)), diseases or pathological responses in the central nervous system (e.g., Logan, A. et al., *Eur. J. Neurosci.* 11:2367-2374 (1999); Logan, A. et al., *Exp. Neurol.* 159:504-510 (1999); Masliah, E. et al., *Neurochem. Int.* 39:393-400 (2001); De Groot, C. J. A. et al., *J. Neuropathol. Exp. Neural.* 58:174-187 (1999); John, G. R. et al., *Nat. Med.* 8:1115-1121 (2002)) and hypertension (e.g., Dahly, A. J. et al., *Am. J. Physiol. Regul. Integr Comp. Physiol.* 283: R757-767 (2002)). Studies have shown that TGF-β and activin can act synergistically to induce extracellular matrix production (e.g., Sugiyama, M. et al., *Gastroenterology* 114; 550-558 (1998)).

It follows, therefore, that inhibition of ALK5 and/or ALK4 phosphorylation of Smad2 and Smad3 by the agents of the invention can be useful to treat and prevent disorders that involve these signalling pathways.

Activin signalling is also implicated in the development of pulmonary disorders, in particular pulmonary hypertension and pulmonary fibrosis. For example, the expression of activin A in lung samples from patients with interstitial pulmonary fibrosis demonstrated strong expression of activin A on metaplastic epithelium, hyperplastic smooth muscle cells, desquamated cells, and alveolar macrophages. Pulmonary arteries from patients with primary or secondary pulmonary hypertension showed abundant immunoreactive activin A on smooth muscle cells. These findings suggest a potential role for this growth factor, activin A, in the pathogenesis of pulmonary tissue remodelling associated with interstitial pulmonary fibrosis and pulmonary hypertension (Matsuse T, Ikegami A, Ohga E, Hosoi T, Oka T, Kida K, Fukayama M, Inoue S, Nagase T, Ouchi Y, Fukuchi Y. Expression of immunoreactive activin A protein in remodelling lesions associated with interstitial pulmonary fibrosis. *Am. J. Pathol.* March 1996; 148(3):707-13). An increase in fibroblasts and associated connective tissue is a feature of pulmonary fibrosis and pulmonary hypertension. Activin A has been demonstrated to modulate human lung fibroblast (HFL1) activity, particularly with respect to proliferation and its differentiation into myofibroblast, thus activin A has potential effects on proliferation of lung fibroblast and its differentiation into myofibroblast, and may contribute to structural remodelling observed in pulmonary fibrosis and hypertension (Ohga E, Matsuse T, Teramoto S, Katayama H, Nagase T, Fukuchi Y, Ouchi Y. Effects of activin A on proliferation and differentiation of human lung fibroblasts. *Biochem. Biophys. Res. Commun.* Nov. 12, 1996; 228(2): 391-6). The induction of pulmonary fibrosis mediated by bleomycin challenge in rats results in the up-regulated expression of activin A in macrophages infiltrated in the lung, and was detected in fibroblasts accumulated in the fibrotic area. Administration of follistatin, an antagonist of activin signalling to bleomycin-treated rats significantly reduced the number of macrophages and neutrophils in bronchoalveolar lavage and reduced the protein content. Follistatin markedly reduced the number of infiltrating cells, ameliorated the destruction of lung architecture, and attenuated lung fibrosis (Aoki F, Kurabayashi M, Hasegawa Y, Kojima I. Attenuation of bleomycin-induced pulmonary fibrosis by follistatin. *Am. J. Respir. Crit. Care Med. Sep.* 15, 2005; 172(6): 713-20).

Therefore, inhibiting activin signalling via ALK4 inhibition may also be reasonably expected to be beneficial for the treatment of pulmonary fibrosis and pulmonary hypertension.

It has been demonstrated recently that reduction in TGF-β signalling, through its effector Smad3, enhances the mechanical properties and mineral concentration of the bone matrix, as well as the bone mass, enabling the bone to better resist fracture. These results suggest that reduction of TGF-β signalling could be considered as a therapeutic target to treat bone disorders. (Balooch G, et al. *Proc. Natl. Acad. Sci.* USA. Dec. 27, 2005; 102(52):18813-8). Thus, inhibition of TGF-β1 activation of ALK5 is also indicated for increasing mineral density strength and content of bone and may be utilized to treat a wide variety of conditions, including for example, osteopenia, osteoporosis, fractures and other disorders in which low bone mineral density are a hallmark of the disease.

Having regard to their inhibition of ALK-5 and/or ALK-4 receptors, agents of the invention are useful in the treatment of conditions mediated by the ALK-5 and/or ALK-4 receptors. Treatment in accordance with the invention may be symptomatic or prophylactic.

Therefore according to a further aspect, the invention provides the use of agents of the invention (another word used herein for compounds of the formula I, their salts or their solvents) for treating or preventing a disease or condition mediated by ALK-5 inhibition or ALK-4 inhibition, or their use in the preparation of a medicament for treating or preventing a disease or condition mediated by ALK-5 inhibition or ALK-4 inhibition, as well as to said agens for use in the treatment of said disease or condition.

Diseases or condition mediated by ALK-5 inhibition or ALK-4 inhibition include glomerulo-nephritis, diabetic nephropathy, lupus nephritis, hypertension-induced nephropathy, renal interstitial fibrosis, renal fibrosis resulting from complications of drug exposure, HIV-associated nephropathy, transplant necropathy, liver fibrosis due to all etiologies, hepatic dysfunction attributable to infections, alcohol-induced hepatitis, disorders of the biliary tree, pulmonary fibrosis, pulmonary hypertension, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub dermal adhesion, scleroderma, fibrosclerosis, progressive systemic sclerosis, dermatomyositis, polymyositis, arthritis, ulcers, impaired neurological function, male erectile dysfunction, Alzheimer's disease, Raynaud's syndrome, fibrotic cancers, tumor metastasis growth, radiation-induced fibrosis, thrombosis, and bone conditions such as osteopenia and osteoporosis, which are associated with increased calcium depletion or resorption or in which stimulation of bone formation and calcium fixation in the bone is desirable.

Diseases or conditions mediated by ALK-5 inhibition in particular include chronic renal disease, acute renal disease, wound healing, arthritis, osteoporosis, kidney disease, congestive heart failure, inflammatory or obstructive airways diseases, pulmonary hypertension, ulcers (including diabetic ulcers, chronic ulcers, gastric ulcers, and duodenal ulcers), ocular disorders, corneal wounds, diabetic nephropathy, impaired neuro-logical function, Alzheimer's disease, atherosclerosis, peritoneal and sub-dermal adhesion, any disease wherein fibrosis is a major component, including, but not limited to kidney fibrosis, lung fibrosis and liver fibrosis, for example, hepatitis B virus (HBV), hepatitis C virus (HCV), alcohol-induced hepatitis, haemochromatosis, primary biliary cirrhosis, restenosis, retroperitoneal fibrosis, mesenteric fibrosis, endometriosis, keloids, cancer, abnormal bone function, inflammatory disorders, scarring and photo-aging of the skin.

Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".) Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include adult/acute respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Preferably the disease or condition mediated by ALK-5 inhibition or ALK-4 inhibition is pulmonary hypertension, pulmonary fibrosis, liver fibrosis, muscular diseases, cancer or osteoporosis.

Pulmonary hypertension to be treated in accordance with the invention includes primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

Pulmonary hypertension to be treated in accordance with the invention is most particularly pulmonary hypertension associated with disorders of the respiratory system and/or hypoxemia, including chronic obstructive pulmonary disease, interstitial lung disease, sleep-disordered breathing, alveolar hypoventilation disorders, chronic exposure to high altitude, neonatal lung disease and alveolar-capillary dysplasia, but especially chronic obstructive pulmonary disease.

Lung fibrosis includes idiopathic pulmonary fibrosis in particular.

Compounds of the present may also be used to treat muscle diseases including muscular atrophies (e.g. disuse), muscular dystrophies (e.g. Duchenne's Muscle Dystrophy, Beckers Muscle Dystrophy, Limb-Girdle Muscle Dystrophy, Facioscapulohumeral Dystrophy), sarcopenia and cachexia.

Treatment of muscular diseases such as muscle atrophies and dystrophies is a largely unmet medical need. There are only few compounds approved for the use in assorted muscle disorders, mainly in the area of cancer-induced and HIV muscle wasting or cachexia, and a few more drugs are used off-label for these indications. In addition, most of these drugs only address the weight loss and do not specifically affect muscular growth and function. There is therefore a need for effective therapies to treat functional impairments associated with muscle diseases related to cachexia (e.g. in cancer, HIV and COPD), disuse atrophy, sarcopenia and dystrophy.

Myostatin, a member of the transforming growth factor β (TGFβ) family, is a key negative regulator of skeletal muscle mass. In double-muscle cattle and in a human body with skeletal muscle hypertrophy, different mutations in the myostatin gene were detected (McPherron et al (1997) *Nature* 387:83-90; Schuelke et al (2004) *N. Engl. J. Med.* 350:2682-2688). The important role of myostatin for skeletal muscle growth and disorders was confirmed in a wide variety of in vivo and in vitro studies. For example, muscle-specific over-expression of myostatin in mice causes loss of muscle mass (Reisz-Porszasz et al (2003) *AJP—Endo.* 285:876-888), whereas myostatin null mice have increased skeletal muscle mass and reduced body fat (Lin et al (2002) *Biochem. Biophys. Res. Comm.* 291: 701-706). In accordance systemic administration of myostatin induces cachexia (Zimmers et al (2002) *Science* 296:1486-1488), whereas inhibition of myostatin by, for example, the myostatin neutralizing antibody JA16 increases muscle mass and strength in wildtype and dystrophic mdx mice (Bogdanovich et al (2002) *Nature* 420: 418-421.2002; Wagner et al (2002) *Ann. Neurol.* 52: 832-836; Wolfman et al (2003) *Proc. Natl. Acad. Sci.* 100(26): 15842-15846). In addition, elevated myostatin levels have been observed in both experimental and clinical muscle atrophies such as in patients with Human Immunodeficiency Virus (HIV), cancer or liver cirrhosis as well as in sarcopenia of old age and under glucocorticoid-treatment (Ma et al (2003) *Am. J. Physiol. Endocrinol. Metab.* 285: E363-371; Gonzales-Cadavid et al (1998) *Proc. Natl. Acad. Sci.* 95: 14938-14943; see also Reisz-Porszasz et al (2003) *AJP—Endo.* 285:876-888 and Jespersen et al (2006) *Scand. J. Med. Sci. Sports.* 16: 74-82). These findings show the high potential of myostatin inhibitors as treatments for muscular atrophies and dystrophies.

The mode of action of myostatin is still under investigation. It is relatively well established that myostatin signals through Smad2/3 (Lee S. J. (2004) *Ann. Rev. Dev. Biol.* 20: 61-86). Moreover, mature myostatin has been shown to act via activin type IIb and activin receptor like kinase (ALK) receptors in adipocytes (Rebbarpragada et al (2003) *Mol. Cell. Biol.* 23: 7230-7242). However, respective findings in skeletal muscle cells are not described. Myostatin is believed to inhibit differentiation and cause atrophy via ALK signaling. Moreover, inhibition of ALK signaling promotes skMC differentiation and causes skMC hypertrophy.

Osteoporosis is a systemic skeletal disorder characterized by low bone mass and micro-architectural deterioration of bone tissue, with a consequent increase in bone fragility and susceptibility to fracture. The osteoporotic syndrome is multi faceted, encompassing primary disorders such as postmenopausal or age-related osteoporosis, and secondary conditions that accompany disease states or medications. The mechanical properties and composition of bone matrix, along with bone mass and architecture, are critical determinants of a bone's ability to resist fracture.

Thus in a further aspect the invention includes an agent of the invention for use as a pharmaceutical.

In a yet further aspect the invention includes a method for preventing or treating bone conditions which are associated with increased calcium depletion or resorption or in which stimulation of bone formation and calcium fixation in the bone is desirable in which an especially pharmaceutically) effective amount of an agent of the invention, or a pharmaceutically-acceptable and -cleavable ester, or acid addition salt thereof is administered to a patient in need of such treatment.

In a yet further aspect the invention includes a pharmaceutical composition for preventing or treating bone conditions which are associated with increased calcium depletion or resorption or in which stimulation of bone formation and calcium fixation in the bone is desirable comprising an agent of the invention, or a pharmaceutically-acceptable and -cleavable ester, or acid addition salt thereof, in admixture with a pharmaceutically acceptable excipient, diluent or carrier.

In a yet further aspect the invention includes the use of an agent of the invention in the manufacture of a medicament for the treatment or prevention of a bone condition.

The kinase activity of ALK5 is assessed by measuring radiolabelled phosphate [33P] incorporation in to the generic substrate, casein. The kinase domain of human ALK5 (amino acids 200-503) is fused to an N-terminal histidine tag. The kinase activity of ALK5 is rendered constitutive via point mutation at amino acid 204 (threonine to aspartate modification, ALK5 T204D) and the kinase construct is engineered to be expressed from a baculovirus expression construct in insect cells. The purified, recombinantly-expressed histidine-tagged ALK5 T204D protein is dissolved at 5.4 mg/ml in 50 mM Tris-HCl pH 8.0, 150 mM NaCl, 5 mM DTT. ALK5 T204D is dissolved to 2.5 µg/ml in assay buffer (Assay buffer: 20 mM Tris-HCl pH 7.4, 10 mM $MgCl_2$, 2 mM $MnCl_2$) on the day of use.

Test compounds and reference compounds are dissolved in assay buffer without DTT containing 5% (v/v) DMSO. Stock solutions of test and reference compounds are diluted in assay buffer with DTT (1.25 mM) containing 4.5% (v/v) DMSO. 10 µl of test or reference compound are added to the appropriate wells of 96 well U-bottomed plate. Total enzyme activity is determined by measuring ALK5 T204D activity in the absence of ALK5 kinase inhibitor reference compounds. Non-specific binding (NSB) is determined by measuring the activity of ALK5 T204D in the presence of ALK5 kinase inhibitor reference compounds. 10 µl of dephosphorylated casein stock solution (dephosphorylated casein is dissolved in $ddH_2O$ at 20 mg/ml) is added per well (200 µg/well final assay concentration). 20 µl of ALK5 T204D (2.5 µg/ml solution) is added per well (50 ng/well final assay concentration). The plates are left to incubate at room temperature for 10 minutes.

10 µl of ATP mix is added to the well to initiate the reaction (0.66 nM [$^{33}$P]ATP/1 µM unlabelled ATP/well final assay concentration). The ATP mix is prepared as follows, unlabelled ATP (3 mM) is dissolved in $ddH_2O$ and pH adjusted to 7.4. The stock concentration of [$^{33}$P]ATP is 10 µCi/µl. The appropriate volume of [$^{33}$P]ATP is added to unlabelled ATP solution such that the final assay concentration per well is 0.1 µCi. Following addition of the ATP mix, the plates are incubated at room temperature for 50 minutes. The kinase reaction is terminated by the addition of 50 µL Stop Buffer (20 mM Tris-HCl pH 7.4, 10 mM EDTA).

75 μl/well from the reaction plate is transferred to a Multiscreen-IP plate (MultiScreen-IP plates are prepared by added 50 μL of 70% (v/v) ethanol per well and incubated for 5 minutes at room temperature. The ethanol is removed by aspiration via a MultiScreen HTS Vaccum Manifold unit (Millipore, Cat no: MSVMHT500). The plates are washed twice by adding 200 μl/well ddH$_2$O). The MultiScreen-IP plate is incubated at room temperature for 30 minutes to allowing binding of casein to the plate. The MultiScreen-IP plates are washed three times by adding 200 μl/well 100 mM phosphoric acid solution and the gasket is carefully removed from the back of the MultiScreen-IP plate and the plate dried in the oven for 30 minutes. The MultiScreen-IP plate is backsealed, 50 μL of Microscint™20 is added, then the plates are topsealed and radiolabelled casein detected and quantified on a TopCount™ plate-reader using the $^{33}$P scintillation protocol.

Compounds according to the invention, in this assay, show an inhibition of ALK-5 with an IC50 in the range from 1 to 10,000 nM, preferably from 2 to 2000 nM.

Using the test system mentioned above, experimentally the IC50 data shown in the Examples can be found.

The agents of the invention are also useful as co-therapeutic agents for use in combination with other drug substances such as anti-inflammatory, bronchodilatory, antihistamine, decongestant or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with one or more other drug substances in a fixed pharmaceutical composition or it may be administered separately, before, simultaneously with or after the other drug substance(s).

Such anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 [Novartis] (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935, WO 04/26248 and WO 05/05452; LTB4 antagonists such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700 and WO 04/108720; LTD4 antagonists such as montelukast, praniukast, zafirlukast, accolate, SR2640, Wy-48,252, ICI 198615, MK-571, LY-171883, Ro24-5913 and L-648051; Dopamine receptor agonists such as cabergoline, bromocriptine, ropinirole and 4-hydroxy-7-[2-[[2-[[3-(2-phenylethoxy)-propyl]sulfonyl]ethyl]amino]ethyl]-2(3H)-benzothiazolone and pharmaceutically acceptable salts thereof (the hydrochloride being Viozan®—AstraZeneca); PDE4 inhibitors such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), GRC 3886 (Oglemilast, Glenmark), WO 92/19594, WO 93/19749, WO 93/19750, WO 93/19751, WO 99/16766, WO 01/13953, WO 03/104204, WO 03/104205, WO 04/000814, WO 04/000839 and WO 04/005258 (Merck), WO 04018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607, WO 04/037805, WO 04/063197, WO 04/103998, WO 04/111044, WO 05012252, WO 05012253, WO 05/013995, WO 05/030212, WO 05/030725, WO 05/087744, WO 05/087745, WO 05/087749 and WO 05/090345 as well as those described in WO 98/18796 and WO 03/39544. A2a agonists such as those described in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; and A2b antagonists such as those described in WO 02/42298 and WO 03/042214.

Such bronchodilatory drugs include beta-2 adrenoceptor agonists. Suitable beta-2 adrenoceptor agonists include albuterol (salbutamol), metaproterenol, terbutaline, salmeterol, fenoterol, procaterol, and especially, formoterol, carmoterol, GSK159797 and pharmaceutically acceptable salts thereof, and compounds (in free or salt or solvate form) of formula I of WO 0075114, which document is incorporated herein by reference, preferably compounds of the Examples thereof, especially a compound of formula

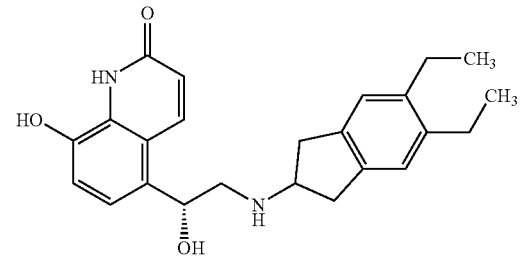

and pharmaceutically acceptable salts thereof, as well as compounds (in free or salt or solvate form) of formula I of WO 04/16601 or of formula I of WO 04/087142. Further suitable β-2-adrenoreceptor agonists include compounds, such as those described in and also compounds of EP 147719, EP 1440966, EP 1460064, EP 1477167, EP 1574501, JP 05025045, JP 2005187357, US 2002/0055651, US 2004/0242622, US 2004/0229904, US 2005/0133417, US 2005/5159448, US 2005/5159448, US 2005/171147, US 2005/182091, US 2005/182092, US 2005/209227, US 2005/256115, US 2005/277632, US 2005/272769, US 2005/239778, US 2005/215542, US 2005/215590, US 2006/19991, US 2006/58530, WO 93/18007, WO 99/64035, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, WO 04/087142, WO 04/89892, WO 04/108675, WO 04/108676, WO 05/33121, WO 05/40103, WO 05/44787, WO 05/58867, WO 05/65650, WO 05/66140, WO 05/70908, WO 05/74924, WO 05/77361, WO 05/90288, WO 05/92860, WO 05/92887, WO 05/90287, WO 05/95328, WO 05/102350, WO 06/56471, WO 06/74897 or WO 06/8173.

Such bronchodilatory drugs also include other anticholinergic or antimuscarinic agents, in particular ipratropium bromide, oxitropium bromide, tiotropium salts, glycopyrrolate, CHF 4226 (Chiesi) and SVT-40776, but also those described in EP 424021, U.S. Pat. No. 3,714,357, U.S. Pat. No. 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/18422, WO 04/05285, WO 04/96800, WO 05/77361 and WO 06/48225.

Suitable dual anti-inflammatory and bronchodilatory drugs include dual beta-2 adrenoceptor agonist/muscarinic antagonists such as those disclosed in US 2004/0167167, US 2004/0242622, US 2005/182092, US 2005/256114, US 2006/35933, WO 04/74246, WO 04/74812, WO 04/89892 and WO 06/23475.

Suitable antihistamine drug substances include cetirizine hydrochloride, levocetirizine, acetaminophen, clemastine fumarate, promethazine, loratidine, desloratidine, diphenhydramine and fexofenadine hydrochloride, activastine, astemizole, azelastine, dimetinden, ebastine, epinastine, levocabastine, mizolastine and tefenadine as well as those disclosed in WO 03/099807, WO 04/026841 and JP 2004107299.

According to a further embodiment of the invention, the agents of the invention may be employed as adjunct or adjuvant to other therapy, e.g. a therapy using a bone resorption inhibitor, for example as in osteoporosis therapy, in particular a therapy employing calcium, a calcitonin or an analogue or derivative thereof, e.g. salmon, eel or human calcitonin, a steroid hormone, e.g. an estrogen, a partial estrogen agonist or estrogen-gestagen combination, a SERM (Selective Estrogen Receptor Modulator) e.g. raloxifene, lasofoxifene, TSE-424, FC1271, Tibolone (Livial A), vitamin D or an analog thereof or PTH, a PTH fragment or a PTH derivative e.g. PTH (1-84), PTH (1-34), PTH (1-36), PTH (1-38), PTH (1-31) NH2 or PTS 893.

The agents of the invention may further be employed in combination with human insulin-like growth factor1 or IGF1, however formulated or stabilized, such as IPLEX™ as developed by Insmed Inc or as described in US 2006/0166328.

In accordance with the foregoing, the present invention also provides a method for the treatment of an obstructive or inflammatory airways disease which comprises administering to a subject, particularly a human subject, in need thereof an agent of the invention, or a pharmaceutically acceptable salt or solvate thereof, as hereinbefore described. In another aspect, the invention provides an agent of the invention, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases. In particular, the agents of the invention may be delivered as an inhalable formulation for the treatment of COPD and asthma.

In a further aspect, the invention also provides a pharmaceutical composition comprising an agent of the invention in free form or in the form of a pharmaceutically acceptable salt or solvate thereof, optionally together with a pharmaceutically acceptable diluent or carrier therefore. Such compositions may be prepared using conventional diluents or excipients and techniques known in the galenic art.

The formulations may be parenteral compositions, e.g. for i.v., i.p., i.m. or other injection, or for infusion, for topical or transdermal administration, or for enteral administration, e.g. for oral, nasal or rectal administration, e.g. capsules, slozenges, powders, liquid oral formulations (e.g. drink solutions, dispersions, syrups or pastes), tablets, dragets, powders, inhalation products, suppositories or the like.

Thus oral dosage forms may include tablets and capsules. Formulations for topical administration may take the form of creams, ointments, gels or transdermal delivery systems, e.g. patches.

The dosage of the active ingredient depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy requires a regimen based on the kinetics of the drug's availability to target sites. This involves a consideration of the distribution, equilibrium, and elimination of a drug.

The dose of a compound of the formula I or a pharmaceutically acceptable salt thereof to be administered to warm-blooded animals, for example humans of approximately 70 kg body weight, is preferably from approximately 0.5 mg to approximately 10 g, more preferably from approximately 0.7 mg to approximately 7 g per person per day, divided preferably into 1 to 3 single doses which may, for example, be of the same size, if not mentioned otherwise. Usually, children receive half of the adult dose.

The present pharmaceutical compositions, which may, if desired, comprise other pharmacologically active substances, are prepared in a manner known per se, for example by means of conventional mixing, granulating, confectionning, dissolving or lyophilising processes, and comprise approximately from 1% to 99% by weight, especially from approximately 1% to approximately 60%, active ingredient(s).

Pharmaceutical compositions for enteral or parenteral administration are e.g. those in dosage unit forms such as dragees, tablets, capsules or suppositories, as well as ampoules, vials, pre-filled syringes.

For example, pharmaceutical compositions for oral administration can be obtained by combining the active ingredient with solid carriers, optionally granulating a resulting mixture and processing the mixture or granulate, if desired or necessary after the addition of suitable excipients, to tablets or dragee cores.

Suitable carriers are in particular fillers such as sugar, for example lactose, saccharose, mannitol or sorbitol, cellulose preparations and/or calcium phosphates, e.g. tricalcium phosphate or calcium biphosphate, and also binders such as starch pastes, e.g. maize, corn, rice or potato starch, gelatin, tragacanth, methyl cellulose and/or polyvinylpyrrolidone, and/or, if desired, disintegrators, such as the abovementioned starches, also carboxymethyl starch, crosslinked polyvinylpyrrolidone, agar, alginic acid or a salt thereof such as sodium alginate. Excipients are in particular glidants and lubricants, for example silica, talcum, stearic acid or salts thereof such as magnesium stearate or calcium stearate, and/or polyethylene glycol. Dragee cores are provided with suitable coatings which can be resistant to gastric juices, using inter alia concentrated sugar solutions which may contain gum arabic, talcum, polyvinylpyrrolidone, polyethylene glycol and/or titanium dioxide, shellac solutions in suitable organic solvents or mixtures of solvents or, for the preparation of coatings which are resistant to gastric juices, solutions of suitable cellulose preparations such as acetyl cellulose phthalate or hydroxypropyl methyl cellulose phthalate. Dyes or pigments can be added to the tablets or dragee coatings, for example to identify or indicate different doses of active ingredient.

Further pharmaceutical compositions for oral administration are dry-filled capsules made of gelatin or hypromellose and also soft sealed capsules consisting of gelatin and a plasticiser such as glycerol or sorbitol. The dry-filled capsules can contain the active ingredient in the form of granules, for example in admixture with fillers such as lactose, binders such as starches, and/or glidants such as talcum or magnesium stearate, and optionally stabilisers. In soft capsules, the active ingredient is preferably dissolved or suspended in a suitable liquid, such as a fatty oil, paraffin oil or a liquid polyethylene glycol, to which a stabiliser can also be added.

Suitable pharmaceutical compositions for rectal administration are e.g. suppositories, which consist of a combination of the active ingredient with a suppository base. Examples of suitable suppository bases are natural or synthetic triglycerides, paraffin hydrocarbons, polyethylene glycols and higher alkanols. It is also possible to use gelatin rectal capsules which contain a combination of the active ingredient with a base material. Suitable base materials are e.g. liquid triglycerides, polyethylene glycols and paraffin hydrocarbons.

Particularly suitable dosage forms for parenteral administration are aqueous solutions of an active ingredient in water-soluble form, for example a water-soluble salt. The solution may be adjusted with inorganic or organic acids or bases to a physiologically acceptable pH value of about pH 4-9 or most preferably of about 5.5-7.5. The solutions further may be made isotonic with inorganic salts like sodium chloride, or organic compounds like sugars, sugar alcohols, or amino acids, most preferably with mannitol or glycerol. Suitable compositions are also suspensions of the active ingredient, such as corresponding oily injection suspensions, for which there are used suitable lipophilic solvents or vehicles such as fatty oils, for example sesame oil, or synthetic fatty acid esters, for example ethyl oleate or triglycerides, or aqueous injection suspensions which contain substances which increase the viscosity, for example sodium carboxymethyl cellulose, sorbitol and/or dextran, and optionally also stabilisers.

Compositions for inhalation may comprise aerosol or other atomizable formulations or dry powder formulations.

Where the inhalable form of the active ingredient is an aerosol composition, the inhalation device may be an aerosol vial provided with a valve adapted to deliver a metered dose, such as 10 to 100 µl, e.g. 25 to 50 µl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 µl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042, WO 97/20589 (including the CERTIHALER™ device), WO 97/30743 (including the TWISTHALER™ device) and WO 05/37353 (including the GYROHALER™ device).

The invention also includes (A) an agent of the invention in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practicing the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The invention preferably relates to a compound of the formula I in free or salt or solvate form, wherein $T_1$ is a 4- to 10-membered heterocyclic group bound to the rest of the molecule via a ring carbon atom and unsubstituted or independently substituted at one, two or three positions by $R_1$, $C_1$-$C_8$-alkoxy, $C_3$-$C_{10}$-cycloalkyl, $C_1$-$C_8$-alkylthio, halo, halo-$C_1$-$C_8$-alkyl, amino, $C_1$-$C_8$-alkylamino, di($C_1$-$C_8$-alkyl)amino, cyano, oxo, hydroxy, carboxy or nitro;

$T_2$ is a 4- to 10-membered heterocyclic group bound to the rest of the molecule via a ring carbon atom and unsubstituted or independently substituted at one, two or three positions by $R_1$, $R_2$, $R_3$, $C_1$-$C_8$-alkoxy, halo, halo-$C_1$-$C_8$-alkyl, amino, —C(=O)NR$_4$R$_5$, —NH(C=O)R$_1$ or —NH(C=O)—C$_1$-C$_8$-alkyl-NR$_4$R$_5$;

$R_1$ is $C_1$-$C_8$-alkyl, $C_2$-$C_8$-alkenyl or $C_2$-$C_8$-alkynyl unsubstituted or independently substituted at one, two or three positions by hydroxy, amino, $C_1$-$C_8$-alkylamino, di($C_1$-$C_8$-alkyl)amino or $C_1$-$C_8$-alkanoylamino;

$R_2$ is $C_6$-$C_{12}$-aryl or $C_4$-$C_{10}$-cycloalkenyl, each of which is unsubstituted or independently substituted at one, two or three positions by halo, hydroxy, $R_1$, $R_3$, $R_4R_5N$—$C_1$-$C_8$-alkyl, $R_3$-$C_1$-$C_8$-alkyl, —O—$R_1$, —C(=O)—$R_3$;

$R_3$ is a 4- to 10-membered heterocyclic group bound via a carbon atom or, if it comprises a ring nitrogen not bound to a double bond, via a ring nitrogen or a ring carbon atom, unsubstituted or independently substituted at one, two or three positions by halo, hydroxyl or —$R_1$;

$R_4$ and $R_5$ are independently hydrogen, —$R_1$, $C_1$-$C_8$-alkylamino, di($C_1$-$C_8$-alkyl)amino, $C_1$-$C_8$-alkylamino-$C_1$-$C_8$-alkyl, di($C_1$-$C_8$-alkyl)amino-$C_1$-$C_8$-alkyl, —C(=O)—$R_1$ or $R_3$;

$T_3$ is H, R1, OH or $NH_2$, especially H; and

X is either N or CH;

with the proviso that if X is CH, then $T_2$ is a 4- or 6- to 10-membered heterocyclic group bound to the rest of the molecule via a ring carbon atom and unsubstituted or independently substituted at one, two or three positions by $R_1$, $R_2$, $R_3$, $C_1$-$C_8$-alkoxy, halo, halo-$C_1$-$C_8$-alkyl, amino, —C(=O)$NR_4R_5$, —NH(C=O)$R_1$ or —NH(C=O)—$C_1$-$C_8$-alkyl-$NR_4R_5$.

More preferably, the invention relates to a compound of the formula I wherein $T_1$ is pyridinyl bound via a ring carbon atom that is unsubstituted or substituted with $C_1$-$C_8$-alkyl;

$T_2$ is pyridinyl bound via a carbon atom that is unsubstituted or substituted by $C_1$-$C_8$-alkyl, cylcohexenyl, phenyl that is itself unsubstituted or substituted by one to three substituents independently selected from the group consisting of $C_1$-$C_8$-alkyl, hydroxyl, $C_1$-$C_8$-alkoxy, hydroxyl-$C_1$-$C_8$-alkyl, amino-$C_1$-$C_8$-alkyl, mono- or di-($C_1$-$C_8$-alkyl)-amino-$C_1$-$C_8$-alkyl, morpholino, thiomorpholine, S-mono- or S,S-dioxothiomorpholino, halo, piperazinyl-$C_1$-$C_8$-alkyl, N—$C_1$-$C_8$-alkyl-piperazinyl-$C_1$-$C_8$-alkyl, piperazinyl, N—$C_1$-$C_8$-alkyl-piperazinyl, pyrrolidinyl, piperidinyl, piperazincarbonyl (piperazin-C(=O)—) and N—$C_1$-$C_8$-piperazincarbonyl; $C_1$-$C_8$-alkoxy, $C_1$-$C_8$-alkanoyl-amino, hydroxyl-$C_1$-$C_8$-alkanoyl-amino, amino-$C_1$-$C_8$-alkanoyl-amino, mono- or di-($C_1$-$C_8$-alkyl)-amino-$C_1$-$C_8$-alkanoyl-amino, $C_1$-$C_8$-alkanoylyl-amino-$C_1$-$C_8$-alkanoyl-amino, carbamoyl, N—$C_1$-$C_8$-alkyl-carbamoyl, N-(hydroxyl-$C_1$-$C_8$-alkyl)-carbamoyl, N-(mono- or di-($C_1$-$C_8$-alkyl)amino-$C_1$-$C_8$-alkyl)-carbamoyl, N—(N'—$C_1$-$C_8$-piperazinyl)-$C_1$-$C_8$-alkyl-carbamoyl, piperidinyl, hydroxyl-piperidinyl, piperazinyl, N—$C_1$-$C_8$-alkyl-piperazinyl, morpholinyl, thiomorpholinyl, S-mono- or S,S-dio-oxo-thiomorpholinyl or by pyridinyl, or is indolyl, isoindolyl or preferably quinolinyl or isoquinolinyl, $T_3$ is hydrogen and X is CH or N, a (preferably pharmaceutically acceptable) salt thereof, and/or a solvate thereof.

Especially, the invention relates to a compound of the formula I in free or salt or solvate form, wherein $T_1$ is pyridin-2-yl or 6-methyl-pyridin-2-yl, $T_2$ is pyridin-3-yl, 4-methyl-pyridin-3-yl, 5-(cyclohex-1-enyl)-pyridin-3-yl, 5-(2-methyl-phenyl)-pyridin-3-yl, 5-(3-hydroxyphenyl)-pyridin-3-yl, 5-(4-methoxy-phenyl)-pyridin-3-yl, 5-(3-methoxy-phenyl)-pyridin-3-yl, 5-(2-methoxy-phenyl)-pyridine-3-yl, 5-(4-hydroxymethyl-phenyl)-pyridin-3-yl, 5-(3-hydroxymethyl-phenyl)-pyridin-3-yl, 5-(4-aminomethyl-phenyl)-pyridin-3-yl, 5-(3-aminomethyl-phenyl)-pyridin-3-yl, 5-[4-(N-methylamino-methyl)-phenyl]-pyridin-3-yl, 5-[3-(N-methylamino-methyl)-phenyl]-pyridin-3-yl, 5-[4-(N,N-dimethylaminomethyl)-phenyl]-pyridin-3-yl, 5-[3-(N,N-dimethylaminomethyl)-phenyl]-pyridin-3-yl 5-(4-morpholino-phenyl)-pyridin-3-yl, 5-(3-morpholino-phenyl)-pyridin-3-yl, 5-(4-fluoro-phenyl)-pyridin-3-yl, 5-(2-fluoro-phenyl)-pyridin-3-yl, 5-(2-chloro-phenyl)-pyridin-3-yl, 5-[4-(4-methyl-piperazin-1-ylmethyl)-phenyl]-pyridin-3-yl, 5-[3-(4-methyl-piperazin-1-ylmethyl)-phenyl]-pyridin-3-yl, 5-[4-(4-isopropyl-piperazin-1-ylmethyl)-phenyl]-pyridin-3-yl

[3-(4-isopropyl-piperazin-1-ylmethyl)-phenyl]-pyridin-3-yl,

5-[4-(4-methyl-piperazin-1-yl)-phenyl]-pyridin-3-yl, 5-(3-pyrrolidin-1-yl-phenyl)-pyridin-3-yl, 5-(4-piperidin-1-yl-phenyl)-pyridin-3-yl, 5-[4-(4-methyl-piperazin-1-yl)-phenyl]-pyridin-3-yl, 5-[4-(4-isopropyl-piperazin-1-yl)-phenyl]-pyridin-3-yl, 5-[4-(piperazin-1-yl-C(=O))-phenyl]-pyridin-3-yl, 5-[3-(piperazin-1-yl-C(=O))-phenyl]-pyridin-3-yl, 5-[4-(4-methyl-piperazin-1-yl-C(=O))-phenyl]-pyridin-3-yl, 5-[3-(4-methyl-piperazin-1-yl-C(=O))-phenyl]-pyridin-3-yl, 5-methoxy-pyridin-3-yl, 5-ethoxy-pyridin-3-yl, 5-isopropoxy-pyridin-3-yl, 5-bromo-pyridin-3-yl, 5-(propionylamino)-pyridin-3-yl, 5-[(3-hydroxy-propionyl)-amino]-pyridin-3-yl, 5-[(4-amino-butyryl)-amino]-pyridin-3-yl, 5-[(3-amino-propionyl)-amino]-pyridin-3-yl, 5-[(4-dimethylamino-butyryl)-amino]-pyridin-3-yl, 5-[(3-dimethylamino-propionyl)-amino]-pyridin-3-yl, 5-[(4-acetylamino-butyryl)-amino]-pyridin-3-yl, 5-[(3-acetylamino-propionyl)-amino]-pyridin-3-yl, 5-(N-ethyl-carbamoyl)-pyridin-3-yl, 5-[N-(3-hydroxy-propyl)-carbamoyl]-pyridin-3-yl, 5-{N-[3-(N',N'-dimethylamino)-propyl]-carbamoyl}-pyridin-3-yl, 5-{N-[2-(N',N'-dimethylamino)-ethyl]-carbamoyl}-pyridin-3-yl, 5-{N-[3-(4-methyl-piperazin-1-yl)-propyl]-carbamoyl}-pyridin-3-yl, 5-(piperidin-1-yl)-pyridin-3-yl, 5-morpholino-pyridin-3-yl, 5-(4-hydroxy-piperidin-1-yl)-pyridin-3-yl, 5-(4-methylpiperazin-1-yl)-pyridin-3-yl,

[3,4']bipyridin-5-yl, [3,3']bipyridin-5-yl, or quinolin-3-yl, isoquinolin-4-yl, $T_3$ is hydrogen and X is CH or N, a (preferably pharmaceutically acceptable) salt thereof, and/or a solvate thereof.

Further preferred embodiments of the invention are given in the claims, which are incorporated into the present description by reference.

Especially preferred compounds of the present invention include compounds of formula I as mentioned in the examples, as well as solvates and/or salts thereof.

Where the preferred compounds of the formula I, their salts and/or their solvates are mentioned, also their use, the compounds for use or a method of treatment comprising the use of the compounds or other uses and methods mentioned herein employing such one or more preferred compounds of the formula I, their salts and/or their solvates, is included.

The invention is illustrated by the following Examples which do not limit the scope of the invention.

EXAMPLES

Especially preferred compounds of the present invention include compounds of formula X

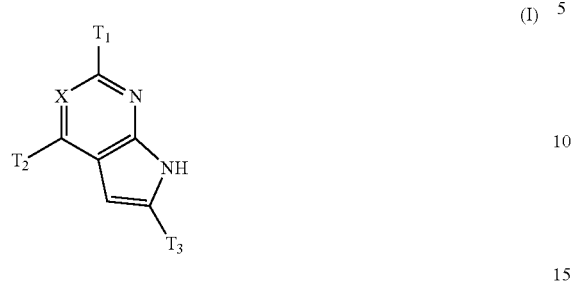

(I)

where $T_1$, $T_2$, $T_3$ and X are as shown in Table I below. The method of preparation being described hereinafter.

TABLE 1

| Ex. | T1 | T2 | T3 | X | MH+ | IC$_{50}$ (μM) | Route |
|---|---|---|---|---|---|---|---|
| 1 | 2-pyridyl | 3-pyridyl | H | N | 274 | 1.179 | A |
| 2 | 6-methyl-2-pyridyl | 3-pyridyl | H | N | 288 | 0.380 | A |
| 3 | 6-methyl-2-pyridyl | 5-methoxy-3-pyridyl | H | N | 318 | 0.130 | A |
| 4 | 6-methyl-2-pyridyl | 5-phenyl-3-pyridyl | H | N | 364 | 0.034 | A |
| 5 | 6-methyl-2-pyridyl | 5-(4-methoxyphenyl)-3-pyridyl | H | N | 394 | 0.115 | A |
| 6 | 6-methyl-2-pyridyl | 5-(3-methoxyphenyl)-3-pyridyl | H | N | 394 | 0.032 | A |
| 7 | 6-methyl-2-pyridyl | 5-(4-fluorophenyl)-3-pyridyl | H | N | 382 | 0.045 | A |

TABLE 1-continued
| Ex. | T1 | T2 | T3 | X | MH+ | IC$_{50}$ (μM) | Route |
|---|---|---|---|---|---|---|---|
| 8 | 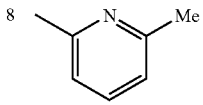 | 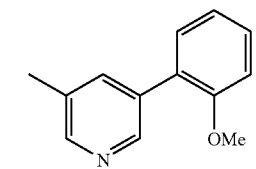 | H | N | 394 | 0.478 | A |
| 9 | 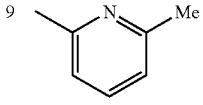 | 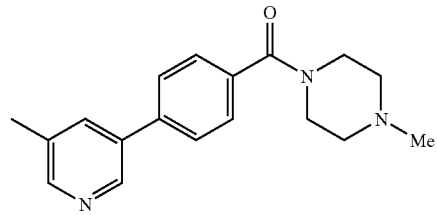 | H | N | 490 | 0.013 | C |
| 10 | 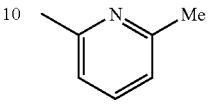 | 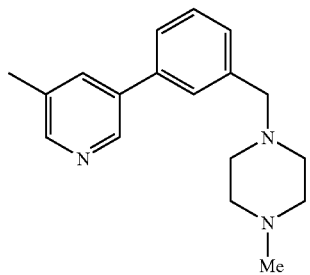 | H | N | 476 | 0.050 | A |
| 11 | 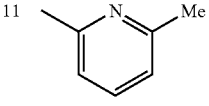 | 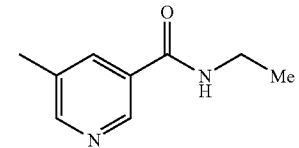 | H | N | 359 | 0.367 | D |
| 12 | 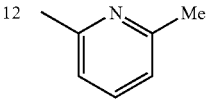 | 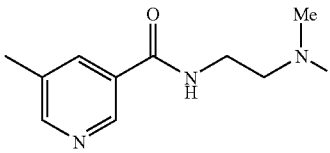 | H | N | 402 | 0.345 | D |
| 13 | 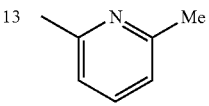 | 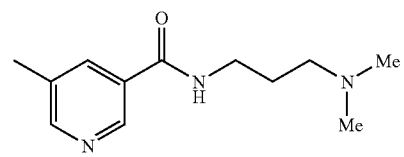 | H | N | 416 | 0.177 | D |
| 14 | 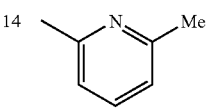 | 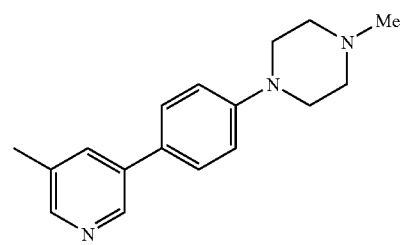 | H | N | 462 |  | C |

TABLE 1-continued
| Ex. | T1 | T2 | T3 | X | MH+ | IC$_{50}$ (µM) | Route |
|---|---|---|---|---|---|---|---|
| 15 | 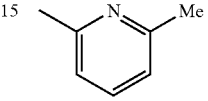 | 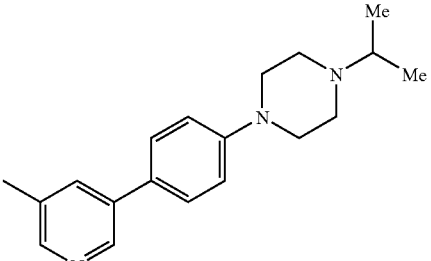 | H | N | 490 | 0.160 | C |
| 16 | 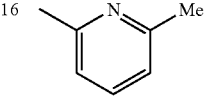 | 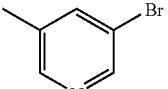 | H | N | 366/368 | 1.81 | B |
| 17 | 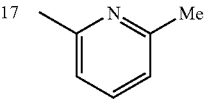 | 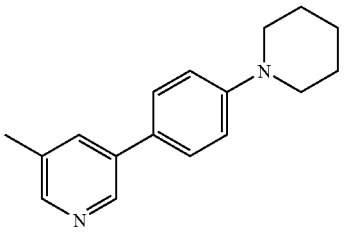 | H | N | 447 | 0.929 | C |
| 18 | 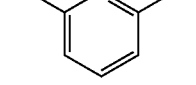 | 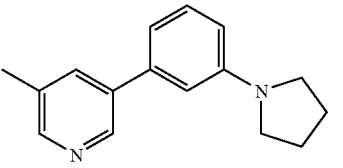 | H | N | 433 | 0.172 | C |
| 19 | 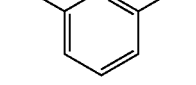 | 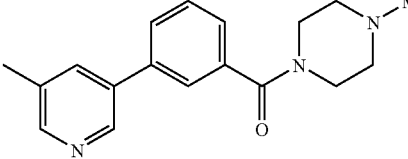 | H | N | 490 | | C |
| 20 | 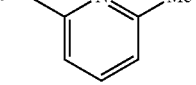 | 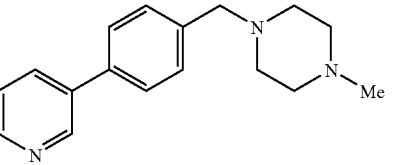 | H | N | 476 | 0.045 | C |
| 21 | 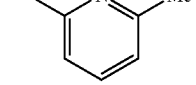 | 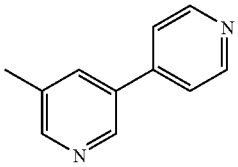 | H | N | 365 | 0.084 | C |
| 22 | 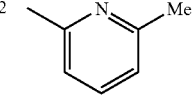 | 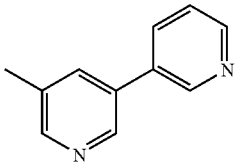 | H | N | 365 | 0.044 | C |

TABLE 1-continued

| Ex. | T1 | T2 | T3 | X | MH+ | IC$_{50}$ (μM) | Route |
|---|---|---|---|---|---|---|---|
| 23 | 2,6-dimethylpyridin-3-yl | 5-(3-hydroxyphenyl)pyridin-3-yl | H | N | 380 | 0.014 | C |
| 24 | 2,6-dimethylpyridin-3-yl | 5-(2-fluorophenyl)pyridin-3-yl | H | N | 382 | 0.034 | C |
| 25 | 2,6-dimethylpyridin-3-yl | 5-[(3-(4-methylpiperazin-1-yl)propyl)carbamoyl]pyridin-3-yl | H | N | 471 | 0.223 | D |
| 26 | 2,6-dimethylpyridin-3-yl | 5-[(3-hydroxypropyl)carbamoyl]pyridin-3-yl | H | N | 389 | 0.465 | D |
| 27 | 2,6-dimethylpyridin-3-yl | 5-(propanoylamino)pyridin-3-yl | H | N | 359 | 0.723 | A |
| 28 | 2,6-dimethylpyridin-3-yl | quinolin-3-yl | H | N | 338 | 0.184 | A |
| 29 | 2,6-dimethylpyridin-3-yl | isoquinolin-4-yl | H | N | 338 | 0.011 | A |
| 30 | 2,6-dimethylpyridin-3-yl | 5-[(4-(dimethylamino)butanoyl)amino]pyridin-3-yl | H | N | 416 | 0.064 | A |
| 31 | 2,6-dimethylpyridin-3-yl | 5-[(3-(dimethylamino)propanoyl)amino]pyridin-3-yl | H | N | 402 | 0.085 | A |

TABLE 1-continued
| Ex. | T1 | T2 | T3 | X | MH+ | IC$_{50}$ (μM) | Route |
|---|---|---|---|---|---|---|---|
| 32 | 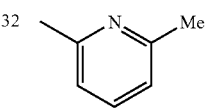 | 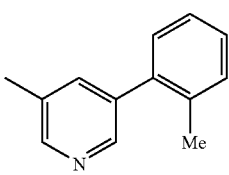 | H | N | 378 | 0.762 | C |
| 33 | 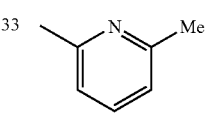 | 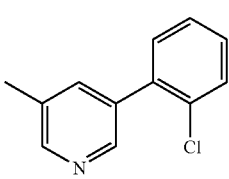 | H | N | 398 | 0.090 | C |
| 34 | 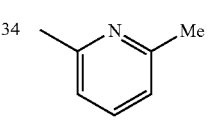 | 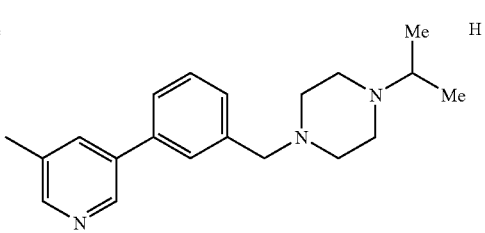 | H | N | 504 | 0.051 | C |
| 35 | 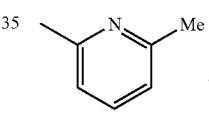 | 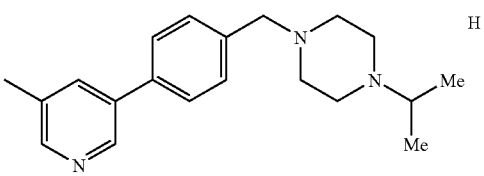 | H | N | 504 | 0.044 | C |
| 36 | 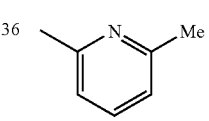 | 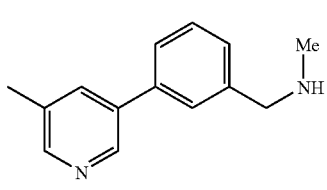 | H | N | 407 | 0.008 | C |
| 37 | 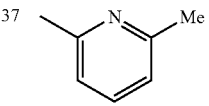 | 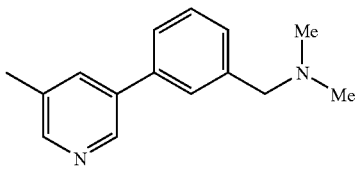 | H | N | 421 | 0.033 | C |
| 38 | 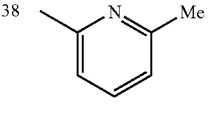 | 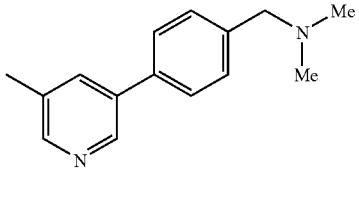 | H | N | 421 | 0.012 | C |
| 39 | 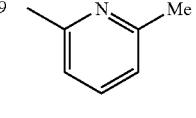 | 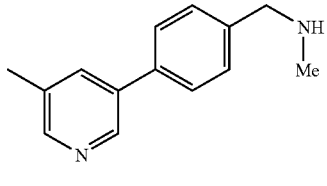 | H | N | 407 | 0.006 | E |

TABLE 1-continued
| Ex. | T1 | T2 | T3 | X | MH+ | IC$_{50}$ (μM) | Route |
|---|---|---|---|---|---|---|---|
| 40 | 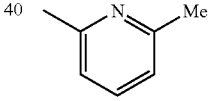 | 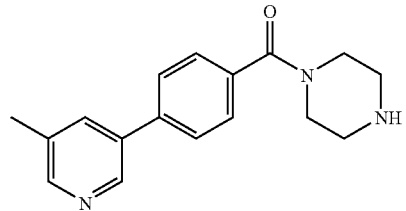 | H | N | 476 | 0.003 | C |
| 41 | 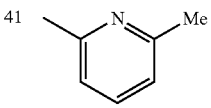 | 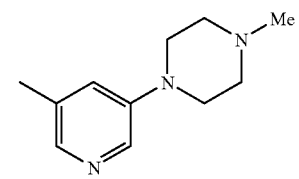 | H | N | 386 | 0.130 | F |
| 42 | 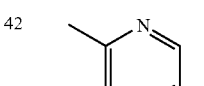 | 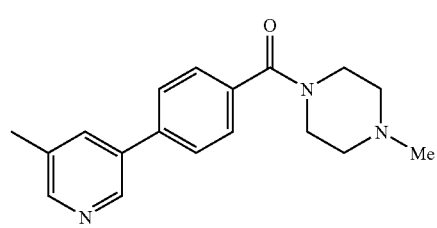 | H | N | 476 | 0.017 | C |
| 43 | 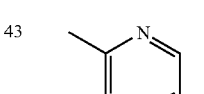 | 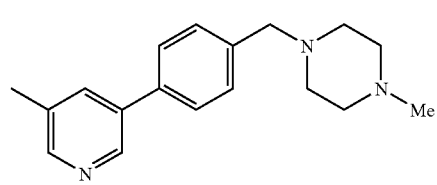 | H | N | 462 | 0.006 | C |
| 44 | 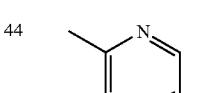 | 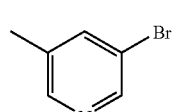 | H | N | 352/354 | 0.424 | B |
| 45 | 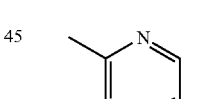 | 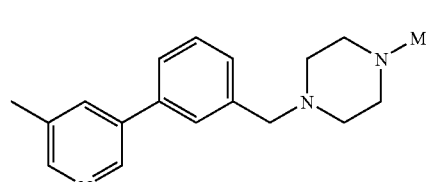 | H | N | 462 | 0.019 | C |
| 46 | 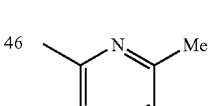 | 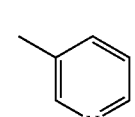 | H | CH | 287 | 0.264 | A |
| 47 | 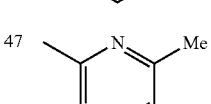 | 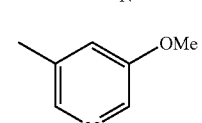 | H | CH | 317 | 0.028 | A |
| 48 | 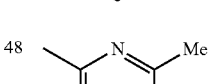 | 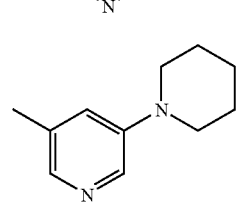 | H | N | 371 | 1.34 | F |

TABLE 1-continued

| Ex. | T1 | T2 | T3 | X | MH+ | IC$_{50}$ (μM) | Route |
|---|---|---|---|---|---|---|---|
| 49 | 2,6-Me-pyridine | 1-(5-methylpyridin-3-yl)piperidin-4-ol | H | N | 387 | 1.08 | F |
| 50 | 2,6-Me-pyridine | 3-amino-N-(5-methylpyridin-3-yl)propanamide | H | N | 374 | 0.149 | G |
| 51 | 2,6-Me-pyridine | 4-(5-methylpyridin-3-yl)morpholine | H | N | 373 | 0.660 | F |
| 52 | 2,6-Me-pyridine | 4-acetamido-N-(5-methylpyridin-3-yl)butanamide | H | N | 430 | 0.435 | A |
| 53 | 2,6-Me-pyridine | 3-acetamido-N-(5-methylpyridin-3-yl)propanamide | H | N | 416 | 0.570 | A |
| 54 | 2,6-Me-pyridine | 3-hydroxy-N-(5-methylpyridin-3-yl)propanamide | H | N | 375 | 0.119 | A |
| 55 | 2,6-Me-pyridine | 3,4-dimethylpyridine | H | N | 302 | 0.813 | A |
| 56 | 2,6-Me-pyridine | 4-methylisoquinoline | H | CH | 337 | <0.07 | A |
| 57 | 2,6-Me-pyridine | 1-methyl-4-(5-methylpyridin-3-yl)piperazine | H | CH | 385 | 0.271 | A |

TABLE 1-continued

| Ex. | T1 | T2 | T3 | X | MH+ | IC$_{50}$ (μM) | Route |
|---|---|---|---|---|---|---|---|
| 58 | 2,6-dimethylpyridin-3-yl | 5-methyl-3-(ethoxy)pyridin-3-yl | H | CH | 331 | 0.056 | A |
| 59 | 2,6-dimethylpyridin-3-yl | 5-methyl-3-[3-(aminomethyl)phenyl]pyridin-3-yl | H | N | 393 | 0.030 | C |
| 60 | 2,6-dimethylpyridin-3-yl | 5-methyl-3-(3-methoxyphenyl)pyridin-3-yl | H | CH | 393 | 0.096 | A |
| 61 | 2,6-dimethylpyridin-3-yl | 5-methyl-3-[4-(aminomethyl)phenyl]pyridin-3-yl | H | N | 393 | 0.029 | C |
| 62 | 2,6-dimethylpyridin-3-yl | 5-methyl-3-[N-(3-dimethylaminopropanoyl)amino]pyridin-3-yl | H | CH | 401 | 0.040 | A |
| 63 | 2,6-dimethylpyridin-3-yl | 5-methyl-3-[3-((4-methylpiperazin-1-yl)methyl)phenyl]pyridin-3-yl | H | CH | 475 | 0.012 | A |
| 64 | 2,6-dimethylpyridin-3-yl | 5-methyl-3-(isopropoxy)pyridin-3-yl | H | CH | 345 | 0.250 | A |
| 65 | 2,6-dimethylpyridin-3-yl | 5-methyl-3-[4-((dimethylamino)methyl)phenyl]pyridin-3-yl | H | CH | 420 | 0.005 | A |

TABLE 1-continued

| Ex. | T1 | T2 | T3 | X | MH+ | IC$_{50}$ (μM) | Route |
|---|---|---|---|---|---|---|---|
| 66 | 2,6-dimethylpyridin-3-yl | 5-methyl-3-(3-(dimethylaminomethyl)phenyl)pyridin-3-yl | H | CH | 420 | <0.069 | A |
| 67 | 2,6-dimethylpyridin-3-yl | 5-methyl-3-(3-(morpholinomethyl)phenyl)pyridin-3-yl | H | N | 463 | 0.024 | C |
| 68 | 2,6-dimethylpyridin-3-yl | 5-methyl-3-(3-(methylaminomethyl)phenyl)pyridin-3-yl | H | CH | 406 | <0.032 | E |
| 69 | 2,6-dimethylpyridin-3-yl | 5-methyl-3-(4-(morpholinomethyl)phenyl)pyridin-3-yl | H | N | 463 | <0.064 | C |
| 70 | 2,6-dimethylpyridin-3-yl | 5-methyl-3-(4-(hydroxymethyl)phenyl)pyridin-3-yl | H | N | 394 | 0.013 | C |
| 71 | 2,6-dimethylpyridin-3-yl | 5-methyl-3-(3-(hydroxymethyl)phenyl)pyridin-3-yl | H | N | 394 |  | C |
| 72 | 2,6-dimethylpyridin-3-yl | 5-methyl-3-(cyclohex-1-en-1-yl)pyridin-3-yl | H | N | 368 | 0.198 | C |
| 73 | 2,6-dimethylpyridin-3-yl | 5-methyl-3-(4-(methylaminomethyl)phenyl)pyridin-3-yl | H | CH | 406 | 0.017 | A |

TABLE 1-continued

| Ex. | T1 | T2 | T3 | X | MH+ | IC$_{50}$ (μM) | Route |
|---|---|---|---|---|---|---|---|
| 74 | 2,6-dimethylpyridinyl | 5-(cyclopent-1-enyl)pyridin-3-yl | H | N | 354 | 0.163 | C |
| 75 | 2,6-dimethylpyridinyl | 5-((dimethylamino)methyl)-[3,3'-bipyridin]-5'-yl | H | N | 422 | 0.31 | C |
| 76 | 2,6-dimethylpyridinyl | 5-((methylamino)methyl)-[3,3'-bipyridin]-5'-yl | H | N | 408 | 0.117 | C |
| 77 | 2,6-dimethylpyridinyl | 5-(4-(2-aminopropan-2-yl)phenyl)pyridin-3-yl | H | N | 421 | 0.009 | G |
| 78 | 2,6-dimethylpyridinyl | 5-(hydroxymethyl)-[3,3'-bipyridin]-5'-yl | H | N | 395 | 0.049 | C |
| 79 | 2,6-dimethylpyridinyl | (5-methylpyridin-3-yl)methanol | H | N | 318 | 1.225 | A |
| 80 | 2,6-dimethylpyridinyl | 5-methylpyridin-3-ol | H | N | 304 | 0.239 | A |
| 81 | 2,6-dimethylpyridinyl | 5-(4-(1-aminoethyl)phenyl)pyridin-3-yl | H | N | 407 | 0.017 | G |

TABLE 1-continued

| Ex. | T1 | T2 | T3 | X | MH+ | IC$_{50}$ (μM) | Route |
|---|---|---|---|---|---|---|---|
| 82 | 6-Me, 2-Me pyridine | 5-methylpyridin-3-yl-phenyl-CH2OH | H | CH | 393 | 0.012 | A |
| 83 | 6-Me, 2-Me pyridine | 5-methylpyridin-3-yl-1,3,4-oxadiazole | H | N | 356 | 0.557 | A |
| 84 | 6-Me, 2-Me pyridine | 5-methylpyridin-3-yl-phenyl-CH2NH2 (para) | H | CH | 392 | 0.036 | G |
| 85 | 6-Me, 2-Me pyridine | 5-methylpyridin-3-yl-phenyl-C(Me)2NH2 | H | N | 421 | 0.099 | G |
| 86 | 6-Me, 2-Me pyridine | 5-methylpyridin-3-yl-phenyl-CH2NH2 (meta) | H | CH | 392 | 0.008 | G |
| 87 | 6-Me, 2-Me pyridine | 5-methylpyridin-3-yl-phenyl-piperazinyl | H | N | 448 | 0.01 | C |
| 88 | 6-Me, 2-Me pyridine | 5-methylpyridin-3-yl-phenyl-CH2-morpholine | H | CH | 462 | 0.02 | A |
| 89 | 6-Me, 2-Me pyridine | 5-methylpyridin-3-yl-cyclopentenyl | H | CH | 353 | 0.079 | A |

TABLE 1-continued

| Ex. | T1 | T2 | T3 | X | MH+ | IC$_{50}$ (μM) | Route |
|---|---|---|---|---|---|---|---|
| 90 | 2,6-dimethylpyridine | 5-(3-(morpholinomethyl)phenyl)pyridine | H | CH | 462 | 0.066 | A |
| 91 | 2,6-dimethylpyridine | 5-(5-((dimethylamino)methyl)pyridin-3-yl)pyridine | H | CH | 421 | 0.109 | A |
| 92 | 2,6-dimethylpyridine | 5-(5-((methylamino)methyl)pyridin-3-yl)pyridine | H | CH | 407 | 0.103 | A |
| 93 | 2,6-dimethylpyridine | 5-(3-(hydroxymethyl)phenyl)pyridine | H | CH | 393 | 0.024 | A |
| 94 | 2,6-dimethylpyridine | 5-(methylthio)pyridine | H | N | 334 | 0.191 | A |
| 95 | 2,6-dimethylpyridine | 5-aminopyridine | H | N | 303 | 0.259 | G |
| 96 | 2,6-dimethylpyridine | 3,5-dimethylpyridine | H | N | 302 | 0.751 | A |
| 97 | 2,6-dimethylpyridine | (R)-5-(4-((3-(dimethylamino)pyrrolidin-1-yl)methyl)phenyl)pyridine | Me | N | 490 | 0.008 | C |
| 98 | 2,6-dimethylpyridine | 5-cyanopyridine | H | N | 313 | 0.799 | A |

TABLE 1-continued

| Ex. | T1 | T2 | T3 | X | MH+ | IC$_{50}$ (μM) | Route |
|---|---|---|---|---|---|---|---|
| 99 | 6-Me, 2-Me pyridine | 5-methyl-3-(pyridin-3-yl)phenyl-piperazine | H | N | 448 | 0.014 | C |
| 100 | 6-Me, 2-Me pyridine | 4-[(3-dimethylamino-pyrrolidin-1-yl)methyl]phenyl-(5-methylpyridin-3-yl) | H | N | 490 | 0.008 | C |
| 101 | 6-Me, 2-Me pyridine | 5-methyl-3-(1,2,3,6-tetrahydropyridin-4-yl)pyridine | H | N | 369 | 0.437 | C |
| 102 | 6-Me, 2-Me pyridine | 5-methyl-3-[3-(pyrrolidin-2-yl)phenyl]pyridine | H | N | 433 | 0.031 | C |
| 103 | 6-Me, 2-Me pyridine | 1-acetyl-4-(5-methylpyridin-3-yl)-1,2,3,6-tetrahydropyridine | H | N | 411 | 0.133 | A |
| 104 | 6-Me, 2-Me pyridine | 5-methyl-3-(1H-tetrazol-5-yl)pyridine | H | N | 356 | 1.026 | H |
| 105 | 6-Me, 2-Me pyridine | 3-methyl-5-(methylthio)pyridine | H | CH | 333 | 0.115 | A |
| 106 | 6-Me, 2-Me pyridine | 5-methylpyridin-3-amine | H | CH | 302 | 0.066 | G |
| 107 | 6-Me, 2-Me pyridine | 5-methylpyridin-3-ol | H | CH | 303 | 0.043 | A |

TABLE 1-continued
| Ex. | T1 | T2 | T3 | X | MH+ | IC$_{50}$ (μM) | Route |
|---|---|---|---|---|---|---|---|
| 108 | 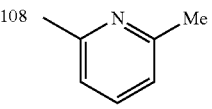 | 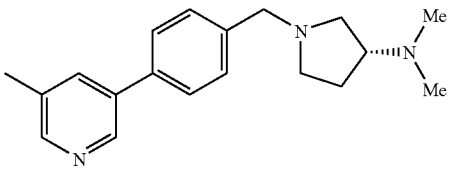 | H | CH | 489 | 0.0046 | A |
| 109 | 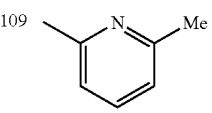 | 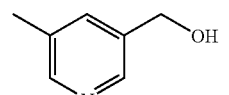 | H | CH | 317 | 0.812 | A |
| 110 | 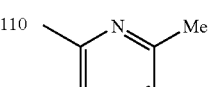 | 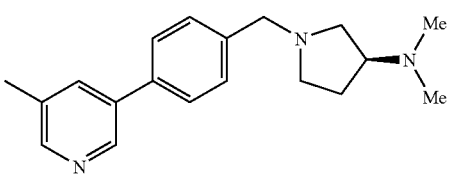 | H | CH | 489 | 0.02 | A |
| 111 | 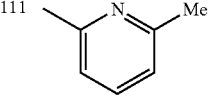 | 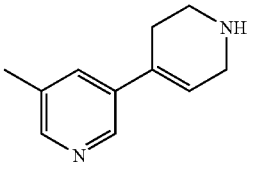 | H | CH | 368 | 0.042 | G |
| 112 | 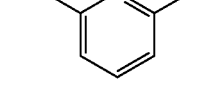 | 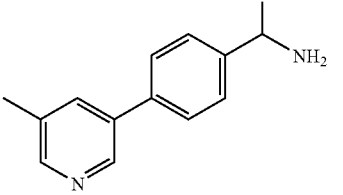 | H | CH | 406 | 0.007 | G |
| 113 | 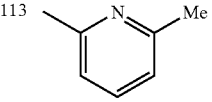 | 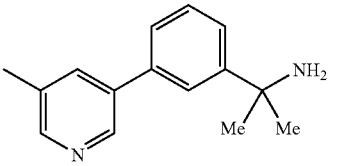 | H | CH | 420 | 0.027 | G |
| 114 | 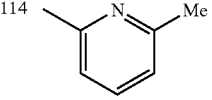 | 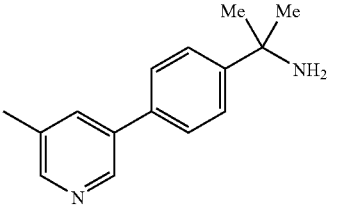 | H | CH | 420 | 0.0046 | G |
| 115 | 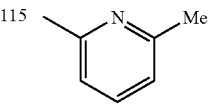 | 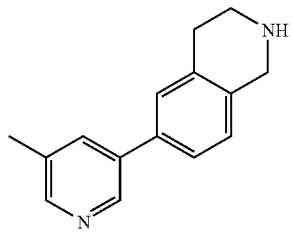 | H | N | 419 | 1.146 | G |

TABLE 1-continued

| Ex. | T1 | T2 | T3 | X | MH+ | IC$_{50}$ (μM) | Route |
|---|---|---|---|---|---|---|---|
| 116 | 2,6-dimethylpyridine | 1-methyl-4-(5-methylpyridin-3-yl)-1,2,3,6-tetrahydropyridine | H | N | 383 | 0.532 | A |
| 117 | 2,6-dimethylpyridine | 1-methyl-4-(5-methylpyridin-3-yl)-1H-pyrazole | H | N | 368 | 0.015 | C |
| 118 | 2,6-dimethylpyridine | 7-(5-methylpyridin-3-yl)-1,2,3,4-tetrahydroisoquinoline | H | N | 419 | 0.0039 | G |
| 119 | 2,6-dimethylpyridine | 3-ethynyl-5-methylpyridine | H | N | 312 | 0.292 | I |
| 120 | 2,6-dimethylpyridine | 2-(3-(5-methylpyridin-3-yl)phenyl)pyrrolidine | H | CH | 432 | 0.0036 | G |
| 121 | 2,6-dimethylpyridine | 1-(4-(5-methylpyridin-3-yl)-3,6-dihydropyridin-1(2H)-yl)ethanone | H | CH | 410 | 0.065 | A |
| 122 | 2,6-dimethylpyridine | 1-methyl-4-(3-(5-methylpyridin-3-yl)prop-2-yn-1-yl)piperazine | H | N | 424 | 0.045 | J |

TABLE 1-continued

| Ex. | T1 | T2 | T3 | X | MH+ | IC$_{50}$ (μM) | Route |
|---|---|---|---|---|---|---|---|
| 123 | 2,6-dimethylpyridin-3-yl | 5-(1-methyl-1H-pyrazol-4-yl)pyridin-3-yl | H | CH | 367 | 0.0044 | A |
| 124 | 2,6-dimethylpyridin-3-yl | 5'-methyl-N,N-dimethyl-[2,3'-bipyridin]-5-ylmethanamine | H | N | 422 | 0.011 | A |
| 125 | 2,6-dimethylpyridin-3-yl | 5'-methyl-N,N-dimethyl-[2,3'-bipyridin]-5-ylmethanamine | H | CH | 421 | 0.008 | A |
| 126 | 2,6-dimethylpyridin-3-yl | 5-methyl-3,4-dihydro-2H-pyrano[3,2-c]pyridine | H | N | 344 | 0.229 | A |
| 127 | 2,6-dimethylpyridin-3-yl | (R)-1-(4-(5-methylpyridin-3-yl)phenyl)ethanamine | H | CH | 406 | 0.017 | G |
| 128 | 2,6-dimethylpyridin-3-yl | (S)-1-(4-(5-methylpyridin-3-yl)phenyl)ethanamine | H | CH | 406 | 0.013 | G |
| 129 | 2,6-dimethylpyridin-3-yl | 3-(3-(4-methylpiperazin-1-yl)prop-1-yn-1-yl)-5-methylpyridine | H | CH | 423 | 0.016 | A |
| 130 | 2,6-dimethylpyridin-3-yl | 2-((3-(5-methylpyridin-3-yl)benzyl)amino)acetic acid | H | CH | 450 | 0.011 | G |

TABLE 1-continued

| Ex. | T1 | T2 | T3 | X | MH+ | IC$_{50}$ (µM) | Route |
|---|---|---|---|---|---|---|---|
| 131 | 6-Me, 2-Me pyridine | 5-pyridyl-phenyl-CH$_2$-NH-CH$_2$-C(O)OMe | H | CH | 464 | 0.01 | G |
| 132 | 6-Me, 2-Me pyridine | 5-pyridyl-phenyl-CH$_2$-NH-CH$_2$CH$_2$OH | H | CH | 436 | 0.0053 | K |
| 133 | 6-Me, 2-Me pyridine | 5-pyridyl-phenyl-CH$_2$-NH-CH$_2$-C(O)OMe | H | CH | 464 | 0.007 | E |
| 134 | 6-Me, 2-Me pyridine | 5-pyridyl-phenyl-CH$_2$-N(3,3-difluoropyrrolidine) | H | CH | 482 | 0.039 | E |
| 135 | 6-Me, 2-Me pyridine | 5-pyridyl-phenyl-CH$_2$-NH-CH$_2$CH$_2$OH | H | CH | 436 | 0.0033 | K |
| 136 | 6-Me, 2-Me pyridine | 5-pyridyl-phenyl-CH$_2$-NH-CH$_2$-C(O)OH | H | CH | 450 | 0.01 | L |
| 137 | 6-Me, 2-Me pyridine | 5-pyridyl-phenyl-CH$_2$-N(4-isopropylpiperazine) | H | CH | 503 | 0.009 | A |
| 138 | 6-Me, 2-Me pyridine | 5-pyridyl-phenyl-CH$_2$-N(3-hydroxyazetidine) | H | CH | 448 | 0.011 | E |

TABLE 1-continued

| Ex. | T1 | T2 | T3 | X | MH+ | IC$_{50}$ (μM) | Route |
|---|---|---|---|---|---|---|---|
| 139 | 2,6-dimethylpyridine | 5-(4-((3-hydroxypropylamino)methyl)phenyl)pyridine | H | CH | 450 | 0.009 | K |
| 140 | 2,6-dimethylpyridine | 3-((4-(5-pyridyl)benzyl)amino)propanoic acid | H | CH | 464 | 0.0062 | L |
| 141 | 2,6-dimethylpyridine | methyl N-methyl-N-(3-(5-pyridyl)benzyl)glycinate | H | CH | 478 | 0.017 | A |
| 142 | 2,6-dimethylpyridine | 2-(N-methyl-N-(3-(5-pyridyl)benzyl)amino)ethanol | H | CH | 450 | 0.01 | K |
| 143 | 2,6-dimethylpyridine | N-methyl-N-(3-(5-pyridyl)benzyl)glycine | H | CH | 464 | 0.03 | L |
| 144 | 2,6-dimethylpyridine | 2-(N-methyl-N-(3-(5-pyridyl)benzyl)amino)ethanol | H | N | 451 | 0.019 | K |
| 145 | 2,6-dimethylpyridine | N-methyl-N-(3-(5-pyridyl)benzyl)glycine | H | N | 465 | 0.026 | L |
| 146 | 2,6-dimethylpyridine | methyl N-(3-(5-pyridyl)benzyl)glycinate | H | N | 465 | 0.027 | G |

TABLE 1-continued

| Ex. | T1 | T2 | T3 | X | MH+ | IC$_{50}$ (μM) | Route |
|---|---|---|---|---|---|---|---|
| 147 | 6-Me, 2-Me pyridinyl | 5-methylpyridin-3-yl-phenyl-CH$_2$-NH-CH$_2$CH$_2$-OH | H | N | 437 | 0.01 | K |
| 148 | 6-Me, 2-Me pyridinyl | 5-methylpyridin-3-yl-phenyl-CH$_2$-NH-CH$_2$-COOH | H | N | 451 | 0.017 | G |
| 149 | 6-Me, 2-Me pyridinyl | 5-methylpyridin-3-yl-phenyl-CH$_2$-NH-CH$_2$-C(O)OMe | H | N | 465 | 0.008 | G |
| 150 | 6-Me, 2-Me pyridinyl | 5-methylpyridin-3-yl-phenyl-CH$_2$-NH-CH$_2$-COOH | H | N | 451 | 0.017 | G |
| 151 | 6-Me, 2-Me pyridinyl | 5-methylpyridin-3-yl-phenyl-CH$_2$-NH-CH$_2$CH$_2$-OH | H | N | 437 | 0.0058 | K |
| 152 | 6-Me, 2-Me pyridinyl | 5-methylpyridin-3-yl-phenyl-CH$_2$-N(Me)-CH$_2$-C(O)OMe | H | CH | 478 | 0.01 | A |
| 153 | 6-Me, 2-Me pyridinyl | 5-methylpyridin-3-yl-phenyl-CH$_2$-N(Me)-CH$_2$CH$_2$-OH | H | CH | 450 | 0.011 | K |
| 154 | 6-Me, 2-Me pyridinyl | 5-methylpyridin-3-yl-phenyl-CH$_2$-N(Me)-CH$_2$-COOH | H | CH | 464 | 0.0064 | L |

TABLE 1-continued
| Ex. | T1 | T2 | T3 | X | MH+ | IC$_{50}$ (μM) | Route |
|---|---|---|---|---|---|---|---|
| 155 | 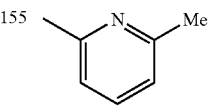 | 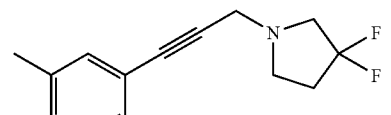 | H | CH | 430 | 0.048 | A |
| 156 | 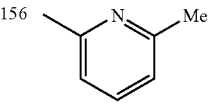 | 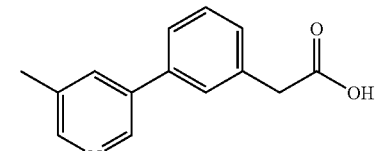 | H | CH | 421 | 0.011 | L |
| 157 | 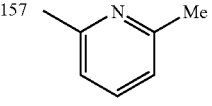 | 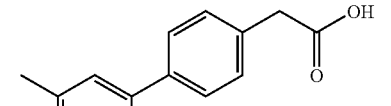 | H | CH | 421 | 0.008 | L |
| 158 | 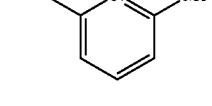 |  | H | CH | 410 | 0.027 | A |
| 159 | 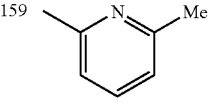 | 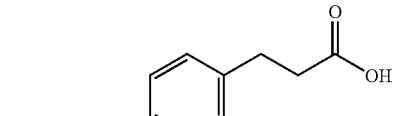 | H | CH | 435 | 0.0065 | L |
| 160 | 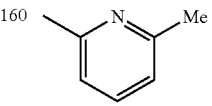 | 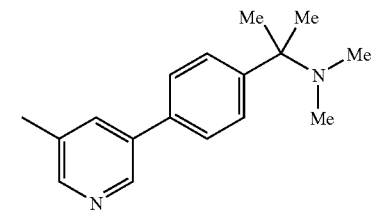 | H | CH | 448 | 0.0059 | A |
| 161 | 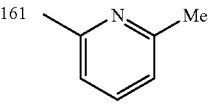 | 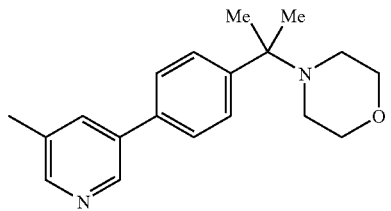 | H | CH | 490 | 0.019 | A |
| 162 | 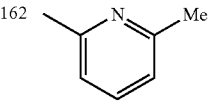 | 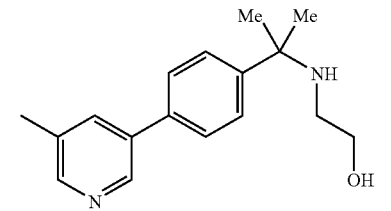 | H | CH | 464 | 0.007 | A |

TABLE 1-continued

| Ex. | T1 | T2 | T3 | X | MH+ | IC$_{50}$ (µM) | Route |
|---|---|---|---|---|---|---|---|
| 163 | 6-methyl-pyridin-2-yl (attached via methyl) | 4-[C(Me)$_2$N(Me)CH$_2$CH$_2$OH]phenyl-(5-methylpyridin-3-yl) | | H | CH | 478 | 0.0066 | A |
| 164 | 6-methyl-pyridin-2-yl | 4-[C(Me)$_2$NH$_2$]-2-methyl-phenyl-(5-methylpyridin-3-yl) | | H | CH | 434 | 0.0063 | G |
| 165 | 6-methyl-pyridin-2-yl | 4-[C(Me)$_2$NH$_2$]-3-methyl-phenyl-(5-methylpyridin-3-yl) | | H | CH | 434 | | G |
| 166 | 6-methyl-pyridin-2-yl | 5-(3-dimethylaminoprop-1-ynyl)pyridin-3-yl | | H | CH | 368 | | A |

General Conditions:

Mass spectra are run on an open access Agilent 1100 HPLC/Mass Spectrometer system using atmospheric pressure chemical ionisation. [M+H]$^+$ refers to mono-isotopic molecular weights.

Proton nuclear magnetic resonance ($^1$H-NMR) spectra are obtained on a Varian AS400 at 400 MHz. Chemical shifts are reported in delta (δ) units, parts per million (ppm) downfield from trimethylsilane.

Unless otherwise stated, all starting materials are obtained from commercial suppliers and used without further purification.

ABBREVIATIONS

AcOH is acetic acid, Boc$_2$O is di-tert-butyldicarbonate, CHCl$_3$ is chloroform, DCM is dichloromethane, DME is dimethoxyethane, DMF is dimethylformamide, EDC is 1-ethyl-3-(3-dimethyl aminopropyl)carbodiimide, EtOAc is ethyl acetate, ETOH is ethanol, h is hour(s), HCl is hydrogen chloride, HMDS is hexamethyldisilazane, HOBt is hydroxybenzotriazole, HPLC is high performance liquid chromatography, K$_2$CO$_3$ is potassium carbonate, KOAc is potassium acetate, LAH is lithium aluminum hydride, LHMDS is lithium hexamethyidisilazide, mCPBA is meta-chloroperbenzoic acid, MeCN is acetonitrile, MeOH is methanol, MgSO$_4$ is magnesium sulfate, min is minute(s), NaBH$_4$ sodium borohydride, NaBH(OAc)$_3$ is sodium (triacetoxy)cyanoborohydride, NaCl is sodium chloride, Na$_2$CO$_3$ is sodium carbonate, NaHCO$_3$ is sodium bicarbonate, NaHSO$_3$ is sodium hydrogen sulfite, NaOH is sodium hydroxide, NaOtBu is sodium tert-butoxide, NaOMe is sodium methoxide, NH$_4$Cl is ammonium chloride, NMP is N-methyl-2-pyrrolidone, PdCl$_2$(PPh$_3$)$_2$ is bis(triphenylphosphine)palladium (II) chloride, Pd(dppf)Cl$_2$ is [1,1'-bis(diphenylphosphino)ferrocene]dichloropalladium(II), Pd(PPh$_3$)$_4$ is tetrakis (triphenylphosphine)palladium(0), Pd$_2$(dba)$_3$ is tris (dibenzylideneace-tone)-dipalladium(0), POCl$_3$ is phosphoryl chloride, r.t. is room temperature, TBAF is tetrabutylammonium fluoride TEA is triethylamine, TFA is trifluoroacetic acid, THF is tetrahydrofuran, Xantphos is 9,9-dimethyl-4,5-bis(diphenylphosphanyl)xanthene.

Route A

Example 1

4-Pyridin-3-yl-2-pyridin-2-yl-7H-pyrrolo[2,3-d]pyrimidine

4-Chloro-2-pyridin-2-yl-7H-pyrrolo[2,3-d]pyrimidine (Intermediate 1) (1 eq, 1.17 mmol, 285 mg) and pyridine-3-boronic acid (ABCR GmbH & Co. KG, Karlsruhe, Germany) (2 eq, 2.35 mmol, 294 mg) are dissolved in MeCN (8 ml).

Then an aqueous Na$_2$CO$_3$ solution (2 M, 4 eq, 4.7 mmol, 2.3 ml) and PdCl$_2$(PPh$_3$)$_2$ (0.1 eq, 0.117 mmol, 84 mg) are added and the resulting mixture is heated using microwave radiation at 150° C. for 20 min. Alternatively Pd(PPh$_3$)$_4$ and DME/EtOH (1:1) can be used instead of PdCl$_2$(PPh$_3$)$_2$ and MeCN. The solvents are removed in vacuo, then aqueous NaOH solution (1 M) is added, and the solution is extracted with DCM. The organic layer is dried with MgSO$_4$, filtered, and concentrated. The crude product is recrystallized from EtOAc affording the title compound; [M+H]$^+$=274; $^1$H-NMR (400 MHz, DMSO): δ 12.52 (s, 1H), 9.46 (dd, 1H), 8.76 (m, 2H), 8.66 (td, 1H), 8.57 (td, 1H), 7.97 (dt, 1H), 7.80 (d, 1H), 7.65 (ddd, 1H), 7.48 (ddd, 1H), 7.01 (d, 1H).

Example 2

2-(6-Methyl-pyridin-2-yl)-4-pyridin-3-yl-7H-pyrrolo[2,3-d]pyrimidine is prepared by an analogous method to 4-pyridin-3-yl-2-pyridin-2-yl-7H-pyrrolo[2,3-d]pyrimidine (Example 1) by replacing 4-chloro-2-pyridin-2-yl-7H-pyrrolo[2,3-d]pyrimidine (Intermediate 1) with 4-chloro-2-(6-methyl-pyridin-2-yl)-7H-pyrrolo[2,3-d]pyrimidine (Intermediate 2).

These examples namely, 4-(5-Methoxy-pyridin-3-yl)-2-(6-methyl-pyridin-2-yl)-7H-pyrrolo[2,3-d]pyrimidine (Example 3), 2-(6-Methyl-pyridin-2-yl)-4-(5-phenyl-pyridin-3-yl)-7H-pyrrolo[2,3-d]pyrimidine (Example 4), 4-[5-(4-Methoxy-phenyl)-pyridin-3-yl]-2-(6-methyl-pyridin-2-yl)-7H-pyrrolo[2,3-d]pyrimidine (Example 5), 4-[5-(3-Methoxy-phenyl)-pyridin-3-yl]-2-(6-methyl-pyridin-2-yl)-7H-pyrrolo[2,3-d]pyrimidine (Example 6), 4-[5-(4-Fluoro-phenyl)-pyridin-3-yl]-2-(6-methyl-pyridin-2-yl)-7H-pyrrolo[2,3-d]pyrimidine (Example 7), 4-[5-(2-Methoxy-phenyl)-pyridin-3-yl]-2-(6-methyl-pyridin-2-yl)-7H-pyrrolo[2,3-d]pyrimidine (Example 8), 4-{5-[3-(4-Methyl-piperazin-1-ylmethyl)-phenyl]-pyridin-3-yl}-2-(6-methyl-pyridin-2-yl)-7H-pyrrolo[2,3-d]pyrimidine (Example 10), N-{5-[2-(6-Methyl-pyridin-2-yl)-7H-pyrrolo[2,3-d]pyrimidin-4-yl]-pyridin-3-yl}-propionamide (Example 27), 3-[2-(6-Methyl-pyridin-2-yl)-7H-pyrrolo[2,3-d]pyrimidin-4-yl]-quinoline (Example 28), 4-[2-(6-Methyl-pyridin-2-yl)-7H-pyrrolo[2,3-d]pyrimidin-4-yl]-isoquinoline (Example 29), 4-Dimethylamino-N-{5-[2-(6-methyl-pyridin-2-yl)-7H-pyrrolo[2,3-d]pyrimidin-4-yl]-pyridin-3-yl}-butyramide (Example 30), 3-Dimethylamino-N-{5-[2-(6-methyl-pyridin-2-yl)-7H-pyrrolo[2,3-d]pyrimidin-4-yl]-pyridin-3-yl}-propionamide (Example 31), 4-Acetylamino-N-{5-[2-(6-methyl-pyridin-2-yl)-7H-pyrrolo[2,3-d]pyrimidin-4-yl]-pyridin-3-yl}-butyramide (Example 52), 3-Acetylamino-N-{5-[2-(6-methyl-pyridin-2-yl)-7H-pyrrolo[2,3-d]pyrimidin-4-yl]-pyridin-3-yl}-propionamide (Example 53), 3-Hydroxy-N-{5-[2-(6-methyl-pyridin-2-yl)-7H-pyrrolo[2,3-d]pyrimidin-4-yl]-pyridin-3-yl}-propionamide (Example 54), 4-(4-Methyl-pyridin-3-yl)-2-(6-methyl-pyridin-2-yl)-7H-pyrrolo[2,3-d]pyrimidine (Example 55), {5-[2-(6-Methyl-pyridin-2-yl)-7H-pyrrolo[2,3-d]pyrimidin-4-yl]-pyridin-3-yl}-methanol (Example 79), 5-[2-(6-Methyl-pyridin-2-yl)-7H-pyrrolo[2,3-d]pyrimidin-4-yl]-pyridin-3-ol (Example 80), 2-(6-Methyl-pyridin-2-yl)-4-(5-[1,3,4]oxadiazol-2-yl-pyridin-3-yl)-7H-pyrrolo[2,3-d]pyrimidine (Example 83), 2-(6-Methyl-pyridin-2-yl)-4-(5-methylsulfanyl-pyridin-3-yl)-7H-pyrrolo[2,3-d]pyrimidine (Example 94), 4-(5-Methyl-pyridin-3-yl)-2-(6-methyl-pyridin-2-yl)-7H-pyrrolo[2,3-d]pyrimidine (Example 96), 5-[2-(6-Methyl-pyridin-2-yl)-7H-pyrrolo[2,3-d]pyrimidin-4-yl]-nicotinonitrile (Example 98), 1-{5-[2-(6-Methyl-pyridin-2-yl)-7H-pyrrolo[2,3-d]pyrimidin-4-yl]-3',6'-dihydro-2'H-[3,4']bipyridinyl-1'-yl}-ethanone (Example 103) 1'-Methyl-5-[2-(6-Methyl-pyridin-2-yl)-7H-pyrrolo[2,3-d]pyrimidin-4-yl]-1',2',3',6'-tetrahydro-[3,4']bipyridinyl (Example 116), Dimethyl-{5'-[2-(6-methyl-pyridin-2-yl)-7H-pyrrolo[2,3-d]pyrimidin-4-yl]-[2,3']bipyridinyl-5-ylmethyl}-amine (Example 124), 5-[2-(6-Methyl-pyridin-2-yl)-7H-pyrrolo[2,3-d]pyrimidin-4-yl]-3,4-dihydro-2H-pyrano[2,3-c]pyridine (Example 126), are prepared by an analogous method to that for 2-(6-methyl-pyridin-2-yl)-4-pyridin-3-yl-7H-pyrrolo[2,3-d]pyrimidine (Example 2) by replacing pyridine-3-boronic acid with the corresponding boronic acid or boronic ester, namely, 3-methoxy-5-pyridineboronic acid (Frontier Scientific Inc., Logan, USA), 3-phenyl-5-(4,4,5,5-tetramethyl-[1,3,2]dioxaborolan-2-yl)-pyridine (Intermediate 38), 3-(4-methoxy-phenyl)-5-(4,4,5,5-tetramethyl-[1,3,2]dioxaborolan-2-yl)-pyridine (Intermediate 37), 3-(3-methoxy-phenyl)-5-(4,4,5,5-tetramethyl-[1,3,2]dioxaborolan-2-yl)-pyridine (Intermediate 39), 3-(4-fluoro-phenyl)-5-(4,4,5,5-tetramethyl-[1,3,2]dioxaborolan-2-yl)-pyridine (Intermediate 40), 3-(2-methoxy-phenyl)-5-(4,4,5,5-tetramethyl-[1,3,2]dioxaborolan-2-yl)-pyridine (Intermediate 41), 1-methyl-4-{3-[5-(4,4,5,5-tetramethyl-[1,3,2]dioxaborolan-2-yl)-pyridin-3-yl]-benzyl}-piperazine (Intermediate 42), N-[5-(4,4,5,5-tetramethyl-[1,3,2]dioxaborolan-2-yl)-pyridin-3-yl]-propionamide (Intermediate 43), quinoline-3-boronic acid (Intermediate 35), isoquinoline-4-boronic acid (Intermediate 36), 4-dimethylamino-N-[5-(4,4,5,5-tetramethyl-[1,3,2]dioxaborolan-2-yl)-pyridin-3-yl]-butyramide (Intermediate 44), 3-dimethylamino-N-[5-(4,4,5,5-tetramethyl-[1,3,2]dioxaborolan-2-yl)-pyridin-3-yl]-propionamide (Intermediate 45), 4-acetylamino-N-[5-(4,4,5,5-tetramethyl-[1,3,2]dioxaborolan-2-yl)-pyridin-3-yl]-butyramide (Intermediate 47), 3-acetylamino-N-[5-(4,4,5,5-tetramethyl-[1,3,2]dioxaborolan-2-yl)-pyridin-3-yl]-propionamide (Intermediate 48), 3-hydroxy-N-[5-(4,4,5,5-tetramethyl-[1,3,2]dioxaborolan-2-yl)-pyridin-3-yl]-propionamide (Intermediate 49), 4-methyl-3-(4,4,5,5-tetramethyl-[1,3,2]dioxaborolan-2-yl)-pyridine (Intermediate 50), [5-(4,4,5,5-tetramethyl-[1,3,2]dioxaborolan-2-yl)-pyridin-3-yl]-methanol (Intermediate 105), 5-(4,4,5,5-tetramethyl-[1,3,2]dioxaborolan-2-yl)-pyridin-3-ol (Intermediate 106), 3-[1,3,4]oxadiazol-2-yl-5-(4,4,5,5-tetramethyl-[1,3,2]dioxaborolan-2-yl)-pyridine (Intermediate 109), 3-methylsulfanyl-5-(4,4,5,5-tetramethyl-[1,3,2]dioxaborolan-2-yl)-pyridine (Intermediate 120), 3-methyl-5-(4,4,5,5-tetramethyl-[1,3,2]dioxaborolan-2-yl)-pyridine (Intermediate 122), 5-(4,4,5,5-tetramethyl-[1,3,2]dioxaborolan-2-yl)-nicotinonitrile (Intermediate 123), 1-[5-(4,4,5,5-tetramethyl-[1,3,2]dioxaborolan-2-yl)-3',6'-dihydro-2'H-[3,4']bipyridinyl-1'-yl]-ethanone (Intermediate 127), 1'-methyl-5-(4,4,5,5-tetramethyl-[1,3,2]dioxaborolan-2-yl)-1',2',3',6'-tetrahydro-[3,4']bipyridinyl (Intermediate 134), dimethyl-[5'-(4,4,5,5-tetramethyl-[1,3,2]dioxaborolan-2-yl)-[2,3']bipyridinyl-5-ylmethyl]-amine (Intermediate 138), or 5-(4,4,5,5-tetramethyl-[1,3,2]dioxaborolan-2-yl)-3,4-dihydro-2H-pyrano[2,3-c]pyridine (Intermediate 139), respectively.

Example 46

6-(6-Methyl-pyridin-2-yl)-4-pyridin-3-yl-1H-pyrrolo[2,3-b]pyridine is prepared by an analogous method to that for 2-(6-methyl-pyridin-2-yl)-4-pyridin-3-yl-7H-pyrrolo[2,3-d]pyrimidine (Example 2) by replacing 4-chloro-2-pyridin-2-yl-7H-pyrrolo[2,3-d]pyrimidine (Intermediate 1) with 4-chloro-6-(6-methyl-pyridin-2-yl)-1H-pyrrolo[2,3-b]pyridine (Intermediate 6).

The following examples, namely, 4-(5-Methoxy-pyridin-3-yl)-6-(6-methyl-pyridin-2-yl)-1H-pyrrolo[2,3-b]pyridine (Example 47), 4-[6-(6-Methyl-pyridin-2-yl)-1H-pyrrolo[2,3-b]pyridin-4-yl]-isoquinoline (Example 56), 4-[5-(4-Methyl-piperazin-1-yl)-pyridin-3-yl]-6-(6-methyl-pyridin-2-yl)-1H-pyrrolo[2,3-b]pyridine (Example 57), 4-(5-Ethoxy-pyridin-3-yl)-6-(6-methyl-pyridin-2-yl)-1H-pyrrolo[2,3-b]pyridine (Example 58), 4-[5-(3-Methoxy-phenyl)-pyridin-3-yl]-6-(6-methyl-pyridin-2-yl)-1H-pyrrolo[2,3-b]pyridine (Example 60), 3-Dimethylamino-N-{5-[6-(6-methyl-pyridin-2-yl)-1H-pyrrolo[2,3-b]pyridin-4-yl]-pyridin-3-yl}-propionamide (Example 62), 4-{5-[3-(4-Methyl-piperazin-1-ylmethyl)-phenyl]-pyridin-3-yl}-6-(6-methyl-pyridin-2-yl)-1H-pyrrolo[2,3-b]pyridine (Example 63), 4-(5-Isopropoxy-pyridin-3-yl)-6-(6-methyl-pyridin-2-yl)-1H-pyrrolo[2,3-b]pyridine (Example 64), Dimethyl-(4-{5-[6-(6-methyl-pyridin-2-yl)-1H-pyrrolo[2,3-b]pyridin-4-yl]-pyridin-3-yl}-benzyl)-amine (Example 65), Dimethyl-(3-{5-[6-(6-methyl-pyridin-2-yl)-1H-pyrrolo[2,3-b]pyridin-4-yl]-pyridin-3-yl}-benzyl)-amine (Example 66), Methyl-(4-{5-[6-(6-methyl-pyridin-2-yl)-1H-pyrrolo[2,3-b]pyridin-4-yl]-pyridin-3-yl}-benzyl)-amine (Example 73), (4-{5-[6-(6-Methyl-pyridin-2-yl)-1H-pyrrolo[2,3-b]pyridin-4-yl]-pyridin-3-yl}-phenyl)-methanol (Example 82), 6-(6-Methyl-pyridin-2-yl)-4-[5-(4-morpholin-4-ylmethyl-phenyl)-pyridin-3-yl]-1H-pyrrolo[2,3-b]pyridine (Example 88), 4-(5-Cyclopent-1-enyl-pyridin-3-yl)-6-(6-methyl-pyridin-2-yl)-1H-pyrrolo[2,3-b]pyridine (Example 89), 6-(6-Methyl-pyridin-2-yl)-4-[5-(3-morpholin-4-ylmethyl-phenyl)-pyridin-3-yl]-1H-pyrrolo[2,3-b]pyridine (Example 90), Dimethyl-{5'-[6-(6-methyl-pyridin-2-yl)-1H-pyrrolo[2,3-b]pyridin-4-yl]-[3,3']bipyridinyl-5-ylmethyl}-amine (Example 91), Methyl-{5'-[6-(6-methyl-pyridin-2-yl)-1H-pyrrolo[2,3-b]pyridin-4-yl]-[3,3']bipyridinyl-5-ylmethyl}-amine (Example 92), (3-{5-[6-(6-Methyl-pyridin-2-yl)-1H-pyrrolo[2,3-b]pyridin-4-yl]-pyridin-3-yl}-phenyl)-methanol (Example 93) 6-(6-Methyl-pyridin-2-yl)-4-(5-methylsulfanyl-pyridin-3-yl)-1H-pyrrolo[2,3-b]pyridine (Example 105), 5-[6-(6-Methyl-pyridin-2-yl)-1H-pyrrolo[2,3-b]pyridin-4-yl]-pyridin-3-ol (Example 107), Dimethyl-[(R)-1-(4-{5-[6-(6-methyl-pyridin-2-yl)-1H-pyrrolo[2,3-b]pyridin-4-yl]-pyridin-3-yl}-benzyl)-pyrrolidin-3-yl]-amine (Example 108), {5-[6-(6-Methyl-pyridin-2-yl)-1H-pyrrolo[2,3-b]pyridin-4-yl]-pyridin-3-yl}-methanol (Example 109), Dimethyl-[(S)-1-(4-{5-[6-(6-methyl-pyridin-2-yl)-1H-pyrrolo[2,3-b]pyridin-4-yl]-pyridin-3-yl}-benzyl)-pyrrolidin-3-yl]-amine (Example 110), 1-{5-[6-(6-Methyl-pyridin-2-yl)-1H-pyrrolo[2,3-b]pyridin-4-yl]-3',6'-dihydro-2'H-[3,4']bipyridinyl-1'-yl}-ethanone (Example 121), 4-[5-(1-Methyl-1H-pyrazol-4-yl)-pyridin-3-yl]-6-(6-methyl-pyridin-2-yl)-1H-pyrrolo[2,3-b]pyridine (Example 123), Dimethyl-{5'-[6-(6-methyl-pyridin-2-yl)-1H-pyrrolo[2,3-b]pyridin-4-yl]-[2,3']-5-ylmethyl}-amine (Example 125), 4-{5-[3-(4-Methyl-piperazin-1-yl)-prop-1-ynyl]-pyridin-3-yl}-6-(6-methyl-pyridin-2-yl)-1H-pyrrolo[2,3-b]pyridine (Example 129), 4-{5-[4-(4-Isopropyl-piperazin-1-ylmethyl)-phenyl]-pyridin-3-yl}-6-(6-methyl-pyridin-2-yl)-1H-pyrrolo[2,3-b]pyridine (Example 137), [Methyl-(3-{5-[6-(6-methyl-pyridin-2-yl)-1H-pyrrolo[2,3-b]pyridin-4-yl]-pyridin-3-yl}-benzyl)-amino]-acetic acid methyl ester (Example 141), [Methyl-(4-{5-[6-(6-methyl-pyridin-2-yl)-1H-pyrrolo[2,3-b]pyridin-4-yl]-pyridin-3-yl}-benzyl)-amino]-acetic acid methyl ester (Example 152), 4-{5-[3-(3,3-Difluoro-pyrrolidin-1-yl)-prop-1-ynyl]-pyridin-3-yl}-6-(6-methyl-pyridin-2-yl)-1H-pyrrolo[2,3-b]pyridine (Example 155), 6-(6-Methyl-pyridin-2-yl)-4-[5-(3-morpholin-4-yl-prop-1-ynyl)-pyridin-3-yl]-1H-pyrrolo[2,3-b]pyridine (Example 158), Dimethyl-[1-methyl-1-(4-{5-[6-(6-methyl-pyridin-2-yl)-1H-pyrrolo[2,3-b]pyridin-4-yl]-pyridin-3-yl}-phenyl)-ethyl]-amine (Example 160), 4-{5-[4-(1-Methyl-1-morpholin-4-yl-ethyl)-phenyl]-pyridin-3-yl}-6-(6-methyl-pyridin-2-yl)-1H-pyrrolo[2,3-b]pyridine (Example 161), 2-[1-Methyl-1-(4-{5-[6-(6-methyl-pyridin-2-yl)-1H-pyrrolo[2,3-b]pyridin-4-yl]-pyridin-3-yl}-phenyl)-ethylamino]-ethanol (Example 162), 2-{Methyl-[1-methyl-1-(4-{5-[6-(6-methyl-pyridin-2-yl)-1H-pyrrolo[2,3-b]pyridin-4-yl]-pyridin-3-yl}-phenyl)-ethyl]-amino}-ethanol (Example 163), Dimethyl-(3-{5-[6-(6-methyl-pyridin-2-yl)-1H-pyrrolo[2,3-b]pyridin-4-yl]-pyridin-3-yl}-prop-2-ynyl)-amine (Example 166), are prepared by an analogous method to that for 6-(6-methyl-pyridin-2-yl)-4-pyridin-3-yl-1H-pyrrolo[2,3-b]pyridine (Example 46) by replacing pyridine-3-boronic acid with the corresponding boronic acid or boronic ester, namely, 3-methoxy-5-pyridineboronic acid (Frontier Scientific Inc., Logan, USA), isoquinoline-4-boronic acid (Intermediate 36), 1-methyl-4-[5-(4,4,5,5-tetramethyl-[1,3,2]dioxaborolan-2-yl)-pyridin-3-yl]-piperazine (Intermediate 51), 3-ethoxy-5-(4,4,5,5-tetramethyl-[1,3,2]dioxaborolan-2-yl)-pyridine (Intermediate 52), 3-(3-methoxy-phenyl)-5-(4,4,5,5-tetramethyl-[1,3,2]dioxaborolan-2-yl)-pyridine (Intermediate 39), 3-dimethylamino-N-[5-(4,4,5,5-tetramethyl-[1,3,2]dioxaborolan-2-yl)-pyridin-3-yl]-propionamide (Intermediate 45), 1-methyl-4-{3-[5-(4,4,5,5-tetramethyl-[1,3,2]dioxaborolan-2-yl)-pyridin-3-yl]-benzyl}-piperazine (Intermediate 42), 3-isopropoxy-5-(4,4,5,5-tetramethyl-[1,3,2]dioxaborolan-2-yl)-pyridine (Intermediate 53), dimethyl-{4-[5-(4,4,5,5-tetramethyl-[1,3,2]dioxaborolan-2-yl)-pyridin-3-yl]-benzyl}-amine (Intermediate 54), dimethyl-{3-[5-(4,4,5,5-tetramethyl-[1,3,2]dioxaborolan-2-yl)-pyridin-3-yl]-benzyl}-amine (Intermediate 55), methyl-{4-[5-(4,4,5,5-tetramethyl-[1,3,2]dioxaborolan-2-yl)-pyridin-3-yl]-benzyl}-amine (Intermediate 101), {4-[5-(4,4,5,5-tetramethyl-[1,3,2]dioxaborolan-2-yl)-pyridin-3-yl]-phenyl}-methanol (Intermediate 108), 4-{4-[5-(4,4,5,5-tetramethyl-[1,3,2]dioxaborolan-2-yl)-pyridin-3-yl]-benzyl}-morpholine (Intermediate 114), 3-cyclopent-1-enyl-5-(4,4,5,5-tetramethyl-[1,3,2]dioxaborolan-2-yl)-pyridine (Intermediate 115), 4-{3-[5-(4,4,5,5-tetramethyl-[1,3,2]dioxaborolan-2-yl)-pyridin-3-yl]-benzyl}-morpholine (Intermediate 116), dimethyl-[5'-(4,4,5,5-tetramethyl-[1,3,2]dioxaborolan-2-yl)-[3,3']bipyridinyl-5-ylmethyl]-amine (Intermediate 117), methyl-[5'-(4,4,5,5-tetramethyl-[1,3,2]dioxaborolan-2-yl)-[3,3']bipyridinyl-5-ylmethyl]-amine (Intermediate 118), {3-[5-(4,4,5,5-tetramethyl-[1,3,2]dioxaborolan-2-yl)-pyridin-3-yl]-phenyl}-methanol (Intermediate 119), 3-methylsulfanyl-5-(4,4,5,5-tetramethyl-[1,3,2]dioxaborolan-2-yl)-pyridine (Intermediate 120), 5-(4,4,5,5-tetramethyl-[1,3,2]dioxaborolan-2-yl)-pyridin-3-ol (Intermediate 106), dimethyl-((R)-1-{4-[5-(4,4,5,5-tetramethyl-[1,3,2]dioxaborolan-2-yl)-pyridin-3-yl]-benzyl}-pyrrolidin-3-yl)-amine (Intermediate 128), [5-(4,4,5,5-tetramethyl-[1,3,2]dioxaborolan-2-yl)-pyridin-3-yl]-methanol (Intermediate 105), dimethyl-((S)-1-{4-[5-(4,4,5,5-tetramethyl-[1,3,2]dioxaborolan-2-yl)-pyridin-3-yl]-benzyl}-pyrrolidin-3-yl)-amine (Intermediate 129), 1-[5-(4,4,5,5-tetramethyl-[1,3,2]dioxaborolan-2-yl)-3',6'-dihydro-2'H-[3,4']bipyridinyl-1'-yl]-ethanone (Intermediate 127), 3-(1-methyl-1H-pyrazol-4-yl)-5-(4,4,5,5-tetramethyl-[1,3,2]dioxaborolan-2-yl)-pyridine (Intermediate 137), dimethyl-[5'-(4,4,5,5-tetramethyl-[1,3,2]dioxaborolan-2-yl)-[2,3']bipyridinyl-5-ylmethyl]-amine (Intermediate 138), 1-methyl-4-{3-[5-(4,4,5,5-tetramethyl-[1,3,2]dioxaborolan-2-yl)-pyridin-3-yl]-prop-2-ynyl}-piperazine (Intermediate 144), 1-isopropyl-4-{4-[5-(4,4,5,5-tetramethyl-[1,3,2]dioxaborolan-2-yl)-pyridin-3-yl]-benzyl}-piperazine (Intermediate 147), (methyl-{3-[5-(4,4,5,5-tetramethyl-[1,3,2]dioxaborolan-2-yl)-pyridin-3-yl]-benzyl}-amino)-acetic acid methyl ester (Intermediate 148), (methyl-{4-[5-(4,4,5,5-tetramethyl-[1,3,2]dioxaborolan-2-yl)-pyridin-3-yl]-benzyl}-amino)-acetic acid methyl ester (Intermediate 150), 3-[3-(3,3-difluoro-pyrrolidin-1-yl)-prop-1-ynyl]-5-(4,4,5,5-tetramethyl-[1,3,2]dioxaborolan-2-yl)-pyridine (Intermediate 151), 4-{3-[5-(4,4,5,5-tetramethyl-[1,3,2]dioxaborolan-2-yl)-pyridin-3-yl]-prop-2-ynyl}-morpholine (Intermediate 154), dimethyl-(1-methyl-1-{4-[5-(4,4,5,5-tetramethyl-[1,3,2]dioxaborolan-2-yl)-pyridin-3-yl]-phenyl}-ethyl)-amine (Intermediate 156), 4-(1-methyl-1-{4-[5-(4,4,5,5-tetramethyl-[1,3,2]dioxaborolan-2-yl)-pyridin-3-yl]-phenyl}-ethyl)-morpholine (Intermediate 158), 2-(1-methyl-1-{4-[5-(4,4,5,5-tetramethyl-[1,3,2]dioxaborolan-2-yl)-pyridin-3-yl]-phenyl}-ethylamino)-ethanol (Intermediate 159), 2-[methyl-(1-methyl-1-{4-[5-(4,4,5,5-tetramethyl-[1,3,2]dioxaborolan-2-yl)-pyridin-3-yl]-phenyl}-ethyl)-amino]-ethanol (Intermediate 160), or dimethyl-{3-[5-(4,4,5,5-tetramethyl-[1,3,2]dioxaborolan-2-yl)-pyridin-3-yl]-prop-2-ynyl}-amine (Intermediate 165), respectively.

Route B

Example 16

4-(5-Bromo-pyridin-3-yl)-2-(6-methyl-pyridin-2-yl)-7H-pyrrolo[2,3-d]pyrimidine

To a solution of 4-iodo-2-(6-methyl-pyridin-2-yl)-7H-pyrrolo[2,3-d]pyrimidine (Intermediate 3) (1 eq, 1.50 mmol, 530 mg) and 3-bromopyridine-5-boronic acid (ABCR GmbH & Co. KG, Karlsruhe, Germany) (1.1. eq, 1.65 mmol, 339 mg) in DME/EtOH (1:1, 6 ml) are added aqueous $Na_2CO_3$ solution (2 M, 3 eq, 4.50 mmol, 2.2 ml) and $Pd(PPh_3)_4$ (0.05 eq, 0.075 mmol, 89 mg). The resulting mixture is heated using microwave radiation at 120° C. for 20 min. After cooling down to r.t., the mixture is filtered and the resulting precipitate is washed with EtOH. The residue is suspended in DCM, filtered, and dried to give the title compound; $[M+H]^+=366/368$; $^1$H-NMR (400 MHz, DMSO): δ 12.58 (s, 1H), 9.40 (m, 1H), 8.89 (m, 1H), H), 8.79 (m, 1H), 8.37 (t, 1H), 7.87-7.77 (m, 2H), 7.33 (t, 1H), 7.00 (m, 1H), 2.56 (m, 3H).

Example 44

4-(5-Bromo-pyridin-3-yl)-2-pyridin-2-yl-7H-pyrrolo[2,3-d]pyrimidine is prepared by an analogous method to that for 4-(5-bromo-pyridin-3-yl)-2-(6-methyl-pyridin-2-yl)-7H-pyrrolo[2,3-d]pyrimidine (Example 16) by replacing 4-iodo-2-(6-methyl-pyridin-2-yl)-7H-pyrrolo[2,3-d]pyrimidine (Intermediate 3) with 4-iodo-2-pyridin-2-yl-7H-pyrrolo[2,3-d]pyrimidine (Intermediate 4).

Route C

Example 9

(4-Methyl-piperazin-1-yl)-(4-{5-[2-(6-methyl-pyridin-2-yl)-7H-pyrrolo[2,3-d]pyrimidin-4-yl]-pyridin-3-yl}-phenyl)-methanone To a solution of 4-(5-bromo-pyridin-3-yl)-2-(6-methyl-pyridin-2-yl)-7H-pyrrolo[2,3-d]pyrimidine (Example 16) (1 eq, 0.273 mmol, 100 mg) and 4-(4-methylpiperazine-1-carbonyl)phenyl-boronic acid pinacol ester (ABCR GmbH & Co. KG, Karlsruhe, Germany) (1.1 eq, 0.300 mmol, 101 mg) in DME/EtOH (1:1, 2 ml), aqueous $Na_2CO_3$ solution (2 M, 3 eq, 0.82 mmol, 0.41 ml) and $Pd(PPh_3)_4$ (0.05 eq, 0.014 mmol, 16 mg) are added. The resulting mixture is heated using microwave radiation at 140° C. for 20 min. The mixture is diluted with water, basified with aqueous NaOH (1 M), extracted with DCM, and the organic layer is dried with $MgSO_4$ and filtered. After evaporation of the solvent the crude product is purified by reversed phase HPLC giving the title compound; $[M+H]^+=490$; $^1$H-NMR (400 MHz, $CDCl_3$): δ 13.09 (s, 1H), 9.50 (d, 1H), 8.98 (d, 1H), 8.78 (d, 1H), 8.66 (d, 1H), 7.84 (t, 1H), 7.76 (d, 2H), 7.58 (d, 2H), 7.45 (m, 1H), 7.33 (d, 1H), 6.87 (d, 1H), 3.84 (m, 2H), 3.53 (m, 2H), 2.74 (s, 3H), 2.55-2.35 (m, 4H), 2.34 (s, 3H).

The following examples, namely, 4-{5-[4-(4-Methyl-piperazin-1-yl)-phenyl]-pyridin-3-yl}-2-(6-methyl-pyridin-2-yl)-7H-pyrrolo[2,3-d]pyrimidine (Example 14), 4-{5-[4-(4-Isopropyl-piperazin-1-yl)-phenyl]-pyridin-3-yl}-2-(6-methyl-pyridin-2-yl)-7H-pyrrolo[2,3-d]pyrimidine (Example 15), 2-(6-Methyl-pyridin-2-yl)-4-[5-(4-piperidin-1-yl-phenyl)-pyridin-3-yl]-7H-pyrrolo[2,3-d]pyrimidine (Example 17), 2-(6-Methyl-pyridin-2-yl)-4-[5-(3-pyrrolidin-1-yl-phenyl)-pyridin-3-yl]-7H-pyrrolo[2,3-d]pyrimidine (Example 18), (4-Methyl-piperazin-1-yl)-(3-{5-[2-(6-methyl-pyridin-2-yl)-7H-pyrrolo[2,3-d]pyrimidin-4-yl]-pyridin-3-yl}-phenyl)-methanone (Example 19), 4-{5-[4-(4-Methyl-piperazin-1-ylmethyl)-phenyl]-pyridin-3-yl}-2-(6-methyl-pyridin-2-yl)-7H-pyrrolo[2,3-d]pyrimidine (Example 20), 5-[2-(6-Methyl-pyridin-2-yl)-7H-pyrrolo[2,3-d]pyrimidin-4-yl]-[3,4']bipyridinyl (Example 21), 5-[2-(6-Methyl-pyridin-2-yl)-7H-pyrrolo[2,3-d]pyrimidin-4-yl]-[3,3']bipyridinyl (Example 22), 3-{5-[2-(6-Methyl-pyridin-2-yl)-7H-pyrrolo[2,3-d]pyrimidin-4-yl]-pyridin-3-yl}-phenol (Example 23), 4-[5-(2-Fluoro-phenyl)-pyridin-3-yl]-2-(6-methyl-pyridin-2-yl)-7H-pyrrolo[2,3-d]pyrimidine (Example 24), 2-(6-Methyl-pyridin-2-yl)-4-(5-o-tolyl-pyridin-3-yl)-7H-pyrrolo[2,3-d]pyrimidine (Example 32), 4-[5-(2-Chloro-phenyl)-pyridin-3-yl]-2-(6-methyl-pyridin-2-yl)-7H-pyrrolo[2,3-d]pyrimidine (Example 33), 4-{5-[3-(4-Isopropyl-piperazin-1-ylmethyl)-phenyl]-pyridin-3-yl}-2-(6-methyl-pyridin-2-yl)-7H-pyrrolo[2,3-d]pyrimidine (Example 34), 4-{5-[4-(4-Isopropyl-piperazin-1-ylmethyl)-phenyl]-pyridin-3-yl}-2-(6-methyl-pyridin-2-yl)-7H-pyrrolo[2,3-d]pyrimidine (Example 35), Methyl-(3-{5-[2-(6-methyl-pyridin-2-yl)-7H-pyrrolo[2,3-d]pyrimidin-4-yl]-pyridin-3-yl}-benzyl)-amine (Example 36), Dimethyl-(3-{5-[2-(6-methyl-pyridin-2-yl)-7H-pyrrolo[2,3-d]pyrimidin-4-yl]-pyridin-3-yl}-benzyl)-amine (Example 37), Dimethyl-(4-{5-[2-(6-methyl-pyridin-2-yl)-7H-pyrrolo[2,3-d]pyrimidin-4-yl]-pyridin-3-yl}-benzyl)-amine (Example 38), (4-{5-[2-(6-Methyl-pyridin-2-yl)-7H-pyrrolo[2,3-d]pyrimidin-4-yl]-pyridin-3-yl}-phenyl)-piperazin-1-yl-methanone (Example 40), 3-{5-[2-(6-Methyl-pyridin-2-yl)-7H-pyrrolo[2,3-d]pyrimidin-4-yl]-pyridin-3-yl}-benzylamine (Example 59), 4-{5-[2-(6-Methyl-pyridin-2-yl)-7H-pyrrolo[2,3-d]pyrimidin-4-yl]-pyridin-3-yl}-benzylamine (Example 61), 2-(6-Methyl-pyridin-2-yl)-4-[5-(3-morpholin-4-ylmethyl-phenyl)-pyridin-3-yl]-7H-pyrrolo[2,3-d]pyrimidine (Example 67), 2-(6-Methyl-pyridin-2-yl)-4-[5-(4-morpholin-4-ylmethyl-phenyl)-pyridin-3-yl]-7H-pyrrolo[2,3-d]pyrimidine (Example 69), 4-{5-[2-(6-Methyl-pyridin-2-yl)-7H-pyrrolo[2,3-d]pyrimidin-4-yl]-pyridin-3-yl}phenyl)-methanol (Example 70), (3-{5-[2-(6-Methyl-pyridin-2-yl)-7H-pyrrolo[2,3-d]pyrimidin-4-yl]-pyridin-3-yl}-phenyl)-methanol (Example 71), 4-(5-Cyclohex-1-enyl-pyridin-3-yl)-2-(6-methyl-pyridin-2-yl)-7H-pyrrolo[2,3-d]pyrimidine (Example 72), 4-(5-Cyclopent-1-enyl-pyridin-3-yl)-2-(6-methyl-pyridin-2-yl)-7H-pyrrolo[2,3-d]pyrimidine (Example 74), Dimethyl-{5-[2-(6-methyl-pyridin-2-yl)-7H-pyrrolo[2,3-d]pyrimidin-4-yl]-[3,3']bipyridinyl-5-ylmethyl}-amine (Example 75), Methyl-{5-[2-(6-methyl-pyridin-2-yl)-7H-pyrrolo[2,3-d]pyrimidin-4-yl]-[3,3']bipyridinyl-5-ylmethyl}-amine (Example 76), {5'-[2-(6-Methyl-pyridin-2-yl)-7H-pyrrolo[2,3-d]pyrimidin-4-yl]-[3,3']bipyridinyl-5-yl}-methanol (Example 78), 2-(6-Methyl-pyridin-2-yl)-4-[5-(4-piperazin-2-yl-phenyl)-pyridin-3-yl]-7H-pyrrolo[2,3-d]pyrimidine (Example 87), Dimethyl-[(R)-1-(4-{5-[2-(6-methyl-pyridin-2-yl)-7H-pyrrolo[2,3-d]pyrimidin-4-yl]-pyridin-3-yl}-benzyl)-pyrrolidin-3-yl]-amine (Example 97), 2-(6-Methyl-pyridin-2-yl)-4-[5-(3-piperazin-2-yl-phenyl)-pyridin-3-yl]-7H-pyrrolo[2,3-d]pyrimidine (Example 99), Dimethyl-[(S)-1-(4-{5-[2-(6-methyl-pyridin-2-yl)-7H-pyrrolo[2,3-d]pyrimidin-4-yl]-pyridin-3-yl}-benzyl)-pyrrolidin-3-yl]-amine (Example 100), 4-[5-(1-Methyl-1H-pyrazol-4-yl)-pyridin-3-yl]-2-(6-methyl-pyridin-2-yl)-7H-pyrrolo[2,3-d]pyrimidine (Example 117), are prepared by an analogous method to that for (4-methyl-piperazin-1-yl)-(4-{5-[2-(6-methyl-pyridin-2-yl)-7H-pyrrolo[2,3-d]pyrimidin-4-yl]-pyridin-3-yl}-phenyl)-methanone (Example 9) by replacing 4-(4-methylpiperazine-1-carbonyl)phenylboronic acid pinacol ester with the corresponding boronic acid or boronic ester, namely 4-(4-methylpiperazin-1-yl)phenylboronic acid pinacol ester (ABCR GmbH & Co. KG, Karlsruhe, Germany), 1-isopropyl-4-[4-(4,4,5,5-tetramethyl-1,3,2-dioxaborolan-2-yl)phenyl]piperazine (Boron Molecular, Research Triangle Park, USA), 1-[4-(4,4,5,5-tetramethyl-1,3,2-dioxaborolan-2-yl)phenyl]piperidine (Maybridge Chemical Co. Ltd., Cornwall, UK), 1-[3-(4,4,5,5-tetramethyl-1,3,2-dioxaborolan-2-yl)phenyl]pyrrolidine (Maybridge Chemical Co. Ltd., Cornwall, UK), 3-(4-methylpiperazine-1-carbonyl)phenylboronic acid pinacol ester (Boron Molecular, Research Triangle Park, USA), (4-methyl-piperazin-1-ylmethyl)-phenyl-3-boronic acid (Intermediate 7), 4-pyridineboronic acid pinacol ester (ABCR GmbH & Co. KG, Karlsruhe, Germany), 3-pyridineboronic acid (Sigma-Aldrich, St. Louis, USA), 3-hydroxyphenylboronic acid (ABCR GmbH & Co. KG, Karlsruhe, Germany), 2-fluorophenylboronic acid (Sigma-Aldrich, St. Louis, USA), o-tolylboronic acid (Sigma-Aldrich, St. Louis, USA), 2-chlorophenylboronic acid (Sigma-Aldrich, St. Louis, USA), (4-isopropyl-piperazin-1-ylmethyl)-phenyl-3-boronic acid (Intermediate 8), 4-(4-isopropyl-piperazin-1-ylmethyl)-benzeneboronic acid (Intermediate 13), methylaminomethylphenyl-3-boronic acid (Intermediate 9), dimethylaminomethyl-phenyl-3-boronic acid (Intermediate 10), dimethylaminomethyl-phenyl-4-boronic acid (Intermediate 14), 4-(piperazine-1-carbonyl)phenylboronic acid pinacol ester (ABCR GmbH & Co. KG, Karlsruhe, Germany), (3-aminomethylphenyl)boronic acid hydrochloride (ABCR GmbH & Co. KG, Karlsruhe, Germany), (4-aminomethylphenyl)boronic acid hydrochloride (ABCR GmbH & Co. KG, Karlsruhe, Germany), morpholin-4-ylmethyl-phenyl-3-boronic acid (Intermediate 11), morpholin-4-ylmethyl-phenyl-4-boronic acid (Intermediate 15), 4-(hydroxymethyl)phenyl boronic acid (Sigma-Aldrich, St. Louis, USA), [3-(4,4,5,5-tetramethyl-[1,3,2]dioxaborolan-2-yl)-phenyl]-methanol (Intermediate 57), cyclohexen-1-yl-boronic acid (ABCR GmbH & Co. KG, Karlsruhe, Germany), cyclopenten-1-ylboronic acid (ABCR GmbH & Co. KG, Karlsruhe, Germany), dimethyl-[5-(4,4,5,5-tetramethyl-[1,3,2]dioxaborolan-2-yl)-pyridin-3-ylmethyl]-amine (Intermediate 102), methyl-[5-(4,4,5,5-tetramethyl-[1,3,2]dioxaborolan-2-yl)-pyridin-3-ylmethyl]-amine (Intermediate 103), [5-(4,4,5,5-tetramethyl-[1,3,2]dioxaborolan-2-yl)-pyridin-3-yl]-methanol (Intermediate 105), 2-[4-(4,4,5,5-tetramethyl-[1,3,2]dioxaborolan-2-yl)-phenyl]-piperazine (Intermediate 113), 4-((R)-3-dimethylamino-pyrrolidin-1-yl methyl)-benzeneboronic acid (Intermediate 62), 2-[3-(4,4,5,5-tetramethyl-[1,3,2]dioxaborolan-2-yl)-phenyl]-piperazine (Intermediate 124), or 4-((S)-3-dimethylamino-pyrrolidin-1-ylmethyl)-benzeneboronic acid (Intermediate 63), 1-methyl-4-(4,4,5,5-tetramethyl-[1,3,2]dioxaborolan-2-yl)-1H-pyrazole (Sigma-Aldrich, St. Louis, USA), respectively.

Example 42

(4-Methyl-piperazin-1-yl)-{4-[5-(2-pyridin-2-yl-7H-pyrrolo[2,3-d]pyrimidin-4-yl)-pyridin-3-yl]-phenyl}-methanone is prepared by an analogous method to that for (4-methyl-piperazin-1-yl)-(4-{5-[2-(6-methyl-pyridin-2-yl)-7H-pyrrolo[2,3-d]pyrimidin-4-yl]-pyridin-3-yl}-phenyl)-methanone (Example 9) by replacing 4-(5-bromo-pyridin-3-yl)-2-(6-methyl-pyridin-2-yl)-7H-pyrrolo[2,3-d]pyrimidine (Example 16) with 4-(5-bromo-pyridin-3-yl)-2-pyridin-2-yl-7H-pyrrolo[2,3-d]pyrimidine (Example 44).

The following examples, namely, 4-{5-[4-(4-Methyl-piperazin-1-ylmethyl)-phenyl]-pyridin-3-yl}-2-pyridin-2-yl-7H-pyrrolo[2,3-d]pyrimidine (Example 43), 4-{5-[3-(4-Methyl-piperazin-1-ylmethyl)-phenyl]-pyridin-3-yl}-2-pyridin-2-yl-7H-pyrrolo[2,3-d]pyrimidine (Example 45), are prepared by an analogous method to that for (4-methyl-piperazin-1-yl)-{4-[5-(2-pyridin-2-yl-7H-pyrrolo[2,3-d]pyrimidin-4-yl)-pyridin-3-yl]-phenyl}-methanone (Example 42) by replacing 4-(4-methylpiperazine-1-carbonyl)phenylboronic acid pinacol ester with the corresponding boronic acid or boronic ester, namely, (4-methyl-piperazin-1-ylmethyl)-phenyl-4-boronic acid (Intermediate 12), or (4-methyl-piperazin-1-ylmethyl)-phenyl-3-boronic acid (Intermediate 7), respectively.

Route D

Example 11

N-Ethyl-5-[2-(6-methyl-pyridin-2-yl)-7H-pyrrolo[2,3-d]pyrimidin-4-yl]-nicotinamide To a solution of 5-[2-(6-methyl-pyridin-2-yl)-7H-pyrrolo[2,3-d]pyrimidin-4-yl]-nicotinic acid (Intermediate 5) (1 eq, 0.143 mmol, 50 mg) in MeCN (3 ml), ethylamine (1 eq, 0.143 mmol, 6.6 mg), EDC hydrochloride (1.5 eq, 0.215 mmol, 42 mg), HOBt (1.2 eq, 0.172 mmol, 23 mg), and TEA (5 eq, 0.720 mmol, 0.1 ml) are added. The mixture is heated using microwave radiation at 140° C. for 20 min. The resulting precipitate is filtered off and washed with MeCN. Drying the solid in vacuum affords the title compound; [M+H]$^+$=359; $^1$H-NMR (400 MHz, CD$_3$OD): δ 9.55 (d, 1H), 9.15 (t, 1H), 9.12 (d, 1H), 8.47 (d, 1H), 7.86 (t, 1H), 7.67 (d, 1H), 7.36 (d, 1H), 6.99 (d, 1H), 3.50 (q, 2H), 2.68 (s, 3H), 1.29 (t, 3H).

The following examples, namely, N-(2-Dimethylamino-ethyl)-5-[2-(6-methyl-pyridin-2-yl)-7H-pyrrolo[2,3-d]pyrimidin-4-yl]-nicotinamide (Example 12), N-(3-Dimethylamino-propyl)-5-[2-(6-methyl-pyridin-2-yl)-7H-pyrrolo[2,3-d]pyrimidin-4-yl]-nicotinamide (Example 13), N-[3-(4-Methyl-piperazin-1-yl)-propyl]-5-[2-(6-methyl-pyridin-2-yl)-7H-pyrrolo[2,3-d]pyrimidin-4-yl]-nicotinamide (Example 25), N-(3-Hydroxy-propyl)-5-[2-(6-methyl-pyridin-2-yl)-7H-pyrrolo[2,3-d]pyrimidin-4-yl]-nicotinamide (Example 26), are prepared by an analogous method to that for N-Ethyl-5-[2-(6-methyl-pyridin-2-yl)-7H-pyrrolo[2,3-d]pyrimidin-4-yl]-nicotinamide (Example 11) by replacing ethylamine with the corresponding amine, namely 2-dimethylaminoethylamine (Sigma-Aldrich, St. Louis, USA), 3-dimethylamino-1-propylamine (Sigma-Aldrich, St. Louis, USA), 1-(3-aminopropyl)-4-methylpiperazine (ABCR GmbH & Co. KG, Karlsruhe, Germany), or 1-aminopropanole (Sigma-Aldrich, St. Louis, USA), respectively.

Route E

Example 39

Methyl-(4-{5-[2-(6-methyl-pyridin-2-yl)-7H-pyrrolo[2,3-d]pyrimidin-4-yl]-pyridin-3-yl}-benzyl)-amine To a suspension of 4-{5-[2-(6-methyl-pyridin-2-yl)-7H-pyrrolo[2,3-d]pyrimidin-4-yl]-pyridin-3-yl}-benzaldehyde (Intermediate 58) (1 eq, 0.243 mmol, 100 mg) and methylamine hydrochloride (Sigma-Aldrich, St. Louis, USA) (1 eq, 0.243 mmol, 16.7 mg) in DCM (1 ml) is added AcOH (1.1 eq, 0.267 mmol, 15.3 ul). The solution is stirred for 5 min, then NaBH(OAc)$_3$ (1.05 eq, 0.255 mmol, 57 mg) is added. After stirring the resulting mixture at r.t. for 1.5 h the solvents are removed in vacuo. The residue is taken up in aqueous NaHCO$_3$ solution and extracted with DCM. The organic layer is washed with brine, dried over MgSO$_4$, and filtered. The solvents are removed in vacuo and purification of the residue by reversed phase HPLC is yielding the title compound; [M+H]$^+$=407; $^1$H-NMR (400 MHz, CDCl$_3$): δ 12.52 (s, 1H), 9.43 (s, 1H), 8.95 (s, 1H), 8.73 (s, 1H), 8.66 (d, 1H), 7.83 (t, 1H), 7.64 (d, 2H), 7.49-7.46 (m, 3H), 7.32 (d, 1H), 6.88 (d, 1H), 3.86 (s, 2H), 2.75 (s, 3H), 2.56 (s, 3H).

Example 68

Methyl-(3-{5-[6-(6-methyl-pyridin-2-yl)-1H-pyrrolo[2,3-b]pyridin-4-yl]-pyridin-3-yl}-benzyl)-amine is prepared by an analogous method to that for methyl-(4-{5-[2-(6-methyl-pyridin-2-yl)-7H-pyrrolo[2,3-d]pyrimidin-4-yl]-pyridin-3-yl}-benzyl)-amine (Example 39) by replacing 4-{5-[2-(6-Methyl-pyridin-2-yl)-7H-pyrrolo[2,3-d]pyrimidin-4-yl]-pyridin-3-yl}-benzaldehyde (Intermediate 58) with 3-{5-[6-(6-methyl-pyridin-2-yl)-1H-pyrrolo[2,3-b]pyridin-4-yl]-3-yl}-benzaldehyde (Intermediate 60).

Example 133

(4-{5-[6-(6-Methyl-pyridin-2-yl)-1H-pyrrolo[2,3-b]pyridin-4-yl]-pyridin-3-yl}-benzylamino)-acetic acid methyl ester is prepared by an analogous method to that for methyl-(4-{5-[2-(6-methyl-pyridin-2-yl)-7H-pyrrolo[2,3-d]pyrimidin-4-yl]-pyridin-3-yl}-benzyl)-amine (Example 39) by replacing 4-{5-[2-(6-Methyl-pyridin-2-yl)-7H-pyrrolo[2,3-d]pyrimidin-4-yl]-pyridin-3-yl}-benzaldehyde (Intermediate 58) with 4-{5-[6-(6-methyl-pyridin-2-yl)-1H-pyrrolo[2,3-b]pyridin-4-yl]-3-yl}-benzaldehyde (Intermediate 185) and methylamine hydrochloride with amino-acetic acid methyl ester (Rare Chemicals GmbH, Kiel, Germany).

The following examples, namely, 4-{5-[4-(3,3-Difluoro-pyrrolidin-1-ylmethyl)-phenyl]-pyridin-3-yl}-6-(6-methyl-pyridin-2-yl)-1H-pyrrolo[2,3-b]pyridine (Example 134), 1-(4-{5-[6-(6-Methyl-pyridin-2-yl)-1H-pyrrolo[2,3-b]pyridin-4-yl]-pyridin-3-yl}-benzyl)-azetidin-3-ol (Example 138), are prepared by an analogous method to that for (4-{5-[6-(6-methyl-pyridin-2-yl)-1H-pyrrolo[2,3-b]pyridin-4-yl]-pyridin-3-yl}-benzylamino)-acetic acid methyl ester (Example 133) by replacing amino-acetic acid methyl ester with the corresponding amine, namely, 3,3-difluoro-pyrrolidine hydrochloride (ABCR GmbH & Co. KG, Karlsruhe, Germany), or azetidin-3-ol (Davos Chemical Corporation, Upper Saddle River, USA), respectively.

Route F

Example 41

4-[5-(4-Methyl-piperazin-1-yl)-pyridin-3-yl]-2-(6-methyl-pyridin-2-yl)-7H-pyrrolo[2,3-d]pyrimidine To a solution of 4-(5-bromo-pyridin-3-yl)-2-(6-methyl-pyridin-2-yl)-7H-pyrrolo[2,3-d]pyrimidine (Example 16) (1 eq, 0.81 mmol, 300 mg) in THF (5 ml), 1-methylpiperazine (Sigma-Aldrich, St. Louis, USA) (1.25 eq, 1.01 mmol, 0.114 ml), Pd$_2$(dba)$_3$ (0.04 eq, 0.032 mmol, 29.7 mg), and 2-(dicyclohexylphosphino)biphenyl (0.08 eq, 0.065 mmol, 25.5 mg) are added. After addition of LHMDS (1 M in THF, 2.2 eq, 1.8 mmol, 1.8 ml) the mixture is refluxed for 5 h, cooled down and quenched by addition of aqueous HCl solution (2M, 5 ml). The mixture is adjusted to pH 6 using aqueous NaOH solution and washed with ethyl acetate. The aqueous layer is adjusted to pH 12 and extracted with EtOAc. The organic layer is washed with brine, dried with MgSO$_4$, filtered, and concentrated. Purification by reversed phase HPLC is giving the title compound, [M+H]$^+$=422; $^1$H-NMR (400 MHz, CD$_3$OD): δ 9.20 (s, 1H), 9.06-9.03 (m, 2H), 8.74 (d, 1H), 8.67 (t, 1H), 8.04 (d, 1H), 7.99 (d, 1H), 7.23 (d, 1H), 4.41 (m, 2H), 3.76 (m, 2H), 3.60 (m, 2H), 3.43 (m, 2H), 3.04 (s, 3H), 3.03 (s, 3H).

The following examples, namely, 5'-[2-(6-Methyl-pyridin-2-yl)-7H-pyrrolo[2,3-d]pyrimidin-4-yl]-3,4,5,6-tetrahydro-2H-[1,3']bipyridinyl (Example 48), 5'-[2-(6-Methyl-pyridin-2-yl)-7H-pyrrolo[2,3-d]pyrimidin-4-yl]-3,4,5,6-tetrahydro-2H-[1,3']bipyridinyl-4-ol (Example 49), 2-(6-Methyl-pyridin-2-yl)-4-(5-morpholin-4-yl-pyridin-3-yl)-7H-pyrrolo[2,3-d]pyrimidine (Example 51), are prepared by an analogous method to that for 4-[5-(4-methyl-piperazin-1-yl)-pyridin-3-yl]-2-(6-methyl-pyridin-2-yl)-7H-pyrrolo[2,3-d]pyrimidine (Example 41) by replacing 1-methylpiperazine with the corresponding amine, namely, piperidine (Sigma-Aldrich, St. Louis, USA), piperidin-4-ol (Sigma-Aldrich, St. Louis, USA), or morpholine (Sigma-Aldrich, St. Louis, USA), respectively.

Route G

Example 50

3-Amino-N-{5-[2-(6-methyl-pyridin-2-yl)-7H-pyrrolo[2,3-d]pyrimidin-4-yl]-pyridin-3-yl}-propionamide A solution of (2-{5-[2-(6-methyl-pyridin-2-yl)-7H-pyrrolo[2,3-d]pyrimidin-4-yl]-pyridin-3-ylcarbamoyl}-ethyl)-carbamic acid tert-butyl ester (Intermediate 59) (1 eq, 1.54 mmol, 774 mg) in DCM (100 ml) is cooled to 5° C. using an ice bath. Then TFA (20 eq, 32.7 mmol, 2.52 ml) is added within 5 min, the cooling bath is removed, and the mixture is stirred for 1 h at r.t. After addition of saturated aqueous K$_2$CO$_3$ solution the layers are separated and the aqueous layer is concentrated. The residue is taken up in MeCN, filtered, and the filtrate is concentrated. Column chromatography (DCM/MeOH/NH$_3$) yields the title compound; [M+H]$^+$= 374;

$^1$H-NMR (400 MHz, DMSO): δ 12.59 (s, 1H), 10.76 (s, 1H), 9.17 (s, 1H), 8.96 (m, 2H), 8.38 (m, 1H), 7.88-7.76 (m, 2H), 7.38-7.11 (m, 3H), 6.97 (s, 1H), 3.14 (m, 2H), 2.82 (m, 2H), 2.59 (s, 3H).

The following examples, namely, 1-Methyl-1-(4-{5-[2-(6-methyl-pyridin-2-yl)-7H-pyrrolo[2,3-d]pyrimidin-4-yl]-pyridin-3-yl}-phenyl)-ethylamine (Example 77), 1-(4-{5-[2-(6-Methyl-pyridin-2-yl)-7H-pyrrolo[2,3-d]pyrimidin-4-yl]-pyridin-3-yl}-phenyl)-ethylamine (Example 81), 4-{5-[6-(6-Methyl-pyridin-2-yl)-1H-pyrrolo[2,3-b]pyridin-4-yl]-pyridin-3-yl}-benzylamine (Example 84), 1-Methyl-1-(3-{5-[2-(6-methyl-pyridin-2-yl)-7H-pyrrolo[2,3-d]pyrimidin-4-yl]-pyridin-3-yl}-phenyl)-ethylamine (Example 85), 3-{5-[6-(6-Methyl-pyridin-2-yl)-1H-pyrrolo[2,3-b]pyridin-4-yl]-pyridin-3-yl}-benzylamine (Example 86), 5-[2-(6-Methyl-pyridin-2-yl)-7H-pyrrolo[2,3-d]pyrimidin-4-yl]-pyridin-3-ylamine (Example 95), 5-[2-(6-Methyl-pyridin-2-yl)-7H-pyrrolo[2,3-d]pyrimidin-4-yl]-1',2',3',6'-tetrahydro-[3,4']bipyridinyl (Example 101), 2-(6-Methyl-pyridin-2-yl)-4-[5-(3-pyrrolidin-2-yl-phenyl)-pyridin-3-yl]-7H-pyrrolo[2,3-d]pyrimidine (Example 102), 5-[6-(6-Methyl-pyridin-2-yl)-1H-pyrrolo[2,3-b]pyridin-4-yl]-pyridin-3-ylamine (Example 106), 5-[6-(6-Methyl-pyridin-2-yl)-1H-pyrrolo[2,3-b]pyridin-4-yl]-1',2',3',6'-tetrahydro-[3,4']bipyridinyl (Example 111), 1-(4-{5-[6-(6-Methyl-pyridin-2-yl)-1H-pyrrolo[2,3-b]pyridin-4-yl]-pyridin-3-yl}-phenyl)-ethylamine (Example 112), 1-Methyl-1-(3-{5-[6-(6-methyl-pyridin-2-yl)-1H-pyrrolo[2,3-b]pyridin-4-yl]-pyridin-3-yl}-phenyl)-ethylamine (Example 113), 1-Methyl-1-(4-{5-[6-(6-methyl-pyridin-2-yl)-1H-pyrrolo[2,3-b]pyridin-4-yl]-pyridin-3-yl}-phenyl)-ethylamine (Example 114), 6-{5-[2-(6-Methyl-pyridin-2-yl)-7H-pyrrolo[2,3-d]pyrimidin-4-yl]-pyridin-3-yl}-1,2,3,4-tetrahydro-isoquinoline (Example 115), 7-{5-[2-(6-Methyl-pyridin-2-yl)-7H-pyrrolo[2,3-d]pyrimidin-4-yl]-pyridin-3-yl}-1,2,3,4-tetrahydro-isoquinoline (Example 118), 6-(6-Methyl-pyridin-2-yl)-4-[5-(3-pyrrolidin-2-yl-phenyl)-pyridin-3-yl]-1H-pyrrolo[2,3-b]pyridine (Example 120), (S)-1-(4-{5-[6-(6-Methyl-pyridin-2-yl)-1H-pyrrolo[2,3-b]pyridin-4-yl]-pyridin-3-yl}-phenyl)-ethylamine (Example 127), (R)-1-(4-{5-[6-(6-Methyl-pyridin-2-yl)-1H-pyrrolo[2,3-b]pyridin-4-yl]-pyridin-3-yl}-phenyl)-ethylamine (Example 128), (3-{5-[6-(6-Methyl-pyridin-2-yl)-1H-pyrrolo[2,3-b]pyridin-4-yl]-pyridin-3-yl}-benzylamino)-acetic acid (Example 130), (3-{5-[6-(6-Methyl-pyridin-2-yl)-1H-pyrrolo[2,3-b]pyridin-4-yl]-pyridin-3-yl}-benzylamino)-acetic acid methyl ester (Example 131), (3-{5-[2-(6-Methyl-pyridin-2-yl)-7H-pyrrolo[2,3-d]pyrimidin-4-yl]-pyridin-3-yl}-benzylamino)-acetic acid methyl ester (Example 146), (3-{5-[2-(6-Methyl-pyridin-2-yl)-7H-pyrrolo[2,3-d]pyrimidin-4-yl]-pyridin-3-yl}-benzylamino)-acetic acid (Example 148), (4-{5-[2-(6-Methyl-pyridin-2-yl)-7H-pyrrolo[2,3-d]pyrimidin-4-yl]-pyridin-3-yl}-benzylamino)-acetic acid methyl ester (Example 149), (4-{5-[2-(6-Methyl-pyridin-2-yl)-7H-pyrrolo[2,3-d]pyrimidin-4-yl]-pyridin-3-yl}-benzylamino)-acetic acid (Example 150), 1-Methyl-1-(3-methyl-4-{5-[6-(6-methyl-pyridin-2-yl)-1H-pyrrolo[2,3-b]pyridin-4-yl]-pyridin-3-yl}-phenyl)-ethylamine (Example 164), 1-Methyl-1-(2-methyl-4-{5-[6-(6-methyl-pyridin-2-yl)-1H-pyrrolo[2,3-b]pyridin-4-yl]-pyridin-3-yl}-phenyl)-ethylamine (Example 165), are prepared by an analogous method to that for 3-amino-N-{5-[2-(6-methyl-pyridin-2-yl)-7H-pyrrolo[2,3-d]pyrimidin-4-yl]-pyridin-3-yl}-propionamide (Example 50) by (2-{5-[2-(6-methyl-pyridin-2-yl)-7H-pyrrolo[2,3-d]pyrimidin-4-yl]-pyridin-3-ylcarbamoyl}-ethyl)-carbamic acid tert-butyl ester (Intermediate 59) with the corresponding carbamic acid tert-butyl ester, namely, [1-methyl-1-(4-{5-[2-(6-methyl-pyridin-2-yl)-7H-pyrrolo[2,3-d]pyrimidin-4-yl]-pyridin-3-yl}-henyl)-ethyl]-carbamic acid tert-butyl ester (Intermediate 166), [1-(4-{5-[2-(6-methyl-pyridin-2-yl)-7H-pyrrolo[2,3-d]pyrimidin-4-yl]-pyridin-3-yl}-phenyl)-ethyl]-carbamic acid tert-butyl ester (Intermediate 169), (4-{5-[6-(6-methyl-pyridin-2-yl)-1H-pyrrolo[2,3-b]pyridin-4-yl]-pyridin-3-yl}-benzyl)-carbamic acid tert-butyl ester (Intermediate 175), [1-methyl-1-(3-{5-[2-(6-methyl-pyridin-2-yl)-7H-pyrrolo[2,3-d]pyrimidin-4-yl]-pyridin-3-yl}-henyl)-ethyl]-carbamic acid tert-butyl ester (Intermediate 168), (3-{5-[6-(6-methyl-pyridin-2-yl)-1H-pyrrolo[2,3-b]pyridin-4-yl]-pyridin-3-yl}-benzyl)-carbamic acid tert-butyl ester (Intermediate 176), {5-[2-(6-methyl-pyridin-2-yl)-7H-pyrrolo[2,3-d]pyrimidin-4-yl]-pyridin-3-yl}-carbamic acid tert-butyl ester (Intermediate 172), 5-[2-(6-methyl-pyridin-2-yl)-7H-pyrrolo[2,3-d]pyrimidin-4-yl]-3',6'-dihydro-2'H-[3,4']bipyridinyl-1'-carboxylic acid tert-butyl ester (Intermediate 173), 2-(3-{5-[2-(6-methyl-pyridin-2-yl)-7H-pyrrolo[2,3-d]pyrimidin-4-yl]-pyridin-3-yl}-phenyl)-pyrrolidine-1-carboxylic acid tert-butyl ester (Intermediate 169), {5-[6-(6-methyl-pyridin-2-yl)-1H-pyrrolo[2,3-b]pyridin-4-yl]-pyridin-3-yl}-carbamic acid tert-butyl ester (Intermediate 177), 5-[6-(6-methyl-pyridin-2-yl)-1H-pyrrolo[2,3-b]pyridin-4-yl]-3',6'-dihydro-2'H-[3,4']bipyridinyl-1'-carboxylic acid tert-butyl ester (Intermediate 178), [1-(4-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 179), [1-methyl-1-(3-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 180), [1-methyl-1-(4-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 181), 6-{5-[2-(6-methyl-pyridin-2-yl)-7H-pyrrolo[2,3-d]pyrimidin-4-yl]-pyridin-3-yl}-3,4-dihydro-1H-isoquinoline-2-carboxylic acid tert-butyl ester (Intermediate 170), 7-{5-[2-(6-methyl-pyridin-2-yl)-7H-pyrrolo[2,3-d]pyrimidin-4-yl]-pyridin-3-yl}-3,4-dihydro-1H-isoquinoline-2-carboxylic acid tert-butyl ester (Intermediate 171), 2-(3-{5-[6-(6-methyl-pyridin-2-yl)-1H-pyrrolo[2,3-b]pyridin-4-yl]-pyridin-3-yl}-phenyl)-pyrrolidine-1-carboxylic acid tert-butyl ester (Intermediate 182), [(S)-1-(4-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 183), [(R)-1-(4-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 184), [tert-butoxycarbonyl-(3-{5-[6-(6-methyl-pyridin-2-yl)-1H-pyrrolo[2,3-b]pyridin-4-yl]-pyridin-3-yl}-benzyl)-amino]-acetic acid (Intermediate 191), [tert-butoxycarbonyl-(3-{5-[6-(6-methyl-pyridin-2-yl)-1H-pyrrolo[2,3-b]pyridin-4-yl]-pyridin-3-yl}-benzyl)-amino]-acetic acid methyl ester (Intermediate 192), [tert-butoxycarbonyl-(3-{5-[2-(6-methyl-pyridin-2-yl)-7H-pyrrolo[2,3-d]pyrimidin-4-yl]-pyridin-3-yl}-benzyl)-amino]-acetic acid methyl ester (Intermediate 193), [tert-butoxycarbonyl-(3-{5-[2-(6-methyl-pyridin-2-yl)-7H-pyrrolo[2,3-d]pyrimidin-4-yl]-pyridin-3-yl}-benzyl)-amino]-acetic acid (Intermediate 194), [tert-butoxycarbonyl-(4-{5-[2-(6-methyl-pyridin-2-yl)-7H-pyrrolo[2,3-d]pyrimidin-4-yl]-pyridin-3-yl}-benzyl)-amino]-acetic acid methyl ester (Intermediate 195), [tert-butoxycarbonyl-(4-{5-[2-(6-methyl-pyridin-2-yl)-7H-pyrrolo[2,3-d]pyrimidin-4-yl]-pyridin-3-yl}-benzyl)-amino]-acetic acid (Intermediate 196), [1-methyl-1-(3-methyl-4-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 189), or [1-methyl-1-(2-methyl-4-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 190), respectively.

Route H

Example 104

2-(6-Methyl-pyridin-2-yl)-4-[5-(1H-tetrazol-5-yl)-pyridin-3-yl]-7H-pyrrolo[2,3-d]pyrimidine A mixture of 5-[2-(6-methyl-pyridin-2-yl)-7H-pyrrolo[2,3-d]pyrimidin-4-yl]-nicotinitrile (Example 98) (1 eq, 0.8 mmol, 250 mg), sodium azide (4.5 eq, 3.6 mmol, 234 mg), ammonium chloride (4.5 eq, 3.6 mmol, 193 mg), and DMF (2.5 ml) is heated using microwave radiation for 40 min at 120° C. The solvent is removed in vacuo, and the crude mixture is purified by column chromatography (DCM/MeOH/NH$_3$) giving the title compound; [M+H]$^+$=356; $^1$H-NMR (400 MHz, CD$_3$OD): δ 9.46 (d, 1H), 9.36 (d, 1H), 9.28 (t, 1H), 8.59 (d, 1H), 7.96 (d, 1H), 7.43 (d, 1H), 7.09 (d, 1H), 2.70 (s, 3H).

Route I

Example 119

4-(5-Ethynyl-pyridin-3-yl)-2-(6-methyl-pyridin-2-yl)-7H-pyrrolo[2,3-d]pyrimidine To a solution of 2-(6-methyl-pyridin-2-yl)-4-(5-trimethylsilanylethynyl-pyridin-3-yl)-7H-pyrrolo[2,3-d]pyrimidine (Intermediate 216) (1 eq, 0.181 mmol, 70 mg) in THF (2 ml) is added TBAF (1 M in THF, 2 eq, 0.36 mmol, 0.36 ml). The resulting mixture is stirred for 10 min at r.t., then the solvent is removed in vacuo. Water is added, then the mixture is extracted with EtOAc. The organic layer is washed with sat. aqueous NaCl solution, dried with MgSO$_4$, and concentrated under reduced pressure. The crude product is recrystallized from EtOAc giving the title compound; [M+H]$^+$=312; $^1$H-NMR (400 MHz, CDCl$_3$): δ 12.90 (s, 1H), 9.47 (d, 1H), 8.86 (d, 1H), 8.70-8.64 (m, 2H), 7.84 (t, 1H), 7.45 (m, 1H), 7.33 (d, 1H), 6.84 (d, 1H), 3.22 (s, 1H), 2.74 (s, 3H).

Route J

Example 122

4-{5-[3-(4-Methyl-piperazin-1-yl)-prop-1-ynyl]-pyridin-3-yl}-2-(6-methyl-pyridin-2-yl)-7H-pyrrolo[2,3-d]pyrimidine To a suspension of of 4-(5-bromo-pyridin-3-yl)-2-(6-methyl-pyridin-2-yl)-7H-pyrrolo[2,3-d]pyrimidine (Example 16) (1 eq, 0.669 mmol, 245 mg) in DME (3.5 ml) are added TEA (2 eq, 1.34 mmol, 135 mg), copper (I) iodide (0.5 eq, 0.335 mmol, 63.7 mg), Pd(PPh$_3$)$_4$ (0.1 eq, 0.067 mmol, 77 mg), and 1-ethyl-4-prop-2-ynyl-piperazine (Tyger Scientific, Ewing, USA) (1 eq, 0.669 mmol, 92 mg). The resulting mixture is heated using microwave radiation for 20 min at 120° C. The mixture is filtered through a pad of Celite and concentrated under reduced pressure. 2M aqueous HCl is added, and the mixture is washed with DCM. The aqueous layer is adjusted to pH 10 using 2M aqueous NaOH, and extracted with DCM. The organic layer is dried over MgSO$_4$, and the solvents are removed in vacuo. The crude mixture is purified using reversed phase HPLC to give the title compound; [M+H]$^+$=424; $^1$H-NMR (400 MHz, CD$_3$OD): δ 12.23 (s, 1H), 9.40 (d, 1H), 8.79 (d, 1H), 8.66 (d, 1H), 8.61 (t, 1H), 7.85 (t, 1H), 7.45 (t, 1H), 7.32 (d, 1H), 6.85 (m, 1H), 3.60 (s, 2H), 2.74 (s, 3H), 2.70-2.50 (m, 8H), 2.33 (s, 3H).

Route K

Example 132

2-(3-{5-[6-(6-Methyl-pyridin-2-yl)-1H-pyrrolo[2,3-b]pyridin-4-yl]-pyridin-3-yl}-benzylamino)-ethanol To a solution of (3-{5-[6-(6-methyl-pyridin-2-yl)-1H-pyrrolo[2,3-b]pyridin-4-yl]-pyridin-3-yl}-benzylamino)-acetic acid methyl ester (Example 131) (1 eq, 0.216 mmol, 100 mg) in THF (2.5 ml) at 0° C. is added LAH (1M in THF, 0.8 eq, 0.173 mmol, 0.173 ml). The resulting suspension is allowed to warm to r.t. and then stirred for 1 h at this temperature. After cooling to 0° C. sat. aqueous Na$_2$SO$_4$ solution is added, and the mixture is stirred for additional 30 min. The suspension is filtered and concentrated under reduced pressure. Addition of 4 M aqueous NaOH solution is followed by extraction with EtOAc. The organic layer is dried with MgSO$_4$, filtered, and concentrated under reduced pressure. The crude product is recrystallized using EtOAc/MeCN to give the title compound; [M+H]$^+$=436; $^1$H-NMR (400 MHz, CD$_3$OD): δ 8.98 (d, 1H), 8.90 (d, 1H), 8.50 (t, 1H), 8.26 (s, 1H), 8.20 (d, 1H), 7.80-7.76 (m, 2H), 7.68 (d, 1H), 7.56 (d, 1H), 7.50 (t, 1H), 7.43 (d, 1H), 7.25 (d, 1H), 6.70 (d, 1H), 3.89 (s, 2H), 3.69 (t, 2H), 2.77 (t, 2H), 2.62 (s, 3H).

The following examples, namely, 2-(4-{5-[6-(6-Methyl-pyridin-2-yl)-1H-pyrrolo[2,3-b]pyridin-4-yl]-pyridin-3-yl}-benzylamino)-ethanol (Example 135), 3-(4-{5-[6-(6-Methyl-pyridin-2-yl)-1H-pyrrolo[2,3-b]pyridin-4-yl]-pyridin-3-yl}-benzylamino)-propan-1-ol (Example 139), 2-[Methyl-(3-{5-[6-(6-methyl-pyridin-2-yl)-1H-pyrrolo[2,3-b]pyridin-4-yl]-pyridin-3-yl}-benzyl)-amino]-ethanol (Example 142), 2-[Methyl-(3-{5-[2-(6-methyl-pyridin-2-yl)-7H-pyrrolo[2,3-d]pyrimidin-4-yl]-pyridin-3-yl}-benzyl)-amino]-ethanol (Example 144), 2-(3-{5-[2-(6-Methyl-pyridin-2-yl)-7H-pyrrolo[2,3-d]pyrimidin-4-yl]-pyridin-3-yl}-benzylamino)-ethanol (Example 147), 2-(4-{5-[2-(6-Methyl-pyridin-2-yl)-7H-pyrrolo[2,3-d]pyrimidin-4-yl]-pyridin-3-yl}-benzylamino-ethanol (Example 151), 2-[Methyl-(4-{5-[6-(6-methyl-pyridin-2-yl)-1H-pyrrolo[2,3-b]pyridin-4-yl]-pyridin-3-yl}-benzyl)-amino]-ethanol (Example 153), are prepared by an analogous method to that for 2-(3-{5-[6-(6-methyl-pyridin-2-yl)-1H-pyrrolo[2,3-b]pyridin-4-yl]-pyridin-3-yl}-benzylamino)-ethanol (Example 132) by replacing (3-{5-[6-(6-methyl-pyridin-2-yl)-1H-pyrrolo[2,3-b]pyridin-4-yl]-pyridin-3-yl}-benzylamino)-acetic acid methyl ester (Example 131) with the corresponding ester, namely, (4-{5-[6-(6-methyl-pyridin-2-yl)-1H-pyrrolo[2,3-b]pyridin-4-yl]-pyridin-3-yl}-benzylamino)-acetic acid methyl ester (Example 133), 3-(4-{5-[6-(6-methyl-pyridin-2-yl)-1H-pyrrolo[2,3-b]pyridin-4-yl]-pyridin-3-yl}-benzylamino)-propionic acid ethyl ester (Intermediate 222), [methyl-(3-{5-[6-(6-methyl-pyridin-2-yl)-1H-pyrrolo[2,3-b]pyridin-4-yl]-pyridin-3-yl}-benzyl)-amino]-acetic acid methyl ester (Example 141), [methyl-(3-{5-[2-(6-methyl-pyridin-2-yl)-7H-pyrrolo[2,3-d]pyrimidin-4-yl]-pyridin-3-yl}-benzyl)-amino]-acetic acid methyl ester (Intermediate 174), (3-{5-[2-(6-methyl-pyridin-2-yl)-7H-pyrrolo[2,3-d]pyrimidin-4-yl]-pyridin-3-yl}-benzylamino)-acetic acid methyl ester (Example 146), (4-{5-[2-(6-methyl-pyridin-2-yl)-7H-pyrrolo[2,3-d]pyrimidin-4-yl]-pyridin-3-yl}-benzylamino)-acetic acid methyl ester (Example 149), or [methyl-(4-{5-[6-(6-methyl-pyridin-2- yl)-1H-pyrrolo[2,3-b]pyridin-4-yl]-pyridin-3-yl}-benzyl)-amino]-acetic acid methyl ester (Example 152), respectively.

Route L

Example 136

(4-{5-[6-(6-Methyl-pyridin-2-yl)-1H-pyrrolo[2,3-b]pyridin-4-yl]-pyridin-3-yl}-benzylamino)-acetic acid To a solution of (4-{5-[6-(6-methyl-pyridin-2-yl)-1H-pyrrolo[2,3-b]pyridin-4-yl]-pyridin-3-yl}-benzylamino)-acetic acid methyl ester (Example 133) (1 eq, 0.216 mmol, 100 mg) in MeOH (10 ml) is added aqueous NaOH solution (1 M, 25 eq, 5.39 mmol, 5.39 ml). The resulting mixture is stirred for 1 h at r.t. Water is added, then the mixture is adjusted to pH 4 using AcOH, then washed with DCM/isopropanol (3:1). The aqueous layer is concentrated in vacuo, and the remaining residue is purified by column chromatography (DCM/MeOH/NH$_3$) and subsequent reversed phase HPLC giving the title compound; [M+H]$^+$=450; $^1$H-NMR (400 MHz, CD$_3$OD): δ 9.01 (m, 1H), 8.92 (m, 1H), 8.52 (m, 1H), 8.31 (d, 1H), 8.25 (s, 1H), 7.98-7.87 (m, 3H), 7.69-7.62 (m, 3H), 7.40 (d, 1H), 6.73 (d, 1H), 4.32 (s, 2H), 3.70 (s, 2H), 2.69 (s, 3H).

The following examples, namely, 3-(4-{5-[6-(6-Methyl-pyridin-2-yl)-1H-pyrrolo[2,3-b]pyridin-4-yl]-pyridin-3-yl}-benzylamino)-propionic acid (Example 140), [Methyl-(3-{5-[6-(6-methyl-pyridin-2-yl)-1H-pyrrolo[2,3-b]pyridin-4-yl]-pyridin-3-yl}-benzyl)-amino]-acetic acid (Example 143), Methyl-(3-{5-[2-(6-methyl-pyridin-2-yl)-7H-pyrrolo[2,3-d]pyrimidin-4-yl]-pyridin-3-yl}-benzyl)-amino]-acetic acid (Example 145), [Methyl-(4-{5-[6-(6-methyl-pyridin-2-yl)-1H-pyrrolo[2,3-b]pyridin-4-yl]-pyridin-3-yl}-benzyl)-amino]-acetic acid acid (Example 154), (3-{5-[6-(6-Methyl-pyridin-2-yl)-1H-pyrrolo[2,3-b]pyridin-4-yl]-pyridin-3-yl}-phenyl)-acetic acid (Example 156), (4-{5-[6-(6-Methyl-pyridin-2-yl)-1H-pyrrolo[2,3-b]pyridin-4-yl]-pyridin-3-yl}-phenyl)-acetic acid (Example 157), 3-(4-{5-[6-(6-Methyl-pyridin-2-yl)-1H-pyrrolo[2,3-b]pyridin-4-yl]-pyridin-3-yl}-phenyl)-propionic acid (Example 159), are prepared by an analogous method to that for (4-{5-[6-(6-Methyl-pyridin-2-yl)-1H-pyrrolo[2,3-b]pyridin-4-yl]-pyridin-3-yl}-benzylamino)-acetic acid (Example 136) by replacing (4-{5-[6-(6-methyl-pyridin-2-yl)-1H-pyrrolo[2,3-b]pyridin-4-yl]-pyridin-3-yl}-benzylamino)-acetic acid methyl ester (Example 133) with the corresponding ester, namely, 3-(4-{5-[6-(6-methyl-pyridin-2-yl)-1H-pyrrolo[2,3-b]pyridin-4-yl]-pyridin-3-yl}-benzylamino)-propionic acid ethyl ester (Intermediate 222), [methyl-(3-{5-[6-(6-methyl-pyridin-2-yl)-1H-pyrrolo[2,3-b]pyridin-4-yl]-pyridin-3-yl}-benzyl)-amino]-acetic acid methyl ester (Example 141), [methyl-(3-{5-[2-(6-methyl-pyridin-2-yl)-7H-pyrrolo[2,3-d]pyrimidin-4-yl]-pyridin-3-yl}-benzyl)-amino]-acetic acid methyl ester (Intermediate 174), [methyl-(4-{5-[6-(6-methyl-pyridin-2-yl)-1H-pyrrolo[2,3-b]pyridin-4-yl]-pyridin-3-yl}-benzyl)-amino]-acetic acid methyl ester (Example 152), (3-{5-[6-(6-methyl-pyridin-2-yl)-1H-pyrrolo[2,3-b]pyridin-4-yl]-pyridin-3-yl}-phenyl)-acetic acid methyl ester (Intermediate 186), (4-{5-[6-(6-methyl-pyridin-2-yl)-1H-pyrrolo[2,3-b]pyridin-4-yl]-pyridin-3-yl}-phenyl)-acetic acid methyl ester (Intermediate 187), or 3-(4-{5-[6-(6-methyl-pyridin-2-yl)-1H-pyrrolo[2,3-b]pyridin-4-yl]-pyridin-3-yl}-phenyl)-propionic acid methyl ester (Intermediate 188), respectively.

Preparation of Intermediate Compounds

Intermediate 1

4-Chloro-2-pyridin-2-yl-7H-pyrrolo[2,3-d]pyrimidine

Step A: Pyridine-2-carboximidic acid methyl ester

Pyridine-2-carbonitrile (Sigma-Aldrich, St. Louis, USA) (1 eq, 190 mmol, 20 g) is dissolved in MeOH (150 ml), then NaOMe (5.4 M in MeOH, 1.1 eq, 209 mmol, 38.7 ml) is added. The resulting mixture is stirred for 16 h at r.t. The solvents are removed in vacuo, then water is added, and the resulting aqueous mixture is extracted with DCM. The organic layer is dried with MgSO$_4$, filtered, and the solvent is removed in vacuo yielding the title compound; [M+H]$^+$=138.

Step B: Pyridine-2-carboxamidine

To a solution of pyridine-2-carboximidic acid methyl ester (1 eq, 176 mmol, 24 g) in EtOH (150 ml), a solution of NH$_4$Cl (1 eq, 176 mmol, 9.5 g) in water (40 ml) is added. The resulting mixture is refluxed for 5 h. The solvents are evaporated and the residue is recrystallized from EtOH yielding the title compound; [M+H]$^+$=122.

Step C: 2-Pyridin-2-yl-7H-pyrrolo[2,3-d]pyrimidin-4-ol

Pyridine-2-carboxamidine (1 eq, 24.8 mmol, 5.69 g) is dissolved in EtOH (60 ml). After addition of NaOMe (30% in MeOH, 1.5 eq, 37 mmol, 6.9 ml) the mixture is stirred for 3 h at r.t. and then filtered. The filtrate is added to 2-cyano-4,4-diethoxy-butyric acid ethyl ester (see Journal of Heterocyclic Chemistry (2006), 43 (6), 1523-1531) (1 eq, 24.8 mmol, 3.01 g) and the resulting mixture is heated at 80° C. for 18 h. The solvents are evaporated, then water (50 ml), EtOH (50 ml) and aqueous HCl solution (2M, 50 ml) are added and the mixture is stirred at 0° C. for 2 h. The mixture is adjusted to pH 8 using aqueous NaOH solution (8 M) and the resulting precipitate is filtered and washed with cold water. The crystals are dried in vacuo giving the title compound; [M+H]$^+$=213.

Step D: 4-Chloro-2-pyridin-2-yl-7H-pyrrolo[2,3-d]pyrimidine

2-Pyridin-2-yl-7H-pyrrolo[2,3-d]pyrimidin-4-ol (1 eq, 5.56 mmol, 1.18 g) is added to POCl$_3$ (10 ml), and the resulting mixture is heated at 110° C. for 18 h. The mixture is concentrated in vacuo and then water is added. The aqueous solution is heated at 40° C. for 15 min, cooled down to r.t., and adjusted to pH 9 with aqueous NaOH solution (8 M). The resulting precipitate is filtered and washed with water and MeOH to give the title compound; [M+H]$^+$=231.

Intermediate 2

4-Chloro-2-(6-methyl-pyridin-2-yl)-7H-pyrrolo[2,3-d]pyrimidine is prepared by an analogous method to 4-chloro-2-pyridin-2-yl-7H-pyrrolo[2,3-d]pyrimidine (Intermediate 1) by replacing pyridine-2-carbonitrile (Step A) with 6-methyl-pyridine-2-carbonitrile (Sigma-Aldrich, St. Louis, USA).

Intermediate 3

4-Iodo-2-(6-methyl-pyridin-2-yl)-7H-pyrrolo[2,3-d]pyrimidine

4-Chloro-2-(6-methyl-pyridin-2-yl)-7H-pyrrolo[2,3-d]pyrimidine (Intermediate 2) (1 eq, 4.09 mmol, 1.00 g) is dissolved in THF (20 ml). Then a solution of HCl in Dioxan (4 M, 5 ml) is added, and the resulting mixture is stirred for 20 min at r.t. The solvents are removed in vacuo and the remaining salt is dried overnight. It is then suspended in MeCN (12 ml), NaI is added (10 eq, 40.9 mmol, 6.13 g), and the mixture is heated using microwave radiation at 170° C. for 40 min. The mixture is diluted with aqueous $K_2CO_3$ solution (10%), extracted with DCM, and the organic layer is washed with aqueous $NaHSO_3$ solution (15%), dried with $MgSO_4$ and filtered. Evaporation of the solvent leads the title compound; $[M+H]^+=337$.

Intermediate 4

4-Iodo-2-pyridin-2-yl-7H-pyrrolo[2,3-d]pyrimidine is prepared by an analogous method to 4-iodo-2-(6-methyl-pyridin-2-yl)-7H-pyrrolo[2,3-d]pyrimidine (Intermediate 3) by replacing 4-chloro-2-(6-methyl-pyridin-2-yl)-7H-pyrrolo[2,3-d]pyrimidine (Intermediate 2) with 4-chloro-2-pyridin-2-yl-7H-pyrrolo[2,3-d]pyrimidine (Intermediate 1).

Intermediate 5

5-[2-(6-Methyl-pyridin-2-yl)-7H-pyrrolo[2,3-d]pyrimidin-4-yl]-nicotinic acid To a solution of 4-chloro-2-(6-methyl-pyridin-2-yl)-7H-pyrrolo[2,3-d]pyrimidine (Intermediate 2) (1 eq, 1.94 mmol, 500 mg) and 3-ethoxycarbonylpyridine-5-boronic acid pinacol ester (Frontier Scientific, Logan, USA) (1.5. eq, 2.91 mmol, 820 mg) in DME/EtOH (1:1, 6 ml), aqueous $Na_2CO_3$ solution (2 M, 3 eq, 5.80 mmol, 2.9 ml) and $Pd(PPh_3)_4$ (0.05 eq, 0.097 mmol, 116 mg) are added. The resulting mixture is heated using microwave radiation at 120° C. for 20 min. The solvents are evaporated and the remaining residue is suspended in MeOH (30 ml). The mixture is cooled to 0° C., then aqueous NaOH solution (1 M, 1.9 eq, 3.60 mmol, 3.6 ml) is added. After stirring for 10 min at this temperature, the mixture is allowed to warm up to r.t. and stirred for another 1 h. After cooling down to 0° C., glacial acetic acid (5 ml) and water (100 ml) are added. The resulting precipitate is filtered and washed with water giving the title compound; $[M+H]^+=332$.

Intermediate 6

4-Chloro-6-(6-methyl-pyridin-2-yl)-1H-pyrrolo[2,3-b]pyridine

Step A: 4-Chloro-1H-pyrrolo[2,3-b]pyridine 7-oxide

To a solution of 4-chloro-1H-pyrrolo[2,3-b]pyridine (see Journal of Organic Chemistry (2006), 71 (10), 4021-4023) (1 eq, 18.6 g, 122 mmol) in $CHCl_3$ at 0° C., mCPBA (1 eq, 122 mmol, 27.3 g) is added portionwise over 20 min by keeping the temperature at 0-10° C. The resulting suspension is stirred for 30 min at 0-5° C., warmed up to r.t. and stirred for another 1 h. The reaction mixture is diluted with water (300 ml), then $K_2CO_3$ (22 g) is added, and the mixture is stirred for 30 min. The layers are separated and the aqueous layer is extracted with DCM/Isopropanol (3:1). The combined organic layers are washed with aqueous $K_2CO_3$ solution, dried over $MgSO_4$, filtered, and concentrated to give the title compound; $[M+H]^+=169$.

Step B: (6-Bromo-4-chloro-pyrrolo[2,3-b]pyridin-1-yl)-phenyl-methanone

To a solution of 4-chloro-1H-pyrrolo[2,3-b]pyridine 7-oxide (1 eq, 84.5 mmol, 15 g) in THF (100 ml), a solution of HMDS (1 eq, 84.5 mmol, 18.0 ml) in THF (50 ml) and a solution of benzoyl bromide (2.5 eq, 211 mmol, 26.1 ml) in THF (50 ml) are added in parallel and dropwise over 30 min by keeping the temperature between 20-30° C. The resulting suspension is stirred at r.t. for 30 min, then diluted with aqueous $NaHCO_3$ solution, and extracted with EtOAc. The organic layer is washed with aqueous $NaHCO_3$ solution, dried over $MgSO_4$, filtered, and concentrated. Recrystallization form isopropanol/heptane yields the title compound; $[M+H]^+=336$.

Step C: 6-Bromo-4-chloro-1H-pyrrolo[2,3-b]pyridine (6-Bromo-4-chloro-pyrrolo[2,3-b]pyridin-1-yl)-phenyl-methanone (1 eq, 69.7 mmol, 23.4 g) is dissolved in MeOH (300 ml), then aqueous NaOH solution (1 M, 120 ml) is added and the resulting mixture is stirred for 18 h at r.t. The mixture is extracted with DCM and EtOAc, the extracts are combined and the solvents are removed in vacuo. Recrystallization from MeOH yields the title compound; $[M+H]^+=231$.

Step D: 4-Chloro-6-(6-methyl-pyridin-2-yl)-1H-pyrrolo[2,3-b]pyridine

To a solution of 6-bromo-4-chloro-1H-pyrrolo[2,3-b]pyridine (1 eq, 11.0 mmol, 2.76 g) in MeCN (20 ml), 2-methyl-6-tributylstannanyl-pyridine (see Chemistry, A European Journal (2005), 11 (23), 6818-6828) (1 eq, 11.0 mmol, 4.19 g) and $Pd(PPh_3)_4$ (0.01 eq, 0.110 mmol, 131 mg) are added. The resulting mixture is heated using microwave radiation for 15 min at 160° C. The mixture is diluted with diethyl ether and extracted with aqueous HCl solution (2 M). The aqueous layer is basified with aqueous NaOH solution (4 M) and extracted with DCM. The organic layer is dried with $MgSO_4$, filtered, and concentrated. The residue is taken up in hexane and stirred at r.t. for 1 h. The suspension is filtered and dried giving the title compound; $[M+H]^+=244$.

Intermediate 7

(4-Methyl-piperazin-1-ylmethyl)-phenyl-3-boronic acid

To a solution of 3-formylphenylboronic acid (ABCR GmbH & Co. KG, Karlsruhe, Germany) (1 eq, 19.4 mmol, 3.00 g) and 1-methylpiperazine (Sigma-Aldrich, St. Louis, USA) (1 eq, 19.4 mmol, 2.2 ml) in DCM (25 ml), AcOH (1.1 eq, 21.3 mmol, 1.22 ml) is added. The solution is stirred for 5 min, then $NaBH(OAc)_3$ (1.05 eq, 20.4 mmol, 4.55 g) is added. After stirring the resulting mixture at r.t. for 1.5 h the solvents are removed in vacuo. MeCN is added and the resulting precipitate is filtered and dried to give the title compound; $[M+H]^+=235$.

Intermediates 8 to 11

The following intermediates, namely, (4-isopropyl-piperazin-1-ylmethyl)-phenyl-3-boronic acid (Intermediate 8), methylaminomethyl-phenyl-3-boronic acid (Intermediate 9), dimethylaminomethyl-phenyl-3-boronic acid (Intermediate 10), morpholin-4-ylmethyl-phenyl-3-boronic acid (Intermediate 11), are prepared by an analogous method to that for (4-methyl-piperazin-1-ylmethyl)-phenyl-3-boronic acid (Intermediate 7) by replacing 1-methylpiperazine with the corresponding amine, namely, 1-isopropylpiperazine (ABCR GmbH & Co. KG, Karlsruhe, Germany), methylamine (Sigma-Aldrich, St. Louis, USA), dimethylamine (Sigma-Aldrich, St. Louis, USA), or morpholine (Sigma-Aldrich, St. Louis, USA), respectively.

Intermediate 12

(4-Methyl-piperazin-1-ylmethyl)-phenyl-4-boronic acid is prepared by an analogous method to (4-methyl-piperazin-1-ylmethyl)-phenyl-3-boronic acid (Intermediate 7) by replacing 3-formylphenylboronic acid with 4-formylphenylboronic acid (Sigma-Aldrich, St. Louis, USA).

Intermediates 13 to 15 and 61 to 63

The following intermediates, namely, 4-(4-isopropyl-piperazin-1-ylmethyl)-benzeneboronic acid (Intermediate 13), dimethylaminomethyl-phenyl-4-boronic acid (Intermediate 14), morpholin-4-ylmethyl-phenyl-4-boronic acid (Intermediate 15), methylaminomethyl-phenyl-4-boronic acid (Intermediate 61) 4-((R)-3-dimethylamino-pyrrolidin-1-yl methyl)-benzeneboronic acid (Intermediate 62), 4-((S)-3-dimethylamino-pyrrolidin-1-ylmethyl)-benzeneboronic acid (Intermediate 63), are prepared by an analogous method to that for (4-methyl-piperazin-1-ylmethyl)-phenyl-4-boronic acid (Intermediate 12) by replacing 1-methylpiperazine with the corresponding amine, namely, 1-isopropylpiperazine (ABCR GmbH & Co. KG, Karlsruhe, Germany), dimethylamine (Sigma-Aldrich, St. Louis, USA), morpholine (Sigma-Aldrich, St. Louis, USA), methylamine (Sigma-Aldrich, St. Louis, USA), (R)-3-(dimethylamino)pyrrolidine (Sigma-Aldrich, St. Louis, USA), or (S)-3-(dimethylamino) pyrrolidine (Sigma-Aldrich, St. Louis, USA), respectively.

Intermediates 64 and 65

The following intermediates, namely, (5-bromo-pyridin-3-ylmethyl)-dimethyl-amine (Intermediate 64), (6-bromo-pyridin-3-ylmethyl)-dimethyl-amine (Intermediate 65), are prepared by an analogous method to dimethylaminomethyl-phenyl-3-boronic acid (Intermediate 10) by replacing 3-formylphenylboronic acid with the corresponding aldehyde, namely, 5-bromo-pyridine-3-carbaldehyde (Sigma-Aldrich, St. Louis, USA), or 6-bromo-pyridine-3-carbaldehyde (Sigma-Aldrich, St. Louis, USA), respectively.

Intermediate 66

5-Bromo-1'-methyl-1',2',3',6'-tetrahydro-[3,4']bipyridinyl is prepared by an analogous method to (4-methyl-piperazin-1-ylmethyl)-phenyl-3-boronic acid (Intermediate 7) by replacing 3-formylphenylboronic acid with formaldehyde and 1-methyl-piperazine with 5-bromo-1',2',3',6'-tetrahydro-[3,4']bipyridinyl (Intermediate 214).

Intermediate 67

[3-(5-Bromo-pyridin-3-yl)-benzylamino]-acetic acid methyl ester is prepared by an analogous method to (4-methyl-piperazin-1-ylmethyl)-phenyl-3-boronic acid (Intermediate 7) by replacing 3-formylphenylboronic acid with 3-(5-bromo-pyridin-3-yl)-benzaldehyde (Intermediate 24) and 1-methylpiperazine with amino-acetic acid methyl ester (Rare Chemicals GmbH, Kiel, Germany).

Intermediate 68

[4-(5-Bromo-pyridin-3-yl)-benzylamino]-acetic acid methyl ester is prepared by an analogous method to [3-(5-bromo-pyridin-3-yl)-benzylamino]-acetic acid methyl ester (Intermediate 67) by replacing 3-(5-bromo-pyridin-3-yl)-benzaldehyde (Intermediate 24) with 4-(5-bromo-pyridin-3-yl)-benzaldehyde (Intermediate 92).

Intermediates 69 to 71

{[3-(5-bromo-pyridin-3-yl)-benzyl]-methyl-amino}-acetic acid methyl ester (Intermediate 69), {[4-(5-bromo-pyridin-3-yl)-benzyl]-methyl-amino}-acetic acid methyl ester (Intermediate 70), 2-({1-[4-(5-bromo-pyridin-3-yl)-phenyl]-1-methyl-ethyl}-methyl-amino)-ethanol (Intermediate 71) are prepared by an analogous method to 5-bromo-1'-methyl-1',2',3',6'-tetrahydro-[3,4']bipyridinyl (Intermediate 66) by replacing 5-bromo-1',2',3',6'-tetrahydro-[3,4']bipyridinyl (Intermediate 214) with the corresponding amine, namely, [3-(5-bromo-pyridin-3-yl)-benzylamino]-acetic acid methyl ester (Intermediate 67), [4-(5-bromo-pyridin-3-yl)-benzylamino]-acetic acid methyl ester (Intermediate 68), or 2-{1-[4-(5-Bromo-pyridin-3-yl)-phenyl]-1-methyl-ethylamino}-ethanol (Intermediate 231), respectively.

Intermediate 16

3-Bromo-5-(4-methoxy-phenyl)-pyridine

To a solution of 3,5-dibromopyridine (Sigma-Aldrich, St. Louis, USA) (1 eq, 8.4 mmol, 2 g) and 4-methoxy-phenylboronic acid (Sigma-Aldrich, St. Louis, USA) (1 eq, 8.4 mmol, 1.30 g) in MeCN (12 ml), $Na_2CO_3$ (2 eq, 16.7 mmol, 1.79 g) and $Pd(PPh_3)_4$ (0.04 eq, 0.334 mmol, 398 mg) are added. The mixture is heated using microwave radiation at 140° C. for 10 min. The solvents are evaporated, the residue is taken up in aqueous NaOH solution (1 M) and extracted with DCM. The organic layer is washed with brine, dried over $MgSO_4$, filtered, and concentrated in vacuo. Purification by column chromatography (hexane/EtOAc) yields the title compound; $[M+H]^+=264/266$.

Intermediates 17 to 24 and 72 to 99

The following intermediates, namely, 3-Bromo-5-phenyl-pyridine (Intermediate 17), 3-bromo-5-(3-methoxy-phenyl)-pyridine (Intermediate 18), 3-bromo-5-(4-fluoro-phenyl)-pyridine (Intermediate 19), 3-bromo-5-(2-methoxy-phenyl)-pyridine (Intermediate 20), 1-[3-(5-bromo-pyridin-3-yl)-benzyl]-4-methyl-piperazine (Intermediate 21), [4-(5-bromo-pyridin-3-yl)-benzyl]-dimethyl-amine (Intermediate 22), [3-(5-bromo-pyridin-3-yl)-benzyl]-dimethyl-amine (Intermediate 23), 3-(5-bromo-pyridin-3-yl)-benzaldehyde (Intermediate 24), [4-(5-bromo-pyridin-3-yl)-benzyl]-methyl-amine (Intermediate 72), [4-(5-bromo-pyridin-3-yl)-phenyl]-methanol (Intermediate 73), 4-(5-bromo-pyridin-3-yl)-benzylamine (Intermediate 74), 3-(5-bromo-pyridin-3-yl)-benzylamine (Intermediate 75), 4-[4-(5-bromo-pyridin-3-yl)-benzyl]-morpholine (Intermediate 76), 3-bromo-5-cyclopent-1-enyl-pyridine (Intermediate 77), 4-[3-(5-bromo-pyridin-3-yl)-benzyl]-morpholine (Intermediate 78), (5'- bromo-[3,3']bipyridinyl-5-ylmethyl)-dimethyl-amine (Intermediate 79), (5'-bromo-[3,3']bipyridinyl-5-ylmethyl)-methyl-amine (Intermediate 80), [3-(5-bromo-pyridin-3-yl)-phenyl]-methanol (Intermediate 81), 5-bromo-3',6'-dihydro-2'H-[3,4']bipyridinyl-1'-carboxylic acid tert-butyl ester (Intermediate 82), {(R)-1-[4-(5-bromo-pyridin-3-yl)-benzyl]-pyrrolidin-3-yl}-dimethyl-amine (Intermediate 83), {(S)-1-[4-(5-bromo-pyridin-3-yl)-benzyl]-pyrrolidin-3-yl}-dimethyl-amine (Intermediate 84), {1-[4-(5-bromo-pyridin-3-yl)-phenyl]-ethyl}-carbamic acid tert-butyl ester (Intermediate 85), {1-[3-(5-bromo-pyridin-3-yl)-phenyl]-1-methyl-ethyl}-carbamic acid tert-butyl ester (Intermediate 86), {1-[4-(5-bromo-pyridin-3-yl)-phenyl]-1-methyl-ethyl}-carbamic acid tert-butyl ester (Intermediate 87), 2-[3-(5-bromo-pyridin-3-yl)-phenyl]-pyrrolidine-1-carboxylic acid tert-butyl ester (Intermediate 88), 3-bromo-5-(1-methyl-1H-pyrazol-4-yl)-pyridine (Intermediate 89), {(S)-1-[4-(5-bromo-pyridin-3-yl)-phenyl]-ethyl}-carbamic acid tert-butyl ester (Intermediate 90), {(R)-1-[4-(5-bromo-pyridin-3-yl)-phenyl]-ethyl}-carbamic acid tert-butyl ester (Intermediate 91), 4-(5-bromo-pyridin-3-yl)-benzaldehyde (Intermediate 92), 1-[4-(5-bromo-pyridin-3-yl)-benzyl]-4-isopropyl-piperazine (Intermediate 93), [3-(5-bromo-pyridin-3-yl)-phenyl]-acetic acid (Intermediate 94), [4-(5-bromo-pyridin-3-yl)-phenyl]-acetic acid methyl ester (Intermediate 95), 3-[4-(5-bromo-pyridin-3-yl)-phenyl]-propionic acid methyl ester (Intermediate 96), {1-[4-(5-bromo-pyridin-3-yl)-phenyl]-1-methyl-ethyl}-dimethyl-amine (Intermediate 97), {1-[4-(5-bromo-pyridin-3-yl)-3-methyl-phenyl]-1-methyl-ethyl}-carbamic acid tert-butyl ester (Intermediate 98), {1-[4-(5-bromo-pyridin-3-yl)-2-methyl-phenyl]-1-methyl-ethyl}-carbamic acid tert-butyl ester (Intermediate 99), are prepared by an analogous method to that for 3-bromo-5-(4-methoxyphenyl)-pyridine (Intermediate 16) by replacing 4-methoxyphenylboronic acid with the corresponding boronic acid or boronic ester, namely, phenylboronic acid (Sigma-Aldrich, St. Louis, USA), 3-methoxy-phenylboronic acid (Sigma-Aldrich, St. Louis, USA), 4-fluoro-phenylboronic acid (Sigma-Aldrich, St. Louis, USA), 2-methoxy-phenylboronic acid (Sigma-Aldrich, St. Louis, USA), (4-methyl-piperazin-1-ylmethyl)-phenyl-3-boronic acid (Intermediate 7), dimethylaminomethyl-phenyl-4-boronic acid (Intermediate 14), dimethylaminomethyl-phenyl-3-boronic acid (Intermediate 10), 3-formylphenylboronic acid (ABCR GmbH & Co. KG, Karlsruhe, Germany), methylaminomethyl-phenyl-4-boronic acid (Intermediate 61), 4-(hydroxymethyl)benzene boronic acid (Sigma-Aldrich, St. Louis, USA), (4-aminomethylphenyl)boronic acid hydrochloride (ABCR GmbH & Co. KG, Karlsruhe, Germany), (3-aminomethylphenyl)boronic acid hydrochloride (ABCR GmbH & Co. KG, Karlsruhe, Germany), morpholin-4-ylmethyl-phenyl-4-boronic acid (Intermediate 15), cyclopenten-1-ylboronic acid (ABCR GmbH & Co. KG, Karlsruhe, Germany), morpholin-4-ylmethyl-phenyl-3-boronic acid (Intermediate 11), dimethyl-[5-(4,4,5,5-tetramethyl-[1,3,2]dioxaborolan-2-yl)-pyridin-3-ylmethyl]-amine (Intermediate 102), methyl-[5-(4,4,5,5-tetramethyl-[1,3,2]dioxaborolan-2-yl)-pyridin-3-ylmethyl]-amine (Intermediate 103), 3-(hydroxymethyl)phenylboronic acid (Sigma-Aldrich, St. Louis, USA), 4-(4,4,5,5-tetramethyl-[1,3,2]dioxaborolan-2-yl)-3,6-dihydro-2H-pyridine-1-carboxylic acid tert-butyl ester (ABCR GmbH & Co. KG, Karlsruhe, Germany), 4-((R)-3-dimethylamino-pyrrolidin-1-yl methyl)-benzeneboronic acid (Intermediate 62), 4-((S)-3-dimethylamino-pyrrolidin-1-ylmethyl)-benzeneboronic acid (Intermediate 63), {1-[4-(4,4,5,5-tetramethyl-[1,3,2]dioxaborolan-2-yl)-phenyl]-ethyl}-carbamic acid tert-butyl ester (Intermediate 107), {1-methyl-1-[3-(4,4,5,5-tetramethyl-[1,3,2]dioxaborolan-2-yl)-phenyl]-ethyl}-carbamic acid butyl ester (Intermediate 111), {1-methyl-1-[4-(4,4,5,5-tetramethyl-[1,3,2]dioxaborolan-2-yl)-phenyl]-ethyl}-carbamic acid butyl ester (Intermediate 104), 2-[3-(4,4,5,5-tetramethyl-[1,3,2]dioxaborolan-2-yl)-phenyl]-pyrrolidine-1-carboxylic acid tert-butyl ester (Intermediate 126), 1-methyl-4-(4,4,5,5-tetramethyl-[1,3,2]dioxaborolan-2-yl)-1H-pyrazole (Sigma-Aldrich, St. Louis, USA), {(S)-1-[4-(4,4,5,5-tetramethyl-[1,3,2]dioxaborolan-2-yl)-phenyl]-ethyl}-carbamic acid tert-butyl ester (Intermediate 142), {(R)-1-[4-(4,4,5,5-tetramethyl-[1,3,2]dioxaborolan-2-yl)-phenyl]-ethyl}-carbamic acid tert-butyl ester (Intermediate 143), 4-formylphenylboronic acid (Sigma-Aldrich, St. Louis, USA), 4-(4-isopropyl-piperazin-1-ylmethyl)-benzeneboronic acid (Intermediate 13), [3-(4,4,5,5-tetramethyl-[1,3,2]dioxaborolan-2-yl)-phenyl]-acetic acid (Frontier Scientific Ltd., Logan, USA), [4-(4,4,5,5-tetramethyl-[1,3,2]dioxaborolan-2-yl)-phenyl]-acetic acid methyl ester (J & W PharmLab LLC, Livittown, USA), [4-(2-methoxycarbonyl-ethyl)phenyl]boronic acid (ABCR GmbH & Co. KG, Karlsruhe, Germany), dimethyl-{1-methyl-1-[4-(4,4,5,5-tetramethyl-[1,3,2]dioxaborolan-2-yl)-phenyl]-ethyl}-amine (Intermediate 157), {1-methyl-1-[3-methyl-4-(4,4,5,5-tetramethyl-[1,3,2]dioxaborolan-2-yl)-phenyl]-ethyl}-carbamic acid tert-butyl ester (Intermediate 163), or {1-methyl-1-[2-methyl-4-(4,4,5,5-tetramethyl-[1,3,2]dioxaborolan-2-yl)-phenyl]-ethyl}-carbamic acid tert-butyl ester (Intermediate 164), respectively.

Intermediate 25

N-(5-Bromo-pyridin-3-yl)-propionamide

To a solution of propionic acid (Sigma-Aldrich, St. Louis, USA) (1.5 eq, 8.4 mmol, 0.63 ml) in DMF (15 ml), HOBt (1.2 eq, 6.7 mmol, 0.910 g) and EDC hydrochloride (1.5 eq, 8.4 mmol, 1.65 g) are added. The resulting mixture is stirred for 1 h at r.t. Then 3-amino-5-bromopyridine (Sigma-Aldrich, St. Louis, USA) (1 eq, 5.6 mmol, 1.00 g) and N-methyl-morpholine (3 eq, 16.8 mmol, 1.85 ml) are added and stirring is continued for 18 h at r.t. The solvents are evaporated and the residue is purified by column chromatography (hexane/EtOAc) yielding the title compound; $[M+H]^+=230$.

Intermediate 26

N-(5-Bromo-pyridin-3-yl)-3-dimethylamino-propionamide

To a solution of 3-amino-5-bromopyridine (Sigma-Aldrich, St. Louis, USA) (1 eq, 11.2 mmol, 2.00 g) and 3-dimethylaminopropionic acid hydrochloride (ABCR GmbH & Co. KG, Karlsruhe, Germany) (1 eq, 11.2 mmol, 1.74 g) in DCM (50 ml), tributylamine (3.6 eq, 40.4 mmol, 9.8 ml) and 2-chloro-1-methylpyridinium iodide (1.2 eq, 13.5 mmol, 3.54 g) are added. The resulting mixture is heated at 50° C. for 4 h, then the solvents are removed in vacuo, aqueous NaOH solution (1 M) is added, and the mixture is extracted with DCM. The organic layer is dried with $MgSO_4$, filtered, and the solvent is removed in vacuo. Purification by column chromatography (DCM/MeOH) yields the title compound; $[M+H]^+=273$.

Intermediates 27 to 31

The following intermediates, namely, N-(5-Bromo-pyridin-3-yl)-4-dimethylamino-butyramide (Intermediate 27),

[2-(5-Bromo-pyridin-3-ylcarbamoyl)-ethyl]-carbamic acid tert-butyl ester (Intermediate 28), 4-Acetylamino-N-(5-bromo-pyridin-3-yl)-butyramide (Intermediate 29), 3-Acetylamino-N-(5-bromo-pyridin-3-yl)-propionamide (Intermediate 30), 3-Benzyloxy-N-(5-bromo-pyridin-3-yl)-propionamide (Intermediate 31), are prepared by an analogous method to that for N-(5-bromo-pyridin-3-yl)-3-dimethylamino-propionamide (Intermediate 26) by replacing 3-dimethylaminopropionic acid hydrochloride with the corresponding acid hydrochloride or acid, namely, 4-(dimethylamino)butyric acid hydrochloride (Sigma-Aldrich, St. Louis, USA), N-tert-butyloxycarbonyl-beta-alanine (ABCR GmbH & Co. KG, Karlsruhe, Germany), 4-acetamidobutyric acid (ABCR GmbH & Co. KG, Karlsruhe, Germany), N-acetyl-beta-alanine (ABCR GmbH & Co. KG, Karlsruhe, Germany), or 3-benzyloxy-propionic acid (Synthetic Communicatios (1988), 18 (11), 1311-1322), respectively.

Intermediate 32

N-(5-Bromo-pyridin-3-yl)-3-hydroxy-propionamide

To a solution of 3-benzyloxy-N-(5-bromo-pyridin-3-yl)-propionamide (Intermediate 31) (1 eq, 8.1 mmol, 2.8 g) in DCM (100 ml) at 0° C., boron tribromide (1 M in DCM, 1.1 eq, 8.9 mmol, 8.9 ml) is added within 10 min. The mixture is allowed to warm up to r.t. and stirred for 1 h at this temperature. The mixture is filtered, the solid residue is washed with DCM, and dried giving the title compound; $[M+H]^+=326$.

Intermediate 33

1-(5-Bromo-pyridin-3-yl)-4-methyl-piperazine

To a solution of 3,5-dibromopyridine (Sigma-Aldrich, St. Louis, USA) (1 eq, 8.4 mmol, 2.0 g) and 1-methylpiperazine (Sigma-Aldrich, St. Louis, USA) (1 eq, 8.4 mmol, 0.94 ml) in toluene (20 ml), $Pd_2(dba)_3$ (0.02 eq, 0.167 mmol, 153 mg), Xantphos (0.06 eq, 0.50 mmol, 290 mg), and NaOtBu (1.5 eq, 12.5 mmol, 1.2 g) are added. The resulting mixture is heated using microwave radiation at 120° C. for 15 min. The solvents are evaporated and aqueous HCl solution (1 M) is added. The aqueous layer is washed with DCM, adjusted to pH 10, and extracted with DCM. The organic layer is dried, filtered, and concentrated to give the title compound, $[M+H]^+=257$.

Intermediate 34

3-Bromo-5-isopropoxy-pyridine

To NMP (15 eq, 313 mmol, 30.4 ml), NaOtBu (1.5 eq, 31.3 mmol, 3.01 g) is added portion-wise. The mixture is stirred for 1 h at r.t., then 2-propanol (15 eq, 313 mmol, 24 ml) is added over a period of 15 min, followed by the addition of 3,5-dibromopyridine (Sigma-Aldrich, St. Louis, USA) (1 eq, 20.9 mmol, 5.0 g). The resulting mixture is heated at 75° C. for 2 h. After cooling down to r.t., toluene (30 ml) is added and the mixture is washed with water, dried over $MgSO_4$, filtered, and concentrated. Purification of the crude product using column chromatography (hexane/EtOAc) yields the title compound; $[M+H]^+=217$.

Intermediate 35

Quinoline-3-boronic acid

To a solution of 3-bromoquinoline (Sigma-Aldrich, St. Louis, USA) (1 eq, 14.0 mmol, 1.94 ml) in toluene/THF (4:1, 25 ml), triisopropylborate (1.2 eq, 16.8 mmol, 3.94 ml) is added. The mixture is cooled to −40° C., then n-butyl lithium (1.6 M in THF, 1.2 eq, 17 mmol, 10.5 ml) is added within 30 min. After stirring for additional 30 min at this temperature, the cooling bath is removed and the reaction mixture is allowed to to warm up to −20° C. before quenching with aqueous HCl solution (2 N). The mixture is adjusted to pH 7 by using aqueous NaOH solution (4 N), then it is saturated with NaCl, and extracted with THF. The organic layer is concentrated in vacuo, and the resulting solid is recrystallized in MeCN yielding the title compound, $[M+H]^+=173$.

Intermediates 36 and 100

The following intermediates, namely, isoquinoline-4-boronic acid (Intermediate 36), 5-bromo-pyridine-3-boronic acid (Intermediate 100) are prepared by an analogous method to that for quinoline-3-boronic acid (Intermediate 35) by replacing 3-bromoquinoline with the corresponding bromide, namely, 4-bromoisoquinoline (Sigma-Aldrich, St. Louis, USA), or 3,5-dibromopyridine (Sigma-Aldrich, St. Louis, USA), respectively.

Intermediate 37

3-(4-Methoxy-phenyl)-5-(4,4,5,5-tetramethyl-[1,3,2]dioxaborolan-2-yl)-pyridine

To a solution of 3-bromo-5-(4-methoxy-phenyl)-pyridine (Intermediate 16) (1 eq, 3.56 mmol, 0.950 g) in MeCN (10 ml), bis-(pinacolate)-diboron (1.2 eq, 4.27 mmol, 1.11 g), KOAc (3 eq, 10.7 mmol, 1.05 g), and $Pd(dppf)Cl_2$ (0.04 eq, 0.142 mmol, 105 mg) are added. The mixture is heated using microwave radiation at 160° C. for 15 min. Filtration of the mixture gives the title compound; $[M+H]^+=312$.

Intermediates 38 to 57 and 101 to 165

The following intermediates, namely, 3-phenyl-5-(4,4,5,5-tetramethyl-[1,3,2]dioxaborolan-2-yl)-pyridine (Intermediate 38), 3-(3-methoxy-phenyl)-5-(4,4,5,5-tetramethyl-[1,3,2]dioxaborolan-2-yl)-pyridine (Intermediate 39), 3-(4-fluoro-phenyl)-5-(4,4,5,5-tetramethyl-[1,3,2]dioxaborolan-2-yl)-pyridine (Intermediate 40), 3-(2-methoxy-phenyl)-5-(4,4,5,5-tetramethyl-[1,3,2]dioxaborolan-2-yl)-pyridine (Intermediate 41), 1-methyl-4-{3-[5-(4,4,5,5-tetramethyl-[1,3,2]dioxaborolan-2-yl)-pyridin-3-yl]-benzyl}-piperazine (Intermediate 42), N-[5-(4,4,5,5-tetramethyl-[1,3,2]dioxaborolan-2-yl)-pyridin-3-yl]-propionamide (Intermediate 43), 4-dimethylamino-N-[5-(4,4,5,5-tetramethyl-[1,3,2]dioxaborolan-2-yl)-pyridin-3-yl]-butyramide (Intermediate 44), 3-dimethylamino-N-[5-(4,4,5,5-tetramethyl-[1,3,2]dioxaborolan-2-yl)-pyridin-3-yl]-propionamide (Intermediate 45), {2-[5-(4,4,5,5-tetramethyl-[1,3,2]dioxaborolan-2-yl)-pyridin-3-ylcarbamoyl]-ethyl}-carbamic acid tert-butyl ester (Intermediate 46), 4-acetylamino-N-[5-(4,4,5,5-tetramethyl-[1,3,2]dioxaborolan-2-yl)-pyridin-3-yl]-butyramide (Intermediate 47), 3-acetylamino-N-[5-(4,4,5,5-tetramethyl-[1,3,2]dioxaborolan-2-yl)-pyridin-3-yl]-propionamide (Intermediate 48), 3-hydroxy-N-[5-(4,4,5,5-tetramethyl-[1,3,2]dioxaborolan-2-yl)-pyridin-3-yl]-propionamide (Intermediate 49), 4-methyl-3-(4,4,5,5-tetramethyl-[1,3,2]dioxaborolan-2-yl)-pyridine (Intermediate 50), 1-methyl-4-[5-(4,4,5,5-tetramethyl-[1,3,2]dioxaborolan-2-yl)-pyridin-3-yl]-piperazine (Intermediate 51), 3-ethoxy-5-(4,4,5,5-tetramethyl-[1,3,2]dioxaborolan-2-yl)-pyridine (Intermediate 52), 3-isopropoxy-5-(4,4,5,5-tetramethyl-[1,3, 2]dioxaborolan-2-yl)-pyridine (Intermediate 53), dimethyl-{4-[5-(4,4,5,5-tetramethyl-[1,3,2]dioxaborolan-2-yl)-pyridin-3-yl]-benzyl}-amine (Intermediate 54), dimethyl-{3-[5-(4,4,5,5-tetramethyl-[1,3,2]dioxaborolan-2-yl)-pyridin-3-yl]-benzyl}-amine (Intermediate 55), 3-[5-(4,4,5,5-tetramethyl-[1,3,2]dioxaborolan-2-yl)-pyridin-3-yl]-benzaldehyde (Intermediate 56), [3-(4,4,5,5-tetramethyl-[1,3,2]dioxaborolan-2-yl)-phenyl]-methanol (Intermediate 57), methyl-{4-[5-(4,4,5,5-tetramethyl-[1,3,2]dioxaborolan-2-yl)-pyridin-3-yl]-benzyl}-amine (Intermediate 101), dimethyl-[5-(4,4,5,5-tetramethyl-[1,3,2]dioxaborolan-2-yl)-pyridin-3-ylmethyl]-amine (Intermediate 102), methyl-[5-(4,4,5,5-tetramethyl-[1,3,2]dioxaborolan-2-yl)-pyridin-3-ylmethyl]-amine (Intermediate 103), {1-methyl-1-[4-(4,4,5,5-tetramethyl-[1,3,2]dioxaborolan-2-yl)-phenyl]-ethyl}-carbamic butyl ester (Intermediate 104), [5-(4,4,5,5-tetramethyl-[1,3,2]dioxaborolan-2-yl)-pyridin-3-yl]-methanol (Intermediate 105), 5-(4,4,5,5-tetramethyl-[1,3,2]dioxaborolan-2-yl)-pyridin-3-ol (Intermediate 106), {1-[4-(4,4,5,5-tetramethyl-[1,3,2]dioxaborolan-2-yl)-phenyl]-ethyl}-carbamic acid tert-butyl ester (Intermediate 107), {4-[5-(4,4,5,5-tetramethyl-[1,3,2]dioxaborolan-2-yl)-pyridin-3-yl]-phenyl}-methanol (Intermediate 108), 3-[1,3,4]oxadiazol-2-yl-5-(4,4,5,5-tetramethyl-[1,3,2]dioxaborolan-2-yl)-pyridine (Intermediate 109), {4-[5-(4,4,5,5-tetramethyl-[1,3,2]dioxaborolan-2-yl)-pyridin-3-yl]-benzyl}-carbamic acid butyl ester (Intermediate 110), {1-methyl-1-[3-(4,4,5,5-tetramethyl-[1,3,2]dioxaborolan-2-yl)-phenyl]-ethyl}-carbamic acid tert-butyl ester (Intermediate 111), {3-[5-(4,4,5,5-tetramethyl-[1,3,2]dioxaborolan-2-yl)-pyridin-3-yl]-benzyl}-carbamic acid tert-butyl ester (Intermediate 112), 2-[4-(4,4,5,5-tetramethyl-[1,3,2]dioxaborolan-2-yl)-phenyl]-piperazine (Intermediate 113), 4-{4-[5-(4,4,5,5-tetramethyl-[1,3,2]dioxaborolan-2-yl)-pyridin-3-yl]-benzyl}-morpholine (Intermediate 114), 3-cyclopent-1-enyl-5-(4,4,5,5-tetramethyl-[1,3,2]dioxaborolan-2-yl)-pyridine (Intermediate 115), 4-{3-[5-(4,4,5,5-tetramethyl-[1,3,2]dioxaborolan-2-yl)-pyridin-3-yl]-benzyl}-morpholine (Intermediate 116), dimethyl-[5'-(4,4,5,5-tetramethyl-[1,3,2]dioxaborolan-2-yl)-[3,3']bipyridinyl-5-ylmethyl]-amine (Intermediate 117), methyl-[5'-(4,4,5,5-tetramethyl-[1,3,2]dioxaborolan-2-yl)-[3,3']bipyridinyl-5-ylmethyl]-amine (Intermediate 118), {3-[5-(4,4,5,5-tetramethyl-[1,3,2]dioxaborolan-2-yl)-pyridin-3-yl]-phenyl}-methanol (Intermediate 119), 3-methylsulfanyl-5-(4,4,5,5-tetramethyl-[1,3,2]dioxaborolan-2-yl)-pyridine (Intermediate 120), [5-(4,4,5,5-tetramethyl-[1,3,2]dioxaborolan-2-yl)-pyridin-3-yl]-carbamic acid tert-butyl ester (Intermediate 121), 3-methyl-5-(4,4,5,5-tetramethyl-[1,3,2]dioxaborolan-2-yl)-pyridine (Intermediate 122), 5-(4,4,5,5-tetramethyl-[1,3,2]dioxaborolan-2-yl)-nicotinonitrile (Intermediate 123), 2-[3-(4,4,5,5-tetramethyl-[1,3,2]dioxaborolan-2-yl)-phenyl]-piperazine (Intermediate 124), 5-(4,4,5,5-tetramethyl-[1,3,2]dioxaborolan-2-yl)-3',6'-dihydro-2'H-[3,4']bipyridinyl-1'-carboxylic acid tert-butyl ester (Intermediate 125), 2-[3-(4,4,5,5-tetramethyl-[1,3,2]dioxaborolan-2-yl)-phenyl]-pyrrolidine-1-carboxylic acid tert-butyl ester (Intermediate 126), 1-[5-(4,4,5,5-tetramethyl-[1,3,2]dioxaborolan-2-yl)-3',6'-dihydro-2'H-[3,4']bipyridinyl-1'-yl]-ethanone (Intermediate 127), dimethyl-((R)-1-{4-[5-(4,4,5,5-tetramethyl-[1,3,2]dioxaborolan-2-yl)-pyridin-3-yl]-benzyl}-pyrrolidin-3-yl)-amine (Intermediate 128), dimethyl-((S)-1-{4-[5-(4,4,5,5-tetramethyl-[1,3,2]dioxaborolan-2-yl)-pyridin-3-yl]-benzyl}-pyrrolidin-3-yl)-amine (Intermediate 129), (1-{4-[5-(4,4,5,5-tetramethyl-[1,3,2]dioxaborolan-2-yl)-pyridin-3-yl]-phenyl}-ethyl)-carbamic acid tert-butyl ester (Intermediate 130), (1-methyl-1-{3-[5-(4,4,5,5-tetramethyl-[1,3,2]dioxaborolan-2-yl)-pyridin-3-yl]-phenyl}-ethyl)-carbamic acid tert-butyl ester (Intermediate 131), (1-methyl-1-{4-[5-(4,4,5,5-tetramethyl-[1,3,2]dioxaborolan-2-yl)-pyridin-3-yl]-phenyl}-ethyl)-carbamic acid tert-butyl ester (Intermediate 132), 6-(4,4,5,5-tetramethyl-[1,3,2]dioxaborolan-2-yl)-3,4-dihydro-1H-isoquinoline-2-carboxylic acid tert-butyl ester (Intermediate 133), 1'-methyl-5-(4,4,5,5-tetramethyl-[1,3,2]dioxaborolan-2-yl)-1',2',3',6'-tetrahydro[3,4']bipyridinyl (Intermediate 134), 7-(4,4,5,5-tetramethyl-[1,3,2]dioxaborolan-2-yl)-3,4-dihydro-1H-isoquinoline-2-carboxylic acid tert-butyl ester (Intermediate 135), 2-{3-[5-(4,4,5,5-tetramethyl-[1,3,2]dioxaborolan-2-yl)-pyridin-3-yl]-phenyl}-pyrrolidine-1-carboxylic acid tert-butyl ester (Intermediate 136), 3-(1-methyl-1H-pyrazol-4-yl)-5-(4,4,5,5-tetramethyl-[1,3,2]dioxaborolan-2-yl)-pyridine (Intermediate 137), dimethyl-[5'-(4,4,5,5-tetramethyl-[1,3,2]dioxaborolan-2-yl)-[2,3']bipyridinyl-5-ylmethyl]-amine (Intermediate 138), 5-(4,4,5,5-tetramethyl-[1,3,2]dioxaborolan-2-yl)-3,4-dihydro-2H-pyrano[2,3-c]pyridine (Intermediate 139), ((S)-1-{4-[5-(4,4,5,5-tetramethyl-[1,3,2]dioxaborolan-2-yl)-pyridin-3-yl]-phenyl}-ethyl)-carbamic acid tert-butyl ester (Intermediate 140), ((R)-1-{4-[5-(4,4,5,5-tetramethyl-[1,3,2]dioxaborolan-2-yl)-pyridin-3-yl]-phenyl}-ethyl)-carbamic acid tert-butyl ester (Intermediate 141), {(S)-1-[4-(4,4,5,5-tetramethyl-[1,3,2]dioxaborolan-2-yl)-phenyl]-ethyl}-carbamic acid tert-butyl ester (Intermediate 142), {(R)-1-[4-(4,4,5,5-tetramethyl-[1,3,2]dioxaborolan-2-yl)-phenyl]-ethyl}-carbamic acid tert-butyl ester (Intermediate 143), 1-methyl-4-{3-[5-(4,4,5,5-tetramethyl-[1,3,2]dioxaborolan-2-yl)-pyridin-3-yl]-prop-2-ynyl}-piperazine (Intermediate 144), (tert-butoxycarbonyl-{3-[5-(4,4,5,5-tetramethyl-[1,3,2]dioxaborolan-2-yl)-pyridin-3-yl]-benzyl}-amino)-acetic acid methyl ester (Intermediate 145), 4-[5-(4,4,5,5-tetramethyl-[1,3,2]dioxaborolan-2-yl)-pyridin-3-yl]-benzaldehyde (Intermediate 146), 1-isopropyl-4-{4-[5-(4,4,5,5-tetramethyl-[1,3,2]dioxaborolan-2-yl)-pyridin-3-yl]-benzyl}-piperazine (Intermediate 147), (methyl-{3-[5-(4,4,5,5-tetramethyl-[1,3,2]dioxaborolan-2-yl)-pyridin-3-yl]-benzyl}-amino)-acetic acid methyl ester (Intermediate 148), (tert-butoxycarbonyl-{4-[5-(4,4,5,5-tetramethyl-[1,3,2]dioxaborolan-2-yl)-pyridin-3-yl]-benzyl}-amino)-acetic acid methyl ester (Intermediate 149), (methyl-{4-[5-(4,4,5,5-tetramethyl-[1,3,2]dioxaborolan-2-yl)-pyridin-3-yl]-benzyl}-amino)-acetic acid methyl ester (Intermediate 150), 3-[3-(3,3-difluoro-pyrrolidin-1-yl)-prop-1-ynyl]-5-(4,4,5,5-tetramethyl-[1,3,2]dioxaborolan-2-yl)-pyridine (Intermediate 151), {3-[5-(4,4,5,5-tetramethyl-[1,3,2]dioxaborolan-2-yl)-pyridin-3-yl]-phenyl}-acetic acid methyl ester (Intermediate 152), {4-[5-(4,4,5,5-tetramethyl-[1,3,2]dioxaborolan-2-yl)-pyridin-3-yl]-phenyl}-acetic acid methyl ester (Intermediate 153), 4-{3-[5-(4,4,5,5-tetramethyl-[1,3,2]dioxaborolan-2-yl)-pyridin-3-yl]-prop-2-ynyl}-morpholine (Intermediate 154), 3-{4-[5-(4,4,5,5-tetramethyl-[1,3,2]dioxaborolan-2-yl)-pyridin-3-yl]-phenyl}-propionic acid methyl ester (Intermediate 155), dimethyl-(1-methyl-1-{4-[5-(4,4,5,5-tetramethyl-[1,3,2]dioxaborolan-2-yl)-pyridin-3-yl]-phenyl}-ethyl)-amine (Intermediate 156), dimethyl-{1-methyl-1-[4-(4,4,5,5-tetramethyl-[1,3,2]dioxaborolan-2-yl)-phenyl]-ethyl}-amine (Intermediate 157), 4-(1-methyl-1-{4-[5-(4,4,5,5-tetramethyl-[1,3,2]dioxaborolan-2-yl)-pyridin-3-yl]-phenyl}-ethyl)-morpholine (Intermediate 158), 2-(1-methyl-1-{4-[5-(4,4,5,5-tetramethyl-[1,3,2]dioxaborolan-2-yl)-pyridin-3-yl]-phenyl}-ethylamino)-ethanol (Intermediate 159), 2-[methyl-(1-methyl-1-{4-[5-(4,4,5,5-tetramethyl-[1,3,2]dioxaborolan-2-yl)-pyridin-3-yl]-phenyl}-ethyl)-amino]-ethanol (Intermediate 160), (1-methyl-1-{3-methyl-4-[5-(4,4,5,5-tetramethyl-[1,3,2]dioxaborolan-2- yl)-pyridin-3-yl]-phenyl}-ethyl)-carbamic acid tert-butyl ester (Intermediate 161), (1-methyl-1-{2-methyl-4-[5-(4,4,5,5-tetramethyl-[1,3,2]dioxaborolan-2-yl)-pyridin-3-yl]-phenyl}-ethyl)-carbamic acid tert-butyl ester (Intermediate 162), {1-methyl-1-[3-methyl-4-(4,4,5,5-tetramethyl-[1,3,2]dioxaborolan-2-yl)-phenyl]-ethyl}-carbamic acid tert-butyl ester (Intermediate 163), {1-methyl-1-[2-methyl-4-(4,4,5,5-tetramethyl-[1,3,2]dioxaborolan-2-yl)-phenyl]-ethyl}-carbamic acid tert-butyl ester (Intermediate 164), dimethyl-{3-[5-(4,4,5,5-tetramethyl-[1,3,2]dioxaborolan-2-yl)-pyridin-3-yl]-prop-2-ynyl}-amine (Intermediate 165), are prepared by an analogous method to that for 3-(4-methoxy-phenyl)-5-(4,4,5,5-tetramethyl-[1,3,2]dioxaborolan-2-yl)-pyridine (Intermediate 37) by replacing 3-bromo-5-(4-methoxy-phenyl)-pyridine (Intermediate 16) with the corresponding bromide, namely, 3-bromo-5-phenyl-pyridine (Intermediate 17), 3-bromo-5-(3-methoxy-phenyl)-pyridine (Intermediate 18), 3-bromo-5-(4-fluoro-phenyl)-pyridine (Intermediate 19), 3-bromo-5-(2-methoxy-phenyl)-pyridine (Intermediate 20), 1-[3-(5-bromo-pyridin-3-yl)-benzyl]-4-methyl-piperazine (Intermediate 21), N-(5-bromo-pyridin-3-yl)-propionamide (Intermediate 25), N-(5-bromo-pyridin-3-yl)-4-dimethylamino-butyramide (Intermediate 27), N-(5-bromo-pyridin-3-yl)-3-dimethylamino-propionamide (Intermediate 26), [2-(5-bromo-pyridin-3-ylcarbamoyl)-ethyl]-carbamic acid tert-butyl ester (Intermediate 28), 4-acetylamino-N-(5-bromo-pyridin-3-yl)-butyramide (Intermediate 29), 3-acetylamino-N-(5-bromo-pyridin-3-yl)-propionamide (Intermediate 30), N-(5-bromo-pyridin-3-yl)-3-hydroxy-propionamide (Intermediate 32), 3-bromo-4-methyl-pyridine (Sigma-Aldrich, St. Louis, USA), 1-(5-bromo-pyridin-3-yl)-4-methyl-piperazine (Intermediate 33), 3-bromo-5-ethoxy-pyridine (Fulcrum Scientific Ltd., Huddersfield, UK), 3-bromo-5-isopropoxy-pyridine (Intermediate 34), [4-(5-bromo-pyridin-3-yl)-benzyl]-dimethyl-amine (Intermediate 22), [3-(5-bromo-pyridin-3-yl)-benzyl]-dimethyl-amine (Intermediate 23), 3-(5-bromo-pyridin-3-yl)-benzaldehyde (Intermediate 24), or (3-bromo-phenyl)-methanol (Sigma-Aldrich, St. Louis, USA) [4-(5-bromo-pyridin-3-yl)-benzyl]-methyl-amine (Intermediate 72), (5-bromo-pyridin-3-ylmethyl)-dimethyl-amine (Intermediate 64), (5-bromo-pyridin-3-ylmethyl)-methyl-amine (Maybridge Chemical Co. Ltd., Cornwall, UK), [1-(4-bromo-phenyl)-1-methyl-ethyl]-carbamic acid tert-butyl ester (Intermediate 201), (5-bromo-pyridin-3-yl)-methanol (Maybridge Chemical Co. Ltd., Cornwall, UK), 5-bromo-pyridin-3-ol (Sigma-Aldrich, St. Louis, USA), [1-(4-bromo-phenyl)-ethyl]-carbamic acid tert-butyl ester (Intermediate 202), [4-(5-bromo-pyridin-3-yl)-phenyl]-methanol (Intermediate 73), 3-bromo-5-[1,3,4]oxadiazol-2-yl-pyridine (Apollo Scientific Ltd., Bredbury, UK), [4-(5-bromo-pyridin-3-yl)-benzyl]-carbamic acid tert-butyl ester (Intermediate 203), [1-(3-bromo-phenyl)-1-methyl-ethyl]-carbamic acid tert-butyl ester (Intermediate 204), [3-(5-bromo-pyridin-3-yl)-benzyl]-carbamic acid tert-butyl ester (Intermediate 205), 2-(4-bromo-phenyl)-piperazine (Sigma-Aldrich, St. Louis, USA), 4-[4-(5-bromo-pyridin-3-yl)-benzyl]-morpholine (Intermediate 76), 3-bromo-5-cyclopent-1-enyl-pyridine (Intermediate 77), 4-[3-(5-bromo-pyridin-3-yl)-benzyl]-morpholine (Intermediate 78), (5'-bromo-[3,3']bipyridinyl-5-ylmethyl)-dimethyl-amine (Intermediate 79), (5'-bromo-[3,3']bipyridinyl-5-ylmethyl)-methyl-amine (Intermediate 80), [3-(5-bromo-pyridin-3-yl)-phenyl]-methanol (Intermediate 81), 3-bromo-5-(methylthio)pyridine (Apollo Scientific Ltd., Bredbury, UK), (5-bromo-pyridin-3-yl)-carbamic acid tert-butyl ester (Intermediate 212), 3-bromo-5-methylpyridine (Sigma-Aldrich, St. Louis, USA), 3-bromonicotinonitrile (ABCR GmbH & Co. KG, Karlsruhe, Germany), 2-(3-bromo-phenyl)-piperazine (Fluorochem Ltd, Old Glossop, UK), 5-bromo-3',6'-dihydro-2'H-[3,4']bipyridinyl-1'-carboxylic acid tert-butyl ester (Intermediate 82) 2-(3-bromo-phenyl)-pyrrolidine-1-carboxylic acid tert-butyl ester (Intermediate 213), 1-(5-bromo-3',6'-dihydro-2'H-[3,4'] bipyridinyl-1'-yl)-ethanone (Intermediate 215), {(R)-1-[4-(5-bromo-pyridin-3-yl)-benzyl]-pyrrolidin-3-yl}-dimethyl-amine (Intermediate 83), {(S)-1-[4-(5-bromo-pyridin-3-yl)-benzyl]-pyrrolidin-3-yl}-dimethyl-amine (Intermediate 84), {1-[4-(5-bromo-pyridin-3-yl)-phenyl]-ethyl}-carbamic acid tert-butyl ester (Intermediate 85), {1-[3-(5-bromo-pyridin-3-yl)-phenyl]-1-methyl-ethyl}-carbamic acid tert-butyl ester (Intermediate 86), {1-[4-(5-bromo-pyridin-3-yl)-phenyl]-1-methyl-ethyl}-carbamic acid tert-butyl ester (Intermediate 87), 6-bromo-3,4-dihydro-1H-isoquinoline-2-carboxylic acid tert-butyl ester (ASW MedChem Inc., New Brunswick, USA), 5-bromo-1'-methyl-1',2',3',6'-tetrahydro-[3,4']bipyridinyl (Intermediate 66), 7-bromo-3,4-dihydro-1H-isoquinoline-2-carboxylic acid tert-butyl ester (ASW MedChem Inc., New Brunswick, USA), 2-[3-(5-bromo-pyridin-3-yl)-phenyl]-pyrrolidine-1-carboxylic acid tert-butyl ester (Intermediate 88), 3-bromo-5-(1-methyl-1H-pyrazol-4-yl)-pyridine (Intermediate 89), (5'-bromo-[2,3']bipyridinyl-5-ylmethyl)-dimethyl-amine (Intermediate 220), 5-bromo-3,4-dihydro-2H-pyrano[2,3-c]pyridine (Intermediate 221), {(S)-1-[4-(5-bromo-pyridin-3-yl)-phenyl]-ethyl}-carbamic acid tert-butyl ester (Intermediate 90), {(R)-1-[4-(5-bromo-pyridin-3-yl)-phenyl]-ethyl}-carbamic acid tert-butyl ester (Intermediate 91), [(S)-1-(4-bromo-phenyl)-ethyl]-carbamic acid tert-butyl ester (Intermediate 206), [(R)-1-(4-bromo-phenyl)-ethyl]-carbamic acid tert-butyl ester (Intermediate 207), 1-[3-(5-bromo-pyridin-3-yl)-prop-2-ynyl]-4-methyl-piperazine (Intermediate 217), {[3-(5-bromo-pyridin-3-yl)-benzyl]-tert-butoxycarbonyl-amino}-acetic acid methyl ester (Intermediate 208), 4-(5-bromo-pyridin-3-yl)-benzaldehyde (Intermediate 92), 1-[4-(5-bromo-pyridin-3-yl)-benzyl]-4-isopropyl-piperazine (Intermediate 93), {[3-(5-bromo-pyridin-3-yl)-benzyl]-methyl-amino}-acetic acid methyl ester (Intermediate 69), {[4-(5-bromo-pyridin-3-yl)-benzyl]tert-butoxycarbonyl-amino}-acetic acid methyl ester (Intermediate 209), {[4-(5-bromo-pyridin-3-yl)-benzyl]-methyl-amino}-acetic acid methyl ester (Intermediate 70), 3-bromo-5-[3-(3,3-difluoro-pyrrolidin-1-yl)-prop-1-ynyl]-pyridine (Intermediate 224), [3-(5-bromo-pyridin-3-yl)-phenyl]-acetic acid methyl ester (Intermediate 227), [4-(5-bromo-pyridin-3-yl)-phenyl]-acetic acid methyl ester (Intermediate 95), 4-[3-(5-bromo-pyridin-3-yl)-prop-2-ynyl]-morpholine (Intermediate 225), 3-[4-(5-bromo-pyridin-3-yl)-phenyl]-propionic acid methyl ester (Intermediate 96), {1-[4-(5-bromo-pyridin-3-yl)-phenyl]-1-methyl-ethyl}-dimethyl-amine (Intermediate 97), [1-(4-bromo-phenyl)-1-methyl-ethyl]-dimethyl-amine (Intermediate 228), 4-{1-[4-(5-bromo-pyridin-3-yl)-phenyl]-1-methyl-ethyl}-morpholine (Intermediate 230), 2-{1-[4-(5-bromo-pyridin-3-yl)-phenyl]-1-methyl-ethylamino}-ethanol (Intermediate 231), 2-({1-[4-(5-bromo-pyridin-3-yl)-phenyl]-1-methyl-ethyl}-methyl-amino)-ethanol (Intermediate 71), {1-[4-(5-bromo-pyridin-3-yl)-3-methyl-phenyl]-1-methyl-ethyl}-carbamic acid tert-butyl ester (Intermediate 98), {1-[4-(5-bromo-pyridin-3-yl)-2-methyl-phenyl]-1-methyl-ethyl}-carbamic acid tert-butyl ester (Intermediate 99), [1-(4-bromo-3-methyl-phenyl)-1-methyl-ethyl]-carbamic acid tert-butyl ester (Intermediate 210), [1-(4-bromo-2-methyl-phenyl)-1-methyl-ethyl]-carbamic acid tert-butyl ester (Intermediate 211), or [3-(5-bromo-pyridin-3-yl)-prop-2-ynyl]-dimethyl-amine (Intermediate 226), respectively.

Intermediate 58

4-{5-[2-(6-Methyl-pyridin-2-yl)-7H-pyrrolo[2,3-d]pyrimidin-4-yl]-pyridin-3-yl}-benzaldehyde is prepared by an analogous method to that for (4-methyl-piperazin-1-yl)-(4-{5-[2-(6-methyl-pyridin-2-yl)-7H-pyrrolo[2,3-d]pyrimidin-4-yl]-pyridin-3-yl}-phenyl)-methanone (Example 9) (Route C) by replacing 4-(4-methylpiperazine-1-carbonyl)phenylboronic acid pinacol ester (ABCR GmbH & Co. KG, Karlsruhe, Germany) with 4-formylphenylboronic acid (Sigma-Aldrich, St. Louis, USA).

Intermediates 166 to 171

The following intermediates, namely, [1-methyl-1-(4-{5-[2-(6-methyl-pyridin-2-yl)-7H-pyrrolo[2,3-d]pyrimidin-4-yl]-pyridin-3-yl}-phenyl)-ethyl]-carbamic acid tert-butyl ester (Intermediate 166), [1-(4-{5-[2-(6-methyl-pyridin-2-yl)-7H-pyrrolo[2,3-d]pyrimidin-4-yl]-pyridin-3-yl}-phenyl)-ethyl]-carbamic acid tert-butyl ester (Intermediate 169), [1-methyl-1-(3-{5-[2-(6-methyl-pyridin-2-yl)-7H-pyrrolo[2,3-d]pyrimidin-4-yl]-3-yl}-henyl)-ethyl]-carbamic acid tert-butyl ester (Intermediate 168), 2-(3-{5-[2-(6-methyl-pyridin-2-yl)-7H-pyrrolo[2,3-d]pyrimidin-4-yl]-pyridin-3-yl}-phenyl)-pyrrolidine-1-carboxylic acid tert-butyl ester (Intermediate 169), 6-{5-[2-(6-methyl-pyridin-2-yl)-7H-pyrrolo[2,3-d]pyrimidin-4-yl]-pyridin-3-yl}-3,4-dihydro-1H-isoquinoline-2-carboxylic acid tert-butyl ester (Intermediate 170), 7-{5-[2-(6-methyl-pyridin-2-yl)-7H-pyrrolo[2,3-d]pyrimidin-4-yl]-pyridin-3-yl}-3,4-dihydro-1H-isoquinoline-2-carboxylic acid tert-butyl ester (Intermediate 171), are prepared by an analogous method to that 4-{5-[2-(6-methyl-pyridin-2-yl)-7H-pyrrolo[2,3-d]pyrimidin-4-yl]-pyridin-3-yl}-benzaldehyde (Intermediate 58) by replacing 4-formylphenylboronic acid (Sigma-Aldrich, St. Louis, USA) with the corresponding boronic acid or boronic ester, namely, {1-methyl-1-[4-(4,4,5,5-tetramethyl-[1,3,2]dioxaborolan-2-yl)-phenyl]-ethyl}-carbamic acid tert-butyl ester (Intermediate 104), {1-[4-(4,4,5,5-tetramethyl-[1,3,2]dioxaborolan-2-yl)-phenyl]-ethyl}-carbamic acid tert-butyl ester (Intermediate 107), {1-methyl-1-[3-(4,4,5,5-tetramethyl-[1,3,2]dioxaborolan-2-yl)-phenyl]-ethyl}-carbamic acid tert-butyl ester (Intermediate 111), 2-[3-(4,4,5,5-tetramethyl-[1,3,2]dioxaborolan-2-yl)-phenyl]-pyrrolidine-1-carboxylic acid tert-butyl ester (Intermediate 126), 6-(4,4,5,5-tetramethyl-[1,3,2]dioxaborolan-2-yl)-3,4-dihydro-1H-isoquinoline-2-carboxylic acid tert-butyl ester (Intermediate 133), or 7-(4,4,5,5-tetramethyl-[1,3,2]dioxaborolan-2-yl)-3,4-dihydro-1H-isoquinoline-2-carboxylic acid tert-butyl ester (Intermediate 135), respectively.

Intermediate 59

(2-{5-[2-(6-Methyl-pyridin-2-yl)-7H-pyrrolo[2,3-d]pyrimidin-4-yl]-pyridin-3-ylcarbonyl}-ethyl)-carbamic acid tert-butyl ester is prepared by an analogous method to that for 2-(6-methyl-pyridin-2-yl)-4-pyridin-3-yl-7H-pyrrolo[2,3-d]pyrimidine (Example 2) (Route A) by replacing pyridine-3-boronic acid (ABCR GmbH & Co. KG, Karlsruhe, Germany) with {2-[5-(4,4,5,5-tetramethyl-[1,3,2]dioxaborolan-2-yl)-pyridin-3-ylcarbamoyl]-ethyl}-carbamic acid tert-butyl ester (Intermediate 46).

Intermediates 172 to 174

The following intermediates, namely, {5-[2-(6-methyl-pyridin-2-yl)-7H-pyrrolo[2,3-d]pyrimidin-4-yl]-pyridin-3-yl}-carbamic acid ter-butyl ester (Intermediate 172), 5-[2-(6-methyl-pyridin-2-yl)-7H-pyrrolo[2,3-d]pyrimidin-4-yl]-3',6'-dihydro-2'H-[3,4']bipyridinyl-1'-carboxylic acid tert-butyl ester (Intermediate 173), [methyl-(3-{5-[2-(6-methyl-pyridin-2-yl)-7H-pyrrolo[2,3-d]pyrimidin-4-yl]-pyridin-3-yl}-benzyl)-amino]-acetic acid methyl ester (Intermediate 174), are prepared by an analogous method to that (2-{5-[2-(6-methyl-pyridin-2-yl)-7H-pyrrolo[2,3-d]pyrimidin-4-yl]-pyridin-3-ylcarbamoyl}-ethyl)-carbamic acid tert-butyl ester (Intermediate 59) by replacing {2-[5-(4,4,5,5-tetramethyl-[1,3,2]dioxaborolan-2-yl)-pyridin-3-ylcarbamoyl]-ethyl}-carbamic acid tert-butyl ester (Intermediate 46) with the corresponding boronic acid or boronic ester, namely, [5-(4,4,5,5-tetramethyl-[1,3,2]dioxaborolan-2-yl)-pyridin-3-yl]-carbamic acid tert-butyl ester (Intermediate 121), 5-(4,4,5,5-tetramethyl-[1,3,2]dioxaborolan-2-yl)-3',6'-dihydro-2'H-[3,4']bipyridinyl-1'-carboxylic acid tert-butyl ester (Intermediate 125), or (methyl-{3-[5-(4,4,5,5-tetramethyl-[1,3,2]dioxaborolan-2-yl)-pyridin-3-yl]-benzyl}-amino)-acetic acid methyl ester (Intermediate 148), respectively.

Intermediate 60

3-{5-[6-(6-Methyl-pyridin-2-yl)-1H-pyrrolo[2,3-b]pyridin-4-yl]-pyridin-3-yl}-benzaldehyde is prepared by an analogous method to that for 6-(6-methyl-pyridin-2-yl)-4-pyridin-3-yl-1H-pyrrolo[2,3-b]pyridine (Example 46) (Route A) by replacing pyridine-3-boronic acid (ABCR GmbH & Co. KG, Karlsruhe, Germany) with 3-[5-(4,4,5,5-tetramethyl-[1,3,2]dioxaborolan-2-yl)-pyridin-3-yl]-benzaldehyde (Intermediate 56).

Intermediates 175 to 190

The following intermediates, namely, (4-{5-[6-(6-methyl-pyridin-2-yl)-1H-pyrrolo[2,3-b]pyridin-4-yl]-pyridin-3-yl}-benzyl)-carbamic acid tert-butyl ester (Intermediate 175), (3-{5-[6-(6-methyl-pyridin-2-yl)-1H-pyrrolo[2,3-b]pyridin-4-yl]-pyridin-3-yl}-benzyl)-carbamic acid tert-butyl ester (Intermediate 176), {5-[6-(6-methyl-pyridin-2-yl)-1H-pyrrolo[2,3-b]pyridin-4-yl]-pyridin-3-yl}-carbamic acid tert-butyl ester (Intermediate 177), 5-[6-(6-methyl-pyridin-2-yl)-1H-pyrrolo[2,3-b]pyridin-4-yl]-3',6'-dihydro-2'H-[3,4']bipyridinyl-1'-carboxylic acid tert-butyl ester (Intermediate 178), [1-(4-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 179), [1-methyl-1-(3-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 180), [1-methyl-1-(4-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 181), 2-(3-{5-[6-(6-methyl-pyridin-2-yl)-1H-pyrrolo[2,3-b]pyridin-4-yl]-pyridin-3-yl}-phenyl)-pyrrolidine-1-carboxylic acid tert-butyl ester (Intermediate 182), [(S)-1-(4-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 183), [(R)-1-(4-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 184), 4-{5-[6-(6-methyl-pyridin-2-yl)-1H-pyrrolo[2,3-b]pyridin-4-yl]-pyridin-3-yl}-benzaldehyde (Intermediate 185), (3-{5-[6-(6-methyl-pyridin-2-yl)-1H-pyrrolo[2,3-b]pyridin-4-yl]-pyridin-3-yl}-phenyl)-acetic acid methyl ester (Intermediate 186), (4-{5-[6-(6-methyl-pyridin-2-yl)-1H-pyrrolo[2,3-b]pyridin-4-yl]-pyridin-3-yl}-phenyl)-acetic acid methyl ester (Intermediate 187), 3-(4-{5-[6-(6-methyl-pyridin-2-yl)-1H-pyrrolo[2,3-b]

pyridin-4-yl]-pyridin-3-yl}-phenyl)-propionic acid methyl ester (Intermediate 188), [1-methyl-1-(3-methyl-4-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 189), [1-methyl-1-(2-methyl-4-{5-[6-(6-methyl-pyridin-2-yl)-1H-pyrrolo[2,3-b]pyridin-4-yl]-pyridin-3-yl}-phenyl)-ethyl]-carbamic acid tert-butyl ester (Intermediate 190), are prepared by an analogous method to that 3-{5-[6-(6-Methyl-pyridin-2-yl)-1H-pyrrolo[2,3-b]pyridin-4-yl]-pyridin-3-yl}-benzaldehyde (Intermediate 60) by replacing 3-[5-(4,4,5,5-tetramethyl-[1,3,2]dioxaborolan-2-yl)-pyridin-3-yl]-benzaldehyde (Intermediate 56) with the corresponding boronic acid or boronic ester, namely, {4-[5-(4,4,5,5-tetramethyl-[1,3,2]dioxaborolan-2-yl)-pyridin-3-yl]-benzyl}-carbamic acid tert-butyl ester (Intermediate 110), {3-[5-(4,4,5,5-tetramethyl-[1,3,2]dioxaborolan-2-yl)-pyridin-3-yl]-benzyl}-carbamic acid tert-butyl ester (Intermediate 112), [5-(4,4,5,5-tetramethyl-[1,3,2]dioxaborolan-2-yl)-pyridin-3-yl]-carbamic acid tert-butyl ester (Intermediate 121), 5-(4,4,5,5-tetramethyl-[1,3,2]dioxaborolan-2-yl)-3',6'-dihydro-2'H-[3,4']bipyridinyl-1'-carboxylic acid tert-butyl ester (Intermediate 125), (1-{4-[5-(4,4,5,5-tetramethyl-[1,3,2]dioxaborolan-2-yl)-pyridin-3-yl]-phenyl}-ethyl)-carbamic acid tert-butyl ester (Intermediate 130), (1-methyl-1-{3-[5-(4,4,5,5-tetramethyl-[1,3,2]dioxaborolan-2-yl)-pyridin-3-yl]-phenyl}-ethyl)-carbamic acid tert-butyl ester (Intermediate 131), (1-methyl-1-{4-[5-(4,4,5,5-tetramethyl-[1,3,2]dioxaborolan-2-yl)-pyridin-3-yl]-phenyl}-ethyl)-carbamic acid tert-butyl ester (Intermediate 132), 2-{3-[5-(4,4,5,5-tetramethyl-[1,3,2]dioxaborolan-2-yl)-pyridin-3-yl]-phenyl}-pyrrolodine-1-carboxylic acid tert-butyl ester (Intermediate 136), ((S)-1-{4-[5-(4,4,5,5-tetramethyl-[1,3,2]dioxaborolan-2-yl)-pyridin-3-yl]-phenyl}-ethyl)-carbamic acid tert-butyl ester (Intermediate 140), ((R)-1-{4-[5-(4,4,5,5-tetramethyl-[1,3,2]dioxaborolan-2-yl)-pyridin-3-yl]-phenyl}-ethyl)-carbamic acid tert-butyl ester (Intermediate 141), 4-[5-(4,4,5,5-tetramethyl-[1,3,2]dioxaborolan-2-yl)-pyridin-3-yl]-benzaldehyde (Intermediate 146), {3-[5-(4,4,5,5-tetramethyl-[1,3,2]dioxaborolan-2-yl)-pyridin-3-yl]-phenyl}-acetic acid methyl ester (Intermediate 152), {4-[5-(4,4,5,5-tetramethyl-[1,3,2]dioxaborolan-2-yl)-pyridin-3-yl]-phenyl}-acetic acid methyl ester (Intermediate 153), 3-{4-[5-(4,4,5,5-tetramethyl-[1,3,2]dioxaborolan-2-yl)-pyridin-3-yl]-phenyl}-propionic acid methyl ester (Intermediate 155), (1-methyl-1-{3-methyl-4-[5-(4,4,5,5-tetramethyl-[1,3,2]dioxaborolan-2-yl)-pyridin-3-yl]-phenyl}-ethyl)-carbamic acid tert-butyl ester (Intermediate 161), or (1-methyl-1-{2-methyl-4-[5-(4,4,5,5-tetramethyl-[1,3,2]dioxaborolan-2-yl)-pyridin-3-yl]-phenyl}-ethyl)-carbamic acid tert-butyl ester (Intermediate 162), respectively.

Intermediates 191 and 192

[tert-Butoxycarbonyl-(3-{5-[6-(6-methyl-pyridin-2-yl)-1H-pyrrolo[2,3-b]pyridin-4-yl]-pyridin-3-yl}-benzyl)-amino]-acetic acid (Intermediate 191) and [tert-Butoxycarbonyl-(3-{5-[6-(6-methyl-pyridin-2-yl)-1H-pyrrolo[2,3-b]pyridin-4-yl]-pyridin-3-yl}-benzyl)-amino]-acetic acid methyl ester (Intermediate 192) 4-Chloro-6-(6-methyl-pyridin-2-yl)-1H-pyrrolo[2,3-b]pyridine (Intermediate 6) (1 eq, 3.08 mmol, 750 mg) and (tert-butoxycarbonyl-{3-[5-(4,4,5,5-tetramethyl-[1,3,2]dioxaborolan-2-yl)-pyridin-3-yl]-benzyl}-amino)-acetic acid methyl ester (Intermediate 145) (1 eq, 3.08 mmol, 1.49 g) are dissolved in DME/EtOH (1:1, 8 ml). Then an aqueous $Na_2CO_3$ solution (2 M, 2 eq, 6.16 mmol, 3.08 ml) and $Pd(PPh_3)_4$ (0.05 eq, 0.154 mmol, 178 mg) are added and the resulting mixture is heated using microwave radiation at 130° C. for 20 min. The solvents are removed in vacuo, then sat. aqueous $NaHCO_3$ solution is added, and the mixture is extracted with DCM. The organic layer is dried with $MgSO_4$, filtered, and concentrated. The crude product is purified by column chromatography (DCM/MeOH 21:1, then DCM/MeOH/$NH_3$ 100:300:1) yielding the pure methyl ester and the acid, respectively; $[M+H]^+$ (ester)= 564, $[M+H]^+$ (acid)=550.

Intermediates 193 and 194

[tert-Butoxycarbonyl-(3-{5-[2-(6-methyl-pyridin-2-yl)-7H-pyrrolo[2,3-d]pyrimidin-4-yl]-pyridin-3-yl}-benzyl)-amino]-acetic acid methyl ester (Intermediate 193) and [tert-Butoxycarbonyl-(3-{5-[2-(6-methyl-pyridin-2-yl)-7H-pyrrolo[2,3-d]pyrimidin-4-yl]-pyridin-3-yl}-benzyl)-amino]-acetic acid (Intermediate 194) are prepared by an analogous method to that for [tert-butoxycarbonyl-(3-{5-[6-(6-methyl-pyridin-2-yl)-1H-pyrrolo[2,3-b]pyridin-4-yl]-pyridin-3-yl}-benzyl)-amino]-acetic acid (Intermediate 191) and [tert-butoxycarbonyl-(3-{5-[6-(6-methyl-pyridin-2-yl)-1H-pyrrolo[2,3-b]pyridin-4-yl]-pyridin-3-yl}-benzyl)-amino]-acetic acid methyl ester (Intermediate 192) by replacing 4-chloro-6-(6-methyl-pyridin-2-yl)-1H-pyrrolo[2,3-b]pyridine (Intermediate 6) with 4-chloro-2-(6-methyl-pyridin-2-yl)-7H-pyrrolo[2,3-d]pyrimidine (Intermediate 2).

Intermediates 195 and 196

[tert-Butoxycarbonyl-(4-{5-[2-(6-methyl-pyridin-2-yl)-7H-pyrrolo[2,3-d]pyrimidin-4-yl]-pyridin-3-yl}-benzyl)-amino]-acetic acid methyl ester (Intermediate 195) and [tert-Butoxycarbonyl-(4-{5-[2-(6-methyl-pyridin-2-yl)-7H-pyrrolo[2,3-d]pyrimidin-4-yl]-pyridin-3-yl}-benzyl)-amino]-acetic acid (Intermediate 196) are prepared is by an analogous method to that for [tert-butoxycarbonyl-(3-{5-[2-(6-methyl-pyridin-2-yl)-7H-pyrrolo[2,3-d]pyrimidin-4-yl]-pyridin-3-yl}-benzyl)-amino]-acetic acid methyl ester (Intermediate 193) and [tert-butoxycarbonyl-(3-{5-[2-(6-methyl-pyridin-2-yl)-7H-pyrrolo[2,3-d]pyrimidin-4-yl]-pyridin-3-yl}-benzyl)-amino]-acetic acid (Intermediate 194) by replacing (tert-butoxycarbonyl-{3-[5-(4,4,5,5-tetramethyl-[1,3,2]dioxaborolan-2-yl)-pyridin-3-yl]-benzyl}-amino)-acetic acid methyl ester (Intermediate 145) with (tert-butoxycarbonyl-{4-[5-(4,4,5,5-tetramethyl-[1,3,2]dioxaborolan-2-yl)-pyridin-3-yl]-benzyl}-amino)-acetic acid methyl ester (Intermediate 149).

Intermediate 197

1-(4-Bromo-phenyl)-1-methyl-ethylamine

A mixture of cerium (III) chloride (3 eq, 33 mmol, 8.0 g) in THF (80 ml) is cooled to −70° C. using a dry ice bath. Then methyl lithium (1.5 M, 3 eq, 33 mmol, 22 ml) is added and the resulting mixture is stirred for 90 min at −70° C., before adding a solution of 4-bromobenzonitrile (Sigma-Aldrich, St. Louis, USA) (1 eq, 10.9 mmol, 2.0 g) in THF (5 ml). The mixture is stirred for additional 30 min at −70° C., then warmed to r.t. Aqueous ammonium hydroxide solution is added and the mixture is filtered over Hyflo Super-Cel®. The filtrate is concentrated in vacuo, acetic acid and water are added, and the aqueous layer is washed with DCM. The aqueous layer is adjusted to pH 10 by adding aqueous ammonium hydroxide solution, then the mixture is extracted with DCM. The organic layer is dried with MgSO$_4$, filtered, and the solvent is removed in vacuo yielding the title product; [M+H]$^+$=214/216.

Intermediates 198 to 200

The following intermediates, namely, 1-(3-bromo-phenyl)-1-methyl-ethylamine (Intermediate 198), 1-(4-bromo-3-methyl-phenyl)-1-methyl-ethylamine (Intermediate 199), 1-(4-bromo-2-methyl-phenyl)-1-methyl-ethylamine (Intermediate 200), are prepared by an analogous method to that for 1-(4-bromo-phenyl)-1-methyl-ethylamine (Intermediate 197) by replacing 4-bromobenzonitrile with the corresponding nitrile, namely, 3-bromobenzonitrile (Sigma-Aldrich, St. Louis, USA), 4-bromo-3-methyl-benzonitrile (Sigma-Aldrich, St. Louis, USA), or 4-bromo-2-methyl-benzonitrile (Sigma-Aldrich, St. Louis, USA), respectively.

Intermediate 201

[1-(4-Bromo-phenyl)-1-methyl-ethyl]-carbamic acid tert-butyl ester

To a solution of 1-(4-bromo-phenyl)-1-methyl-ethylamine (Intermediate 197) (1 eq, 10.8 mmol, 2.34 g) in THF (50 ml) are added TEA (1.5 eq, 16.2 mmol, 2.26 ml) and Boc$_2$O (1.1 eq, 11.9 mmol, 2.6 g). The resulting mixture is stirred for 4 h at r.t. The solvents are evaporated, sat. aqueous NaCl solution is added, and the mixture is extracted with DCM. The combined organic layers are dried with MgSO$_4$, filtered, and the solvents are removed under reduced pressure giving the title compound; [M+H]$^+$=314/316.

Intermediates 202 to 211

The following intermediates, namely, [1-(4-bromo-phenyl)-ethyl]-carbamic acid tert-butyl ester (Intermediate 202), [4-(5-bromo-pyridin-3-yl)-benzyl]-carbamic acid tert-butyl ester (Intermediate 203), [1-(3-bromo-phenyl)-1-methyl-ethyl]-carbamic acid tert-butyl ester (Intermediate 204), [3-(5-bromo-pyridin-3-yl)-benzyl]-carbamic acid tert-butyl ester (Intermediate 205), [(S)-1-(4-bromo-phenyl)-ethyl]-carbamic acid tert-butyl ester (Intermediate 206), [(R)-1-(4-bromo-phenyl)-ethyl]-carbamic acid tert-butyl ester (Intermediate 207), {[3-(5-bromo-pyridin-3-yl)-benzyl]-tert-butoxycarbonyl-amino}-acetic acid methyl ester (Intermediate 208), {[4-(5-bromo-pyridin-3-yl)-benzyl]-tert-butoxycarbonyl-amino}-acetic acid methyl ester (Intermediate 209), [1-(4-bromo-3-methyl-phenyl)-1-methyl-ethyl]-carbamic acid tert-butyl ester (Intermediate 210), [1-(4-bromo-2-methyl-phenyl)-1-methyl-ethyl]-carbamic acid tert-butyl ester (Intermediate 211), are prepared by an analogous method to that for [1-(4-bromo-phenyl)-1-methyl-ethyl]-carbamic acid tert-butyl ester (Intermediate 201) by replacing 1-(4-bromo-phenyl)-1-methyl-ethylamine (Intermediate 197) with the corresponding amine, namely, 1-(4-bromo-phenyl)-ethylamine (Sigma-Aldrich, St. Louis, USA), 4-(5-bromo-pyridin-3-yl)-benzylamine (Intermediate 74), 1-(3-bromo-phenyl)-1-methyl-ethylamine (Intermediate 198), 3-(5-bromo-pyridin-3-yl)-benzylamine (Intermediate 75), (S)-1-(4-bromo-phenyl)-ethylamine (Sigma-Aldrich, St. Louis, USA), (R)-1-(4-bromo-phenyl)-ethylamine (Sigma-Aldrich, St. Louis, USA), [3-(5-bromo-pyridin-3-yl)-benzylamino]-acetic acid methyl ester (Intermediate 67), [4-(5-bromo-pyridin-3-yl)-benzylamino]-acetic acid methyl ester (Intermediate 68), 1-(4-bromo-3-methyl-phenyl)-1-methyl-ethylamine (Intermediate 199), or 1-(4-bromo-2-methyl-phenyl)-1-methyl-ethylamine (Intermediate 200), respectively.

Intermediate 212

(5-Bromo-pyridin-3-yl)-carbamic acid tert-butyl ester

To a solution of 3-amino-5-bromopyridine (Sigma-Aldrich, St. Louis, USA) (1 eq, 5.7 mmol, 1.00 g) in DMF (10 ml) are added Boc$_2$O (1.1 eq, 6.3 mmol, 1.37 g) and TEA (0.25 eq, 1.44 mmol, 0.2 ml). The resulting mixture is stirred for 2 h at 90° C., then poured into water and extracted with EtOAc. The organic layer is washed with water and sat. aqueous NaCl solution, dried over MgSO$_4$, and concentrated under reduced pressure. The crude product is purified by column chromatography (hexane/EtOAc) to give the title compound; [M+H]$^+$=273/275.

Intermediate 213

2-(3-Bromo-phenyl)-pyrrolidine-1-carboxylic acid tert-butyl ester

To a solution of 2-(3-bromophenyl)pyrrolidine hydrochloride (ChemCollect GmbH, Remscheid, Germany) (1 eq, 1.89 mmol, 500 mg) in THF (10 ml) at 0° C. is added LHMDS (1 M in THF, 2.2 eq, 4.1 mmol, 4.1 ml). The cooling bath is removed and the mixture is stirred for 10 min before adding a solution of Boc$_2$O (1 eq, 1.89 mmol, 411 mg) in THF (5 ml). The resulting mixture is stirred for additional 2 h, then aqueous HCl (1 M) is added and the mixture is extracted with EtOAc. The organic layer is dried with MgSO$_4$, filtered, and concentrated in vacuo giving the title compound; [M+H]$^+$=326/328.

Intermediate 214

5-Bromo-1',2',3',6'-tetrahydro-[3,4']bipyridinyl is prepared by an analogous method to that for 3-amino-N-{5-[2-(6-methyl-pyridin-2-yl)-7H-pyrrolo[2,3-d]pyrimidin-4-yl]-pyridin-3-yl}-propionamide (Example 50) (Route G) by replacing (2-{5-[2-(6-methyl-pyridin-2-yl)-7H-pyrrolo[2,3-d]pyrimidin-4-yl]-pyridin-3-ylcarbamoyl}-ethyl)-carbamic acid tert-butyl ester (Intermediate 59) with 5-bromo-3',6'-dihydro-2'H-[3,4']bipyridinyl-1'-carboxylic acid tert-butyl ester (Intermediate 82).

Intermediate 215

1-(5-Bromo-3',6'-dihydro-2'H-[3,4']bipyridinyl-1'-yl)-ethanone

To a solution of 5-bromo-1',2',3',6'-tetrahydro-[3,4']bipyridinyl (Intermediate 214) (1 eq, 0.523 mmol, 125 mg) in DCM (5 ml) at 0° C. is added TEA (1.1 eq, 0.575 mmol, 0.08 ml). Then acetyl chloride (1.1 eq, 0.575 mmol, 0.041 ml) is added and the resulting mixture is stirred for 20 h at r.t. Additional TEA (1.1 eq, 0.575 mmol, 0.08 ml) and acetyl chloride (1.1 eq, 0.575 mmol, 0.041 ml) are added and stirring is continued for another 1.5 h. The mixture is diluted with DCM and washed with 10% aqueous K$_2$CO$_3$ solution. The organic layer is dried over MgSO$_4$, filtered, and the solvent is removed under reduced pressure giving the title compound; [M+H]$^+$=281/283.

Intermediate 216

2-(6-Methyl-pyridin-2-yl)-4-(5-trimethylsilanylethynyl-pyridin-3-yl)-7H-pyrrolo[2,3-d]pyrimidine To a suspension of of 4-(5-bromo-pyridin-3-yl)-2-(6-methyl-pyridin-2-yl)-7H-pyrrolo[2,3-d]pyrimidine (Example 16) (1 eq, 0.451 mmol, 250 mg) in TEA/DMF (1:1, 6 ml) are added copper (I) iodide (0.1 eq, 0.045 mmol, 8.8 mg), PdCl$_2$(PPh$_3$)$_2$ (0.1 eq, 0.045 mmol, 32.3 mg), and trimethylsilylacetylene (Sigma-Aldrich, St. Louis, USA) (1.5 eq, 0.68 mmol, 0.098 ml). The resulting mixture is stirred at 90° C. for 1 h. The solvents are removed in vacuo, then sat. aqueous NaHCO$_3$ solution is added, and the mixture is extracted with EtOAc. The organic layer is washed with sat. aqueous NaCl solution, dried with MgSO$_4$, and concentrated under reduced pressure. The crude product is purified by reversed phase HPLC and recrystallized in EtOAc giving the title compound; [M+H]$^+$=384.

Intermediate 217

1-[3-(5-Bromo-pyridin-3-yl)-prop-2-ynyl]-4-methyl-piperazine is prepared by an analogous method to 4-{5-[3-(4-methyl-piperazin-1-yl)-prop-1-ynyl]-pyridin-3-yl}-2-(6-methyl-pyridin-2-yl)-7H-pyrrolo[2,3-d]pyrimidine (Example 122) (Route J) by replacing 4-(5-bromo-pyridin-3-yl)-2-(6-methyl-pyridin-2-yl)-7H-pyrrolo[2,3-d]pyrimidine with 3,5-dibromopyridine (Sigma-Aldrich, St. Louis, USA).

Intermediate 218

3-(5-Bromo-pyridin-3-yl)-prop-2-yn-1-ol is prepared by an analogous method to 1-[3-(5-bromo-pyridin-3-yl)-prop-2-ynyl]-4-methyl-piperazine (Intermediate 217) by replacing 1-ethyl-4-prop-2-ynyl-piperazine with propargyl alcohol (Sigma-Aldrich, St. Louis, USA).

Intermediate 219

(6-Iodo-pyridin-3-ylmethyl)-dimethyl-amine is prepared by an analogous method to 4-iodo-2-(6-methyl-pyridin-2-yl)-7H-pyrrolo[2,3-d]pyrimidine (Intermediate 3) by replacing 4-chloro-2-(6-methyl-pyridin-2-yl)-7H-pyrrolo[2,3-d]pyrimidine (Intermediate 2) with (6-bromo-pyridin-3-ylmethyl)-dimethyl-amine (Intermediate 65).

Intermediate 220

(5'-Bromo-[2,3']bipyridinyl-5-ylmethyl)-dimethylamine

To a solution of (6-iodo-pyridin-3-ylmethyl)-dimethylamine (Intermediate 219) (1 eq, 3.89 mmol, 1.02 g) in DME/EtOH (1:1, 10 ml) are added 5-bromo-pyridine-3-boronic acid (Intermediate 100) (1.1 eq, 4.28 mmol, 0.864 g), Pd(PPh$_3$)$_4$ (0.05 eq, 0.195 mmol, 0.225 g), and aqueous Na$_2$CO$_3$ solution (4M, 3 eq, 11.7 mmol, 2.92 ml). The resulting mixture is heated using microwave radiation at 130° C. for 20 min. The mixture is filtered through a pad of Celite and concentrated under reduced pressure. 2M aqueous HCl is added, and the mixture is washed with DCM. The aqueous layer is adjusted to pH 11 using aqueous NaOH, and extracted with DCM. The organic layer is dried over MgSO$_4$, and the solvents are removed in vacuo. The crude mixture is purified using reversed phase HPLC to give the title compound; [M+H]$^+$=292/294.

Intermediate 221

5-Bromo-3,4-dihydro-2H-pyrano[2,3-c]pyridine

Step A: 3-(3,5-Dibromo-pyridin-4-yl)-acrylic acid ethyl ester 3,5-Dibromo-pyridine-4-carbaldehyde (Sigma-Aldrich, St. Louis, USA) (1 eq, 15.1 mmol, 4.0 g) is suspended in EtOH (50 ml). Then triethyl phosphonoacetate (Sigma-Aldrich, St. Louis, USA) (1.1 eq, 16.6 mmol, 3.32 ml) and sodium ethoxide (21% in EtOH, 1.1 eq, 16.6 mmol, 6.12 ml) are added. The resulting mixture is stirred for 15 min at r.t., before adding sat. aqueous NaHCO$_3$ solution. The mixture is extracted with DCM, and the organic layer is dried with MgSO$_4$ and concentrated in vacuo. Purification by column chromatography (hexane/EtOAc) yields the title compound; [M+H]$^+$=336.

Step B: 3-(3,5-Dibromo-pyridin-4-yl)-propan-1-ol

To a solution of 3-(3,5-dibromo-pyridin-4-yl)-acrylic acid ethyl ester (1 eq, 17.0 mmol, 5.7 g) in EtOH (100 ml) at −18° C. is added NaBH$_4$ (2 eq, 34.0 mmol, 1.29 g). The cooling bath is removed and the mixture is stirred at r.t. for 1.5 h. Then additional NaBH$_4$ (0.78 eq, 13.2 mmol, 0.5 g) is added and the mixture is heated at 50° C. for 6 h. After cooling to r.t., glacial acetic acid is added, then the mixture is concentrated under reduced pressure. The residue is taken up in EtOAc, and washed with aqueous HCl (1M), sat. aqueous NaHCO$_3$ solution, and sat. aqueous NaCl solution. The organic layer is dried with MgSO$_4$, filtered, and concentrated in vacuo. The crude product is purified using column chromatography (hexane/EtOAc) to give the title compound; [M+H]$^+$=295.

Step C: 5-Bromo-3,4-dihydro-2H-pyrano[2,3-c]pyridine

To a solution of 3-(3,5-dibromo-pyridin-4-yl)-propan-1-ol (1 eq, 4.41 mmol, 1.3 g) in DME (8 ml) is added copper (I) chloride (0.05 eq, 0.22 mmol, 22 mg), 2-aminopyridine (0.05 eq, 0.22 mmol, 21 mg), and NaOMe (5.4M in MeOH, 1.5 eq, 6.61 mmol, 1.22 ml). The resulting mixture is heated using microwave radiation at 70° C. for 20 h. Then sat. aqueous NaHCO$_3$ solution is added, and the mixture is extracted with EtOAc. The organic layer is dried with MgSO$_4$, filtered, and concentrated in vacuo. The crude product is purified using column chromatography (hexane/EtOAc) to give the title compound; [M+H]$^+$=214/216.

Intermediate 222

3-(4-{5-[6-(6-Methyl-pyridin-2-yl)-1H-pyrrolo[2,3-b]pyridin-4-yl]-pyridin-3-yl}-benzylamino)-propionic acid ethyl ester is prepared by an analogous method to that for (4-{5-[6-(6-methyl-pyridin-2-yl)-1H-pyrrolo[2,3-b]pyridin-4-yl]-pyridin-3-yl}-benzylamino)-acetic acid methyl ester (Example 133) (Route E) by replacing amino-acetic acid methyl ester with 3-amino-propionic acid ethyl ester (Rare Chemicals GmbH, Kiel, Germany).

Intermediate 223

Methanesulfonic acid 3-(5-bromo-pyridin-3-yl)-prop-2-ynyl ester 3-(5-Bromo-pyridin-3-yl)-prop-2-yn-1-ol (Intermediate 218) (1 eq, 2.41 mmol, 510 mg) is dissolved in DCM (5 ml), then TEA (1.5 eq, 3.61 mmol, 0.5 ml) and methanesulfonyl chloride (1.5 eq, 3.61 mmol, 0.28 ml) are added. The resulting mixture is stirred for 30 min at r.t. After addition of water the layers are separated, and the organic layer is dried with $MgSO_4$, filtered, and concentrated under reduced pressure giving the title compound.

Intermediate 224

3-Bromo-5-[3-(3,3-difluoro-pyrrolidin-1-yl)-prop-1-ynyl]-pyridine

To a solution of methanesulfonic acid 3-(5-bromo-pyridin-3-yl)-prop-2-ynyl ester (Intermediate 223) (1 eq, 1.95 mmol, 566 mg) in DMF (6 ml) are added $K_2CO_3$ (2.5 eq, 4.88 mmol, 674 mg) and 3,3-difluoro-pyrrolidine hydrochloride (ABCR GmbH & Co. KG, Karlsruhe, Germany) (1.2 eq, 2.34 mmol, 336 mg). The resulting mixture is heated at 80° C. for 2 h. The reaction mixture is cooled to r.t. before adding water and extracting the mixture with EtOAc. The organic layer is dried with $MgSO_4$, filtered, and the solvents are removed in vacuo. Purification by column chromatography yields the title compound; $[M+H]^+=301/303$.

Intermediates 225 and 226

The following intermediates, namely, 4-[3-(5-bromo-pyridin-3-yl)-prop-2-ynyl]-morpholine (Intermediate 225), [3-(5-bromo-pyridin-3-yl)-prop-2-ynyl]-dimethyl-amine (Intermediate 226), are prepared by an analogous method to that for 3-bromo-5-[3-(3,3-difluoro-pyrrolidin-1-yl)-prop-1-ynyl]-pyridine (Intermediate 224) by replacing 3,3-difluoro-pyrrolidine hydrochloride with the corresponding amine, nameyl, morpholine (Sigma-Aldrich, St. Louis, USA), dimethylamine (Sigma-Aldrich, St. Louis, USA).

Intermediate 227

[3-(5-Bromo-pyridin-3-yl)-phenyl]-acetic acid methyl ester

To a solution of [3-(5-bromo-pyridin-3-yl)-phenyl]-acetic acid (Intermediate 94) (1 eq, 4.1 mmol, 1.2 g) in THF (15 ml) is added thionyl chloride (1.5 eq, 6.16 mmol, 0.45 ml), and the resulting mixture is stirred for 30 min at r.t. Then MeOH (3 eq, 12.3 mmol, 0.5 ml) is added and stirring is continued for another 20 h. Addition of 10% aqueous $NaHCO_3$ solution is followed by extraction with EtOAc. The organic layer is dried with $MgSO_4$, filtered, and the solvents are removed in vacuo. Purification or the crude mixture by column chromatography (hexane/EtOAc) gives the title compound; $[M+H]^+=306/308$.

Intermediate 228

[1-(4-Bromo-phenyl)-1-methyl-ethyl]-dimethyl-amine

To a solution of 1-(4-bromo-phenyl)-1-methyl-ethylamine (Intermediate 197) (1 eq, 6.07 mmol, 1.3 g) in DMF (25 ml) are added paraformaldehyde (25 eq, 152 mmol, 4.56 g) and formic acid (15 eq, 91 mmol, 4.19 g). The resulting mixture is heated at 80° C. for 2 h. After cooling to r.t. the mixture is filtered, and the solvent is removed under reduced pressure. Addition of water is followed by extraction with EtOAc. The organic layer is dried with $MgSO_4$, filtered, and the solvents are removed in vacuo to give the title compound; $[M+H]^+=242/244$.

Intermediate 229

1-[4-(5-Bromo-pyridin-3-yl)-phenyl]-1-methyl-ethylamine is prepared by an analogous method to that for 3-amino-N-{5-[2-(6-methyl-pyridin-2-yl)-7H-pyrrolo[2,3-d]pyrimidin-4-yl]-pyridin-3-yl}-propionamide (Example 50) (Route G) by replacing (2-{5-[2-(6-methyl-pyridin-2-yl)-7H-pyrrolo[2,3-d]pyrimidin-4-yl]-pyridin-3-ylcarbamoyl}-ethyl)-carbamic acid tert-butyl ester (Intermediate 59) with {1-[4-(5-bromo-pyridin-3-yl)-phenyl]-1-methyl-ethyl}-carbamic acid tert-butyl ester (Intermediate 87).

Intermediate 230

4-{1-[4-(5-Bromo-pyridin-3-yl)-phenyl]-1-methylethyl}-morpholine

A mixture of 1-[4-(5-bromo-pyridin-3-yl)-phenyl]-1-methyl-ethylamine (Intermediate 229) (1 eq, 1.72 mmol, 500 mg), TEA (3.5 eq, 6.01 mmol, 608 mg), and 2-chloroethyl ether (Sigma-Aldrich, St. Louis, USA) (4 eq, 6.87 mmol, 0.8 ml) in DMF (10 ml) is heated using microwave radiation at 150° C. for 1 h. The mixture is concentrated under reduced pressure, then sat. aqueous $NaHCO_3$ solution is added, followed by extraction with EtOAc. The organic layer is dried with $MgSO_4$, filtered, and the solvents are removed in vacuo. Purification or the crude mixture by column chromatography (hexane/EtOAc) gives the title compound; $[M+H]^+=361/363$.

Intermediate 231

2-{1-[4-(5-Bromo-pyridin-3-yl)-phenyl]-1-methylethylamino}-ethanol

To a solution of 1-[4-(5-bromo-pyridin-3-yl)-phenyl]-1-methyl-ethylamine (Intermediate 229) (1 eq, 1.72 mmol, 500 mg) in DMF (10 ml) is added NaH (1.2 eq, 2.06 mmol, 82 mg) and the resulting mixture is stirred for 30 min at r.t. Then 2-bromoethanol (Sigma-Aldrich, St. Louis, USA) (2 eq, 3.43 mmol, 0.24 ml) is added, and the mixture is heated at 100° C. for 4 h. 2 M aqueous NaOH is added, and the mixture is extracted with DCM.

The organic layer is dried with $MgSO_4$, filtered, and the solvents are removed in vacuo, giving the title compound; $[M+H]^+=335/337$.

What is claimed is:
1. A compound of formula I

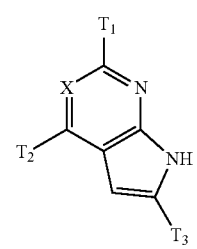

(I)

in free or salt form, wherein
$T_1$ is a 4- to 14-membered heterocyclic group bound to the rest of the molecule via a ring carbon atom or $C_4$-$C_{15}$-cycloalkenyl each of which is unsubstituted or independently substituted at one, two or three positions by $R_1$, $C_1$-$C_8$-alkoxy, $C_3$-$C_{10}$-cycloalkyl, $C_1$-$C_8$-alkylthio, halo, halo-$C_1$-$C_8$-alkyl, amino, $C_1$-$C_8$-alkylamino, di($C_1$-$C_8$-alkyl)amino, cyano, oxo, hydroxy, carboxy or nitro;

$T_2$ is a 4- to 14-membered heterocyclic group bound to the rest of the molecule via a ring carbon atom and unsubstituted or independently substituted at one, two or three positions by $R_1$, $R_2$, $R_3$, $C_1$-$C_8$-alkoxy, $C_1$-$C_8$-alkoxycarbonyl, $C_1$-$C_8$-alkylthio, halo, halo-$C_1$-$C_8$-alkyl, amino, $C_1$-$C_8$-alkylamino, di($C_1$-$C_8$-alkyl)amino, —C(=O)NR$_4$R$_5$, —NH(C=O)R$_1$, —NH(C=O)—$C_1$-$C_8$-alkyl-NR$_4$R$_5$, cyano, oxo, hydroxy, carboxy or nitro;

$R_1$ is $C_1$-$C_8$-alkyl, $C_2$-$C_8$-alkenyl or $C_2$-$C_8$-alkynyl unsubstituted or independently substituted at one, two or three positions by carboxy-$C_1$-$C_8$-alkyl, $C_1$-$C_8$-alkoxy-carbonyl-$C_1$-$C_8$-alkyl, hydroxy, oxo, cyano, amino, $C_1$-$C_8$-alkylamino, di($C_1$-$C_8$-alkyl)amino, $C_1$-$C_8$-alkanoylamino, carboxyl-$C_1$-$C_8$-alkylamino, $C_1$-$C_8$-alkoxy-carbonyl-$C_1$-$C_8$-alkylamino, N-(carboxyl-$C_1$-$C_8$-alkyl)-N—($C_1$-$C_8$-alkyl)-amino, N—($C_1$-$C_8$-alkoxy-carbonyl-$C_1$-$C_8$-alkyl)-N—($C_1$-$C_8$-alkyl)-amino, amido-$C_1$-$C_8$-alkylamino, N-mono- or N,N-di-($C_1$-$C_8$-alkyl)-amido-$C_1$-$C_8$-alkylamino, tri-($C_1$-$C_8$-alkyl)-silanyl, halo, $C_1$-$C_8$-alkoxy, heterocycle, —C(=O)-heterocycle, —C(=O)NR$_4$R$_5$, —NH(C=O)—$C_1$-$C_8$-alkyl or —SO$_2$NR$_4$R$_5$, wherein heterocycle is a 4- to 14-membered heterocyclic group bound via a carbon atom or, if it comprises a ring nitrogen not bound to a double bond, via a ring nitrogen or a ring carbon atom, and is unsubstituted or independently substituted at one, two or three positions by oxo, amino, halo, $C_1$-$C_8$-alkyl, C(=O)—$C_1$-$C_8$-alkyl, $C_1$-$C_8$-alkylamino, di($C_1$-$C_8$-alkyl)amino, cyano, hydroxy, carboxy, nitro, $C_1$-$C_8$-alkoxy, $C_1$-$C_8$-alkylthio, halo-$C_1$-$C_8$-alkyl, —C(=O)—NH$_2$ or —SO$_2$—NH$_2$;

$R_2$ is $C_6$-$C_{15}$-aryl, $C_4$-$C_{15}$-cycloalkyl or $C_4$-$C_{15}$-cycloalkenyl, each of which is unsubstituted or independently substituted at one, two or three positions by oxo, halo, hydroxy, $R_1$, $R_3$, $C_1$-$C_8$-alkylthio, amino, $C_1$-$C_8$-alkylamino, di($C_1$-$C_8$-alkyl)amino, cyano, carboxy, nitro, $C_6$-$C_{15}$-aryl-oxy, halo-$C_1$-$C_8$-alkyl, —NR$_4$R$_5$, R$_4$R$_5$N—$C_1$-$C_8$-alkyl, R$_4$R$_5$N—$C_1$-$C_8$-alkoxy, R$_3$—$C_1$-$C_8$-alkyl, —O—R$_1$, —O—R$_3$, —C(=O)—R$_3$, —C(=O)—NH$_2$, —C(=O)NR$_4$R$_5$, —C(=O)—O—R$_1$, —O—C(=O)—R$_1$, —SO$_2$—NH$_2$, —SO$_2$—R$_1$, $C_1$-$C_8$-alkyl-SO$_2$—NH—, —C(=O)—NH—R$_3$, aryl-$C_6$-$C_{15}$—SO$_2$—, —SO$_2$—R$_3$ or —SO$_2$NR$_4$R$_5$;

$R_3$ is a 4- to 14-membered heterocyclic group bound via a carbon atom or, if it comprises a ring nitrogen not bound to a double bond, via a ring nitrogen or a ring carbon atom, and is unsubstituted or independently substituted at one, two or three positions by oxo, amino, halo, $C_1$-$C_8$-alkylamino, di($C_1$-$C_8$-alkyl)amino, cyano, hydroxy, carboxy, nitro, $R_1$, $C_1$-$C_8$-alkoxy, $C_1$-$C_8$-alkylthio, halo-$C_1$-$C_8$-alkyl, —C(=O)—R$_1$, —C(=O)—NH$_2$ or —SO$_2$—NH$_2$;

$R_4$ and $R_5$ are independently hydrogen, $R_1$, $C_1$-$C_8$-alkylamino, di($C_1$-$C_8$-alkyl)amino, $C_6$-$C_{15}$-aryl, $C_6$-$C_{15}$-aryl-$C_1$-$C_8$-alkyl, $C_1$-$C_8$-alkylamino-$C_1$-$C_8$-alkyl, di($C_1$-$C_8$-alkyl)amino-$C_1$-$C_8$-alkyl, —C(=O)—R$_1$, R$_3$ or —$C_1$-$C_8$-alkyl-R$_3$;

$T_3$ is H, $R_1$, OH or NH$_2$; and

X is N.

2. A compound according to claim 1, in free or salt form, wherein $T_1$ is a 4- to 14-membered heterocyclic group bound to the rest of the molecule via a ring carbon atom or $C_4$-$C_{15}$-cycloalkenyl each of which is unsubstituted or independently substituted at one, two or three positions by $R_1$, $C_1$-$C_8$-alkoxy, $C_3$-$C_{10}$-cycloalkyl, $C_1$-$C_8$-alkylthio, halo, halo-$C_1$-$C_8$-alkyl, amino, $C_1$-$C_8$-alkylamino, di($C_1$-$C_8$-alkyl)amino, cyano, oxo, hydroxy, carboxy or nitro;

$T_2$ is a 4- to 14-membered heterocyclic group bound to the rest of the molecule via a ring carbon atom and unsubstituted or independently substituted at one, two or three positions by $R_1$, $R_2$, $R_3$, $C_1$-$C_8$-alkoxy, $C_1$-$C_8$-alkoxycarbonyl, $C_1$-$C_8$-alkylthio, halo, halo-$C_1$-$C_8$-alkyl, amino, $C_1$-$C_8$-alkylamino, di($C_1$-$C_8$-alkyl)amino, —C(=O)NR$_4$R$_5$, —NH(C=O)R$_1$, —NH(C=O)—$C_1$-$C_8$-alkyl-NR$_4$R$_5$, cyano, oxo, hydroxy, carboxy or nitro;

$R_1$ is $C_1$-$C_8$-alkyl, $C_2$-$C_8$-alkenyl or $C_2$-$C_8$-alkynyl unsubstituted or independently substituted at one, two or three positions by hydroxy, cyano, amino, $C_1$-$C_8$-alkylamino, di($C_1$-$C_8$-alkyl)amino, $C_1$-$C_8$-alkanoylamino, halo, $C_1$-$C_8$-alkoxy, $R_3$, —C(=O)—R$_3$, —C(=O)NR$_4$R$_5$, —NH(C=O)—$C_1$-$C_8$-alkyl or —SO$_2$NR$_4$R$_5$;

$R_2$ is $C_6$-$C_{15}$-aryl, $C_4$-$C_{15}$-cycloalkyl or $C_4$-$C_{15}$-cycloalkenyl, each of which is unsubstituted or independently substituted at one, two or three positions by oxo, halo, hydroxy, $R_1$, $R_3$, $C_1$-$C_8$-alkylthio, amino, $C_1$-$C_8$-alkylamino, di($C_1$-$C_8$-alkyl)amino, cyano, carboxy, nitro, $C_6$-$C_{15}$-aryl-oxy, halo-$C_1$-$C_8$-alkyl, —NR$_4$R$_5$, R$_4$R$_5$N—$C_1$-$C_8$-alkyl, R$_4$R$_5$N—$C_1$-$C_8$-alkoxy, R$_3$—$C_1$-$C_8$-alkyl, —O—R$_1$, —O—R$_3$, —C(=O)—R$_3$, —C(=O)—NH$_2$, —C(=O)NR$_4$R$_5$, —C(=O)—O—R$_1$, —O—C(=O)—R$_1$, —SO$_2$—NH$_2$, —SO$_2$—R$_1$, $C_1$-$C_8$-alkyl-SO$_2$—NH—, —C(=O)—NH—R$_3$, aryl-$C_6$-$C_{15}$—SO$_2$—, —SO$_2$—R$_3$ or —SO$_2$NR$_4$R$_5$;

$R_3$ is a 4- to 14-membered heterocyclic group bound via a carbon atom or, if it comprises a ring nitrogen not bound to a double bond, via a ring nitrogen or a ring carbon atom, and is unsubstituted or independently substituted at one, two or three positions by oxo, amino, halo, $C_1$-$C_8$-alkylamino, di($C_1$-$C_8$-alkyl)amino, cyano, hydroxy, carboxy, nitro, —R$_1$, $C_1$-$C_8$-alkoxy, $C_1$-$C_8$-alkylthio, halo-$C_1$-$C_8$-alkyl, —C(=O)—R$_1$, —C(=O)—NH$_2$ or —SO$_2$—NH$_2$;

$R_4$ and $R_5$ are independently hydrogen, —R$_1$, $C_1$-$C_8$-alkylamino, di($C_1$-$C_8$-alkyl)amino, $C_6$-$C_{15}$-aryl, $C_6$-$C_{15}$-aryl-$C_1$-$C_8$-alkyl, $C_1$-$C_8$-alkylamino-$C_1$-$C_8$-alkyl, di($C_1$-$C_8$-alkyl)amino-$C_1$-$C_8$-alkyl, —C(=O)—R$_1$, R$_3$ or —$C_1$-$C_8$-alkyl-R$_3$;

$T_3$ is H, $R_1$, OH or NH$_2$; and

X is N.

3. A compound according to claim 1 of the formula I in free or salt form, wherein $T_1$ is pyridin-2-yl or 6-methyl-pyridin-2-yl, $T_2$ is pyridin-3-yl, 4-methyl-pyridin-3-yl, 5-methylpyridin-3-yl, 5-ethynyl-pyridin-3-yl, 5-[3-(N,N-dimethylamino)-prop-1-ynyl]-pyridin-3-yl, 5-[3-(3,3-difluoro-pyrrolidin-1-yl)-prop-1-ynyl]-pyridin-3-yl, 5-[3-(4-methyl-piperazin-1-yl)-prop-1-ynyl]-pyridin-3-yl, 5-[3-(morpholino)-prop-1-ynyl]-pyridin-3-yl, 5-hydroxy-pyridin-3-yl, 4-hydroxy-pyridin-3-yl, 5-amino-pyridin-3-yl, 5-methylsulfanyl-pyridin-3-yl, 5-cyano-pyridin-3-yl, 5-hydroxymethyl-pyridin-3-yl, 4-hydroxymethyl-pyridin-3-yl, 5-(cyclopenten-1-enyl)-pyridin-3-yl, 5-(cyclohex-1-enyl)-pyridin-3-yl,
5-(2-methyl-phenyl)-pyridin-3-yl,
5-(3-hydroxyphenyl)-pyridin-3-yl,
5-(4-methoxy-phenyl)-pyridin-3-yl, 5-(3-methoxy-phenyl)-pyridin-3-yl, 5-(2-methoxy-phenyl)-pyridin-3-yl,
5-(4-hydroxymethyl-phenyl)-pyridin-3-yl, 5-(3-hydroxymethyl-phenyl)-pyridin-3-yl,
5-(4-aminomethyl-phenyl)-pyridin-3-yl, 5-(3-aminomethyl-phenyl)-pyridin-3-yl,
5-[4-(1-aminoethyl)-phenyl]-pyridin-3-yl,
5-[4-(1-amino-1,1-di(methyl)-methyl)-phenyl]-pyridin-3-yl, 5-[3-(1-amino-1,1-di(methyl)-methyl)-phenyl]-pyridin-3-yl,
5-[4-(1-{N,N-dimethylamino}-1,1-di-{methyl}-methyl)-phenyl]-pyridin-3-yl, 5-[3-{N,N-dimethylamino}-1,1-di{methyl}-methyl)-phenyl]-pyridin-3-yl,
5-[4-(1-{N,N-dimethylamino}-1,1-di-{methyl}-methyl)-2-methyl-phenyl]-pyridin-3-yl, 5-[3-{N,N-dimethylamino}-1,1-di{methyl}-methyl)-2-methyl-phenyl]-pyridin-3-yl, 5-[4-(1-{N,N-dimethylamino}-1,1-di{methyl}-methyl)-3-methyl-phenyl]-pyridin-3-yl, 5-[3-{N,N-dimethylamino}-1,1-di{methyl}-methyl)-3-methyl-phenyl]-pyridin-3-yl,
5-[4-(1-{2-hydroxyethylamino}-1,1-di(methyl)-methyl)-phenyl]-pyridin-3-yl, 5-[3-(1-{2-hydroxyethylamino}-1,1-di(methyl)-methyl)-phenyl]-pyridin-3-yl,
5-[4-(1-{N-(2-hydroxyethyl)-N-(methyl)-amino}-1,1-di(methyl)-methyl)-phenyl]-pyridin-3-yl, 5-[3-(1-{N-(2-hydroxyethyl)-N-(methyl)-amino}-1,1-di(methyl)-methyl)-phenyl]-pyridin-3-yl,
5-[4-(1-morpholino-1,1-di(methyl)-methyl)-phenyl]-pyridin-3-yl, 5-[3-(1-morpholino-1,1-di(methyl)-methyl)-phenyl]-pyridin-3-yl,
5-[4-(N-methylamino-methyl)-phenyl]-pyridin-3-yl, 5-[3-(N-methylamino-methyl)-phenyl]-pyridin-3-yl,
5-[4-(N,N-dimethylaminomethyl)-phenyl]-pyridin-3-yl, 5-[3-(N,N-dimethylaminomethyl)-phenyl]-pyridin-3-yl,
5-[3-{N-(2-hydroxyethyl)aminomethyl}-phenyl]-pyridin-3-yl, 5-[4-{N-(2-hydroxyethyl)-aminomethyl}-phenyl]-pyridin-3-yl, 5-[3-{N-(3-hydroxypropyl)-aminomethyl}-phenyl]-pyridin-3-yl, 5-[4-{N-(3-hydroxypropyl)-aminomethyl}-phenyl]-pyridin-3-yl,
5-[3-{N-(2-hydroxyethyl)-N-methyl-aminomethyl}-phenyl]-pyridin-3-yl, 5-[4-{N-(2-hydroxyethyl)-N-methyl-aminomethyl}-phenyl]-pyridin-3-yl, 5-[3-{N-(3-hydroxypropyl)-aminomethyl}-N-methyl-phenyl]-pyridin-3-yl, 5-[4-{N-(3-hydroxypropyl)-N-methyl-aminomethyl}-phenyl]-pyridin-3-yl,
5-[3-{N-(methoxycarbonyl-methyl)-aminomethyl}-phenyl]-pyridin-3-yl, 5-[4-{N-(methoxycarbonyl-methyl)-aminomethyl}-phenyl]-pyridin-3-yl,
5-[3-{N-(methoxycarbonyl-methyl)-N-methyl-aminomethyl}-phenyl]-pyridin-3-yl, 5-[4-{N-(methoxycarbonyl-methyl)-N-methyl-aminomethyl}-phenyl]-pyridin-3-yl,
5-(4-morpholinomethyl-phenyl)-pyridin-3-yl, 5-(3-morpholinomethyl-phenyl)-pyridin-3-yl,
5-(4-morpholino-phenyl)-pyridin-3-yl, 5-(3-morpholino-phenyl)-pyridin-3-yl,
5-(4-fluoro-phenyl)-pyridin-3-yl, 5-(2-fluoro-phenyl)-pyridin-3-yl, 5-(2-chloro-phenyl)-pyridin-3-yl,
5-[4-(3-hydroxyazetidin-1-ylmethyl)-phenyl]-pyridin-3-yl,
5-[4-(4-methyl-piperazin-1-ylmethyl)-phenyl]-pyridin-3-yl, 5-[3-(4-methyl-piperazin-1-ylmethyl)-phenyl]-pyridin-3-yl, 5-[4-(4-isopropyl-piperazin-1-ylmethyl)-phenyl]-pyridin-3-yl, 5-[3-(4-isopropyl-piperazin-1-ylmethyl)-phenyl]-pyridin-3-yl,
5-[4-(4-methyl-piperazin-1-yl)-phenyl]-pyridin-3-yl,
5-[4-(piperazin-2-yl)-phenyl]-pyridin-3-yl, 5-[3-(piperazin-2-yl)-phenyl]-pyridin-3-yl,
5-(3-pyrrolidin-1-yl-phenyl)-pyridin-3-yl,
5-(3-pyrrolidin-2-yl-phenyl)-pyridin-3-yl,
5-(4-piperidin-1-yl-phenyl)-pyridin-3-yl,
5-[4-(4-methyl-piperazin-1-yl)-phenyl]-pyridin-3-yl,
5-[4-(4-isopropyl-piperazin-1-yl)-phenyl]-pyridin-3-yl,
5-[4-(piperazin-1-yl-C(=O))-phenyl]-pyridin-3-yl, 5-[3-(piperazin-1-yl-C(=O))-phenyl]-pyridin-3-yl,
5-[4-(4-methyl-piperazin-1-yl-C(=O))-phenyl]-pyridin-3-yl, 5-[3-(4-methyl-piperazin-1-yl-C(=O))-phenyl]-pyridin-3-yl,
5-[4-{3-(dimethylamino)-pyrrolidin-1-ylmethyl}-phenyl]-pyridin-3-yl,
5-[4-{3,3-(difluoro)-pyrrolidin-1-ylmethyl}-phenyl]-pyridin-3-yl,
5-methoxy-pyridin-3-yl, 5-ethoxy-pyridin-3-yl, 5-isopropoxy-pyridin-3-yl,
5-bromo-pyridin-3-yl,
5-(propionylamino)-pyridin-3-yl,
5-[(3-hydroxy-propionyl)amino]-pyridin-3-yl,
5-[(4-amino-butyryl)-amino]-pyridin-3-yl, 5-[(3-aminopropionyl)-amino]-pyridin-3-yl,
5-[(4-dimethylamino-butyryl)-amino]-pyridin-3-yl, 5-[(3-dimethylamino-propionyl)-amino]-pyridin-3-yl,
5-[(4-acetylamino-butyryl)-amino]-pyridin-3-yl, 5-[(3-acetylamino-propionyl)-amino]-pyridin-3-yl,
5-(N-ethyl-carbamoyl)-pyridin-3-yl,
5-[N-(3-hydroxy-propyl)-carbamoyl]-pyridin-3-yl,
5-{N-[3-(N',N'-dimethylamino)-propyl]-carbamoyl}-pyridin-3-yl, 5-{N-[2-(N',N'-dimethylamino)-ethyl]-carbamoyl}-pyridin-3-yl,
5-{N-[3-(4-methyl-piperazin-1-yl)-propyl]-carbamoyl}-pyridin-3-yl,
5-[5-(N-methylamino-methyl)-pyridin-3-yl]-pyridin-3-yl, 5-[4-(N-methylamino-methyl)-pyridin-3-yl]-pyridin-3-yl,
5-[5-(N,N-dimethylaminomethyl)-pyridin-3-yl]-pyridin-3-yl, 5-[4-(N,N-dimethylaminomethyl)-pyridin-3-yl]-pyridin-3-yl
5-(1-Methyl-1H-pyrazol-4-yl)-pyridin-3-yl,
5-(piperidin-1-yl)-pyridin-3-yl,
5-morpholino-pyridin-3-yl,
5-(4-hydroxy-piperidin-1-yl)-pyridin-3-yl,
5-(4-methylpiperazin-1-yl)-pyridin-3-yl,
[3,4']bipyridin-5-yl, [3,3']bipyridin-5-yl,
5'-dimethylaminomethyl-[5,2']bipyridin-3-yl,
1',2',3',6'-tetrahydro-[5,4']bipyridin-3-yl,
4'-methyl-3',6'-dihydro-2'H-[5,4']bipyridin-3-yl,
4'-acetyl-3',6'-dihydro-2'H-[5,4']bipyridin-3-yl,
5-(1H-tetrazol-5-yl)-pyridin-3-yl,
5-[1,3,4]oxadiazol-2-yl-pyridin-3-yl,
5-(1,2,3,4-tetrahydro-isoquinolin-6-yl)-pyridin-3-yl, 5-(1,2,3,4-tetrahydro-isoquinolin-7-yl)-pyridin-3-yl,
3,4-dihydro-2H-pyrano[2,3-c]pyridine-5-yl,
quinolin-3-yl or isoquinolin-4-yl,
$T_3$ is hydrogen and
X is N.

4. A compound of the formula I according to claim 2 in free or salt form, wherein
$T_1$ is pyridin-2-yl or 6-methyl-pyridin-2-yl,
$T_2$ is pyridin-3-yl, 4-methyl-pyridin-3-yl, 5-(cyclohex-1-enyl)-pyridin-3-yl,
5-(2-methyl-phenyl)-pyridin-3-yl,
5-(3-hydroxyphenyl)-pyridin-3-yl,
5-(4-methoxy-phenyl)-pyridin-3-yl, 5-(3-methoxy-phenyl)-pyridin-3-yl, 5-(2-methoxy-phenyl)-pyridine-3-yl,
5-(4-hydroxymethyl-phenyl)-pyridin-3-yl, 5-(3-hydroxymethyl-phenyl)-pyridin-3-yl,
5-(4-aminomethyl-phenyl)-pyridin-3-yl, 5-(3-aminomethyl-phenyl)-pyridin-3-yl,
5-[4-(N-methylamino-methyl)-phenyl]-pyridin-3-yl, 5-[3-(N-methylamino-methyl)-phenyl]-pyridin-3-yl,
5-[4-(N,N-dimethylaminomethyl)-phenyl]-pyridin-3-yl, 5-[3-(N,N-dimethylaminomethyl)-phenyl]-pyridin-3-yl
5-(4-morpholino-phenyl)-pyridin-3-yl, 5-(3-morpholino-phenyl)-pyridin-3-yl,
5-(4-fluoro-phenyl)-pyridin-3-yl, 5-(2-fluoro-phenyl)-pyridin-3-yl, 5-(2-chloro-phenyl)-pyridin-3-yl,
5-[4-(4-methyl-piperazin-1-ylmethyl)-phenyl]-pyridin-3-yl, 5-[3-(4-methyl-piperazin-1-ylmethyl)-phenyl]-pyridin-3-yl, 5-[4-(4-isopropyl-piperazin-1-ylmethyl)-phenyl]-pyridin-3-yl, 5-[3-(4-isopropyl-piperazin-1-ylmethyl)-phenyl]-pyridin-3-yl,
5-[4-(4-methyl-piperazin-1-yl)-phenyl]-pyridin-3-yl, 5-(3-pyrrolidin-1-yl-phenyl)-pyridin-3-yl, 5-(4-piperidin-1-yl-phenyl)-pyridin-3-yl,
5-[4-(4-methyl-piperazin-1-yl)-phenyl]-pyridin-3-yl, 5-[4-(4-isopropyl-piperazin-1-yl)-phenyl]-pyridin-3-yl,
5-[4-(piperazin-1-yl-C(=O))-phenyl]-pyridin-3-yl, 5-[3-(piperazin-1-yl-C(=O))-phenyl]-pyridin-3-yl,
5-[4-(4-methyl-piperazin-1-yl-C(=O))-phenyl]-pyridin-3-yl, 5-[3-(4-methyl-piperazin-1-yl-C(=O))-phenyl]-pyridin-3-yl,
5-methoxy-pyridin-3-yl, 5-ethoxy-pyridin-3-yl, 5-isopropoxy-pyridin-3-yl,
5-bromo-pyridin-3-yl,
5-(propionylamino)-pyridin-3-yl,
5-[(3-hydroxy-propionyl)amino]-pyridin-3-yl,
5-[(4-amino-butyryl)-amino]-pyridin-3-yl, 5-[(3-amino-propionyl)-amino]-pyridin-3-yl,
5-[(4-dimethylamino-butyryl)-amino]-pyridin-3-yl, 5-[(3-dimethylamino-propionyl)-amino]-pyridin-3-yl,
5-[(4-acetylamino-butyryl)-amino]-pyridin-3-yl, 5-[(3-acetylamino-propionyl)-amino]-pyridin-3-yl,
5-(N-ethyl-carbamoyl)-pyridin-3-yl,
5-[N-(3-hydroxy-propyl)-carbamoyl]-pyridin-3-yl,
5-{N-[3-(N',N'-dimethylamino)-propyl]-carbamoyl}-pyridin-3-yl, 5-{N-[2-(N',N'-dimethylamino)-ethyl]-carbamoyl}-pyridin-3-yl,
5-{N-[3-(4-methyl-piperazin-1-yl)-propyl]-carbamoyl}-pyridin-3-yl,
5-(piperidin-1-yl)-pyridin-3-yl,
5-morpholino-pyridin-3-yl,
5-(4-hydroxy-piperidin-1-yl)-pyridin-3-yl,
5-(4-methylpiperazin-1-yl)-pyridin-3-yl,
[3,4']bipyridin-5-yl, [3,3']bipyridin-5-yl, or
quinolin-3-yl, isoquinolin-4-yl,
$T_3$ is hydrogen and
X is N.

5. A compound of the formula I according to claim 1, selected from the group of compounds with the names:

4-pyridin-3-yl-2-pyridin-2-yl-7H-pyrrolo[2,3-d]pyrimidine;
2-(6-methyl-pyridin-2-yl)-4-pyridin-3-yl-7H-pyrrolo[2,3-d]pyrimidine;
4-(5-methoxy-pyridin-3-yl)-2-(6-methyl-pyridin-2-yl)-7H-pyrrolo[2,3-d]pyrimidine;
2-(6-methyl-pyridin-2-yl)-4-(5-phenyl-pyridin-3-yl)-7H-pyrrolo[2,3-d]pyrimidine;
4-[5-(4-methoxy-phenyl)-pyridin-3-yl]-2-(6-methyl-pyridin-2-yl)-7H-pyrrolo[2,3-d]pyrimidine;
4-[5-(3-methoxy-phenyl)-pyridin-3-yl]-2-(6-methyl-pyridin-2-yl)-7H-pyrrolo[2,3-d]pyrimidine;
4-[5-(4-fluoro-phenyl)-pyridin-3-yl]-2-(6-methyl-pyridin-2-yl)-7H-pyrrolo[2,3-d]pyrimidine;
4-[5-(2-methoxy-phenyl)-pyridin-3-yl]-2-(6-methyl-pyridin-2-yl)-7H-pyrrolo[2,3-d]pyrimidine;
(4-methyl-piperazin-1-yl)-(4-{5-[2-(6-methyl-pyridin-2-yl)-7H-pyrrolo[2,3-d]pyrimidin-4-yl]-pyridin-3-yl}-phenyl)-methanone;
4-{5-[3-(4-methyl-piperazin-1-ylmethyl)-phenyl]-pyridin-3-yl}-2-(6-methyl-pyridin-2-yl)-7H-pyrrolo[2,3-d]pyrimidine;
N-ethyl-5-[2-(6-methyl-pyridin-2-yl)-7H-pyrrolo[2,3-d]pyrimidin-4-yl]-nicotinamide;
N-(2-dimethylamino-ethyl)-5-[2-(6-methyl-pyridin-2-yl)-7H-pyrrolo[2,3-d]pyrimidin-4-yl]-nicotinamide;
N-(3-dimethylamino-propyl)-5-[2-(6-methyl-pyridin-2-yl)-7H-pyrrolo[2,3-d]pyrimidin-4-yl]-nicotinamide;
4-{5-[4-(4-methyl-piperazin-1-yl)-phenyl]-pyridin-3-yl}-2-(6-methyl-pyridin-2-yl)-7H-pyrrolo[2,3-d]pyrimidine;
4-{5-[4-(4-isopropyl-piperazin-1-yl)-phenyl]-pyridin-3-yl}-2-(6-methyl-pyridin-2-yl)-7H-pyrrolo[2,3-d]pyrimidine;
4-(5-bromo-pyridin-3-yl)-2-(6-methyl-pyridin-2-yl)-7H-pyrrolo[2,3-d]pyrimidine;
2-(6-methyl-pyridin-2-yl)-4-[5-(4-piperidin-1-yl-phenyl)-pyridin-3-yl]-7H-pyrrolo[2,3-d]pyrimidine;
2-(6-methyl-pyridin-2-yl)-4-[5-(3-pyrrolidin-1-yl-phenyl)-pyridin-3-yl]-7H-pyrrolo[2,3-d]pyrimidine;
(4-methyl-piperazin-1-yl)-(3-{5-[2-(6-methyl-pyridin-2-yl)-7H-pyrrolo[2,3-d]pyrimidin-4-yl]-pyridin-3-yl}-phenyl)-methanone;
4-{5-[4-(4-methyl-piperazin-1-ylmethyl)-phenyl]-pyridin-3-yl}-2-(6-methyl-pyridin-2-yl)-7H-pyrrolo[2,3-d]pyrimidine;
5-[2-(6-methyl-pyridin-2-yl)-7H-pyrrolo[2,3-d]pyrimidin-4-yl]-[3,4']bipyridinyl;
5-[2-(6-methyl-pyridin-2-yl)-7H-pyrrolo[2,3-d]pyrimidin-4-yl]-[3,3']bipyridinyl;
3-{5-[2-(6-methyl-pyridin-2-yl)-7H-pyrrolo[2,3-d]pyrimidin-4-yl]-pyridin-3-yl}-phenol;
4-[5-(2-fluoro-phenyl)-pyridin-3-yl]-2-(6-methyl-pyridin-2-yl)-7H-pyrrolo[2,3-d]pyrimidine;
N-[3-(4-methyl-piperazin-1-yl)-propyl]-5-[2-(6-methyl-pyridin-2-yl)-7H-pyrrolo[2,3-d]pyrimidin-4-yl]-nicotinamide;
N-(3-hydroxy-propyl)-5-[2-(6-methyl-pyridin-2-yl)-7H-pyrrolo[2,3-d]pyrimidin-4-yl]-nicotinamide;
N-{5-[2-(6-methyl-pyridin-2-yl)-7H-pyrrolo[2,3-d]pyrimidin-4-yl]-pyridin-3-yl}-propionamide;
3-[2-(6-methyl-pyridin-2-yl)-7H-pyrrolo[2,3-d]pyrimidin-4-yl]-quinoline;
4-[2-(6-methyl-pyridin-2-yl)-7H-pyrrolo[2,3-d]pyrimidin-4-yl]-isoquinoline;
4-dimethylamino-N-{5-[2-(6-methyl-pyridin-2-yl)-7H-pyrrolo[2,3-d]pyrimidin-4-yl]-pyridin-3-yl}-butyramide;
3-dimethylamino-N-{5-[2-(6-methyl-pyridin-2-yl)-7H-pyrrolo[2,3-d]pyrimidin-4-yl]-pyridin-3-yl}-propionamide;

2-(6-methyl-pyridin-2-yl)-4-(5-o-tolyl-pyridin-3-yl)-7H-pyrrolo[2,3-d]pyrimidine;
4-[5-(2-chloro-phenyl)-pyridin-3-yl]-2-(6-methyl-pyridin-2-yl)-7H-pyrrolo[2,3-d]pyrimidine;
4-{5-[3-(4-isopropyl-piperazin-1-ylmethyl)-phenyl]-pyridin-3-yl}-2-(6-methyl-pyridin-2-yl)-7H-pyrrolo[2,3-d]pyrimidine;
4-{5-[4-(4-isopropyl-piperazin-1-ylmethyl)-phenyl]-pyridin-3-yl}-2-(6-methyl-pyridin-2-yl)-7H-pyrrolo[2,3-d]pyrimidine;
methyl-(3-{5-[2-(6-methyl-pyridin-2-yl)-7H-pyrrolo[2,3-d]pyrimidin-4-yl]-pyridin-3-yl}-benzyl)-amine;
dimethyl-(3-{5-[2-(6-methyl-pyridin-2-yl)-7H-pyrrolo[2,3-d]pyrimidin-4-yl]-pyridin-3-yl}-benzyl)-amine;
dimethyl-(4-{5-[2-(6-methyl-pyridin-2-yl)-7H-pyrrolo[2,3-d]pyrimidin-4-yl]-pyridin-3-yl}-benzyl)-amine;
methyl-(4-{5-[2-(6-methyl-pyridin-2-yl)-7H-pyrrolo[2,3-d]pyrimidin-4-yl]-pyridin-3-yl}-benzyl)-amine;
(4-{5-[2-(6-methyl-pyridin-2-yl)-7H-pyrrolo[2,3-d]pyrimidin-4-yl]-pyridin-3-yl}-phenyl)-piperazin-1-yl-methanone;
4-[5-(4-methyl-piperazin-1-yl)-pyridin-3-yl]-2-(6-methyl-pyridin-2-yl)-7H-pyrrolo[2,3-d]pyrimidine;
(4-methyl-piperazin-1-yl)-{4-[5-(2-pyridin-2-yl-7H-pyrrolo[2,3-d]pyrimidin-4-yl)-pyridin-3-yl]-phenyl}-methanone;
4-{5-[4-(4-methyl-piperazin-1-ylmethyl)-phenyl]-pyridin-3-yl}-2-pyridin-2-yl-7H-pyrrolo[2,3-d]pyrimidine;
4-(5-bromo-pyridin-3-yl)-2-pyridin-2-yl-7H-pyrrolo[2,3-d]pyrimidine;
4-{5-[3-(4-methyl-piperazin-1-ylmethyl)-phenyl]-pyridin-3-yl}-2-pyridin-2-yl-7H-pyrrolo[2,3-d]pyrimidine;
5'-[2-(6-methyl-pyridin-2-yl)-7H-pyrrolo[2,3-d]pyrimidin-4-yl]-3,4,5,6-tetrahydro-2H-[1,3']bipyridinyl;
5'-[2-(6-methyl-pyridin-2-yl)-7H-pyrrolo[2,3-d]pyrimidin-4-yl]-3,4,5,6-tetrahydro-2H-[1,3']bipyridinyl-4-ol;
3-amino-N-{5-[2-(6-methyl-pyridin-2-yl)-7H-pyrrolo[2,3-d]pyrimidin-4-yl]-pyridin-3-yl}-propionamide;
2-(6-methyl-pyridin-2-yl)-4-(5-morpholin-4-yl-pyridin-3-yl)-7H-pyrrolo[2,3-d]pyrimidine;
4-acetylamino-N-{5-[2-(6-methyl-pyridin-2-yl)-7H-pyrrolo[2,3-d]pyrimidin-4-yl]-pyridin-3-yl}-butyramide;
3-acetylamino-N-{5-[2-(6-methyl-pyridin-2-yl)-7H-pyrrolo[2,3-d]pyrimidin-4-yl]-pyridin-3-yl}-propionamide;
3-hydroxy-N-{5-[2-(6-methyl-pyridin-2-yl)-7H-pyrrolo[2,3-d]pyrimidin-4-yl]-pyridin-3-yl}-propionamide;
4-(4-methyl-pyridin-3-yl)-2-(6-methyl-pyridin-2-yl)-7H-pyrrolo[2,3-d]pyrimidine;
3-{5-[2-(6-methyl-pyridin-2-yl)-7H-pyrrolo[2,3-d]pyrimidin-4-yl]-pyridin-3-yl}-benzylamine;
4-{5-[2-(6-methyl-pyridin-2-yl)-7H-pyrrolo[2,3-d]pyrimidin-4-yl]-pyridin-3-yl}-benzylamine;
2-(6-methyl-pyridin-2-yl)-4-[5-(3-morpholin-4-ylmethyl-phenyl)-pyridin-3-yl]-7H-pyrrolo[2,3-d]pyrimidine;
2-(6-methyl-pyridin-2-yl)-4-[5-(4-morpholin-4-ylmethyl-phenyl)-pyridin-3-yl]-7H-pyrrolo[2,3-d]pyrimidine;
(4-{5-[2-(6-methyl-pyridin-2-yl)-7H-pyrrolo[2,3-d]pyrimidin-4-yl]-pyridin-3-yl}-phenyl)-methanol;
(3-{5-[2-(6-methyl-pyridin-2-yl)-7H-pyrrolo[2,3-d]pyrimidin-4-yl]-pyridin-3-yl}-phenyl)-methanol; and
4-(5-cyclohex-1-enyl-pyridin-3-yl)-2-(6-methyl-pyridin-2-yl)-7H-pyrrolo[2,3-d]pyrimidine; or a salt thereof.

6. A compound of the formula I according to claim 1, selected from the group of compounds with the names:
{5-[2-(6-methyl-pyridin-2-yl)-7H-pyrrolo[2,3-d]pyrimidin-4-yl]-pyridin-3-yl}-methanol;
5-[2-(6-methyl-pyridin-2-yl)-7H-pyrrolo[2,3-d]pyrimidin-4-yl]-pyridin-3-ol;
2-(6-methyl-pyridin-2-yl)-4-(5-[1,3,4]oxadiazol-2-yl-pyridin-3-yl)-7H-pyrrolo[2,3-d]pyrimidine;
2-(6-methyl-pyridin-2-yl)-4-(5-methylsulfanyl-pyridin-3-yl)-7H-pyrrolo[2,3-d]pyrimidine;
4-(5-methyl-pyridin-3-yl)-2-(6-methyl-pyridin-2-yl)-7H-pyrrolo[2,3-d]pyrimidine;
5-[2-(6-methyl-pyridin-2-yl)-7H-pyrrolo[2,3-d]pyrimidin-4-yl]-nicotinonitrile;
1-{5-[2-(6-methyl-pyridin-2-yl)-7H-pyrrolo[2,3-d]pyrimidin-4-yl]-3',6'-dihydro-2'H-[3,4']bipyridinyl-1'-yl}-ethanone;
1'-methyl-5-[2-(6-methyl-pyridin-2-yl)-7H-pyrrolo[2,3-d]pyrimidin-4-yl]-1',2',3',6'-tetrahydro-[3,4']bipyridinyl;
dimethyl-{5'-[2-(6-methyl-pyridin-2-yl)-7H-pyrrolo[2,3-d]pyrimidin-4-yl]-[2,3']bipyridinyl-5-ylmethyl}-amine;
5-[2-(6-methyl-pyridin-2-yl)-7H-pyrrolo[2,3-d]pyrimidin-4-yl]-3,4-dihydro-2H-pyrano[2,3-c]pyridine;
4-(5-cyclopent-1-enyl-pyridin-3-yl)-2-(6-methyl-pyridin-2-yl)-7H-pyrrolo[2,3-d]pyrimidine;
dimethyl-{5-[2-(6-methyl-pyridin-2-yl)-7H-pyrrolo[2,3-d]pyrimidin-4-yl]-[3,3']bipyridinyl-5-ylmethyl}-amine;
methyl-{5-[2-(6-methyl-pyridin-2-yl)-7H-pyrrolo[2,3-d]pyrimidin-4-yl]-[3,3']bipyridinyl-5-ylmethyl}-amine;
{5'-[2-(6-methyl-pyridin-2-yl)-7H-pyrrolo[2,3-d]pyrimidin-4-yl]-[3,3']bipyridinyl-5-yl}-methanol;
2-(6-methyl-pyridin-2-yl)-4-[5-(4-piperazin-2-yl-phenyl)-pyridin-3-yl]-7H-pyrrolo[2,3-d]pyrimidine;
dimethyl-[(R)-1-(4-{5-[2-(6-methyl-pyridin-2-yl)-7H-pyrrolo[2,3-d]pyrimidin-4-yl]-pyridin-3-yl}-benzyl)-pyrrolidin-3-yl]-amine;
2-(6-methyl-pyridin-2-yl)-4-[5-(3-piperazin-2-yl-phenyl)-pyridin-3-yl]-7H-pyrrolo[2,3-d]pyrimidine;
dimethyl-[(S)-1-(4-{5-[2-(6-methyl-pyridin-2-yl)-7H-pyrrolo[2,3-d]pyrimidin-4-yl]-pyridin-3-yl}-benzyl)-pyrrolidin-3-yl]-amine;
4-[5-(1-methyl-1H-pyrazol-4-yl)-pyridin-3-yl]-2-(6-methyl-pyridin-2-yl)-7H-pyrrolo[2,3-d]pyrimidine;
1-methyl-1-(4-{5-[2-(6-methyl-pyridin-2-yl)-7H-pyrrolo[2,3-d]pyrimidin-4-yl]-pyridin-3-yl}-phenyl)-ethylamine;
1-(4-{5-[2-(6-methyl-pyridin-2-yl)-7H-pyrrolo[2,3-d]pyrimidin-4-yl]-pyridin-3-yl}-phenyl)-ethylamine;
1-methyl-1-(3-{5-[2-(6-methyl-pyridin-2-yl)-7H-pyrrolo[2,3-d]pyrimidin-4-yl]-pyridin-3-yl}-phenyl)-ethylamine;
5-[2-(6-methyl-pyridin-2-yl)-7H-pyrrolo[2,3-d]pyrimidin-4-yl]-pyridin-3-ylamine;
5-[2-(6-methyl-pyridin-2-yl)-7H-pyrrolo[2,3-d]pyrimidin-4-yl]-1',2',3',6'-tetrahydro-[3,4']bipyridinyl;
2-(6-methyl-pyridin-2-yl)-4-[5-(3-pyrrolidin-2-yl-phenyl)-pyridin-3-yl]-7H-pyrrolo[2,3-d]pyrimidine;
6-{5-[2-(6-methyl-pyridin-2-yl)-7H-pyrrolo[2,3-d]pyrimidin-4-yl]-pyridin-3-yl}-1,2,3,4-tetrahydro-isoquinoline;
7-{5-[2-(6-methyl-pyridin-2-yl)-7H-pyrrolo[2,3-d]pyrimidin-4-yl]-pyridin-3-yl}-1,2,3,4-tetrahydro-isoquinoline;
(3-{5-[2-(6-methyl-pyridin-2-yl)-7H-pyrrolo[2,3-d]pyrimidin-4-yl]-pyridin-3-yl}-benzylamino)-acetic acid methyl ester;
(3-{5-[2-(6-methyl-pyridin-2-yl)-7H-pyrrolo[2,3-d]pyrimidin-4-yl]-pyridin-3-yl}-benzylamino)-acetic acid;

(4-{5-[2-(6-methyl-pyridin-2-yl)-7H-pyrrolo[2,3-d]pyrimidin-4-yl]-pyridin-3-yl}-benzylamino)-acetic acid methyl ester;

(4-{5-[2-(6-methyl-pyridin-2-yl)-7H-pyrrolo[2,3-d]pyrimidin-4-yl]-pyridin-3-yl}-benzylamino)-acetic acid;

2-(6-methyl-pyridin-2-yl)-4-[5-(1H-tetrazol-5-yl)-pyridin-3-yl]-7H-pyrrolo[2,3-d]pyrimidine;

4-(5-ethynyl-pyridin-3-yl)-2-(6-methyl-pyridin-2-yl)-7H-pyrrolo[2,3-d]pyrimidine;

4-{5-[3-(4-methyl-piperazin-1-yl)-prop-1-ynyl]-pyridin-3-yl}-2-(6-methyl-pyridin-2-yl)-7H-pyrrolo[2,3-d]pyrimidine;

2-[methyl-(3-{5-[2-(6-methyl-pyridin-2-yl)-7H-pyrrolo[2,3-d]pyrimidin-4-yl]-pyridin-3-yl}-benzyl)-amino]-ethanol;

2-(3-{5-[2-(6-methyl-pyridin-2-yl)-7H-pyrrolo[2,3-d]pyrimidin-4-yl]-pyridin-3-yl}-benzylamino)-ethanol;

2-(4-{5-[2-(6-methyl-pyridin-2-yl)-7H-pyrrolo[2,3-d]pyrimidin-4-yl]-pyridin-3-yl}-benzylamino)-ethanol;

[methyl-(3-{5-[2-(6-methyl-pyridin-2-yl)-7H-pyrrolo[2,3-d]pyrimidin-4-yl]-pyridin-3-yl}-benzyl)-amino]-acetic acid;

or a salt thereof.

7. A pharmaceutical composition comprising a compound according to claim 1 in admixture with a pharmaceutically acceptable excipient, diluent or carrier.

8. The compound of claim 1, or a salt thereof wherein $T_2$ is selected from quinolinyl, isoquinolinyl or 3,4-dihydro-2H-pyranopyridinyl.

9. The compound of claim 2, or a salt thereof wherein $T_2$ is selected from quinolinyl, isoquinolinyl or 3,4-dihydro-2H-pyranopyridinyl.

* * * * *